US008865864B2

(12) United States Patent
Cochran et al.

(10) Patent No.: US 8,865,864 B2
(45) Date of Patent: Oct. 21, 2014

(54) MUTANT EPIDERMAL GROWTH FACTOR POLYPEPTIDES WITH IMPROVED BIOLOGICAL ACTIVITY AND METHODS OF THEIR MAKING AND USE

(75) Inventors: Jennifer R. Cochran, Stanford, CA (US); Bertrand Howyen Lui, Menlo Park, CA (US); Jennifer Lynn Lahti, Half Moon Bay, CA (US); James R. Swartz, Menlo Park, CA (US); Bob Chen, Stanford, CA (US); Cheuk Lun Leung, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 13/595,923

(22) Filed: Aug. 27, 2012

(65) Prior Publication Data

US 2013/0053314 A1    Feb. 28, 2013

Related U.S. Application Data

(60) Provisional application No. 61/575,783, filed on Aug. 26, 2011.

(51) Int. Cl.
*C07K 14/485*    (2006.01)
(52) U.S. Cl.
CPC .................................. *C07K 14/485* (2013.01)
USPC .......................................... 530/324; 530/399
(58) Field of Classification Search
CPC ......................... A61K 38/1808; C07K 14/485
See application file for complete search history.

(56) References Cited

U.S. PATENT DOCUMENTS

| | | | |
|---|---|---|---|
| 5,434,135 A * | 7/1995 | Parikh et al. | 514/7.6 |
| 6,191,106 B1 | 2/2001 | Mullenbach et al. | |
| 2003/0171269 A1* | 9/2003 | Magil et al. | 514/12 |
| 2008/0249008 A1 | 10/2008 | Cochran et al. | |

FOREIGN PATENT DOCUMENTS

WO    2005/070960    8/2005

OTHER PUBLICATIONS

Cochran; et al., "Improved mutants from directed evolution are biased to orthologous substitutions", Protein Engineering Design & Selection (Mar. 2006), 19(6):245-253.
Coco; et al., "Growth factor engineering by degenerate homoduplex gene family recombination", Nature Biotechnology (Dec. 2002), 20:1246-1250.
Lahti, "Combinatorial, Rational, and Bioinformatics Approaches to Engineering Cystine-Rich Proteins", A Dissertation Submitted to the Department of Bioengineering and the Committee on Graduate Studies of Stanford University in Partial Fulfillment of the Requirements for the Degree of Doctor of Philosophy (Aug. 2010), http://purl.stanford.edu/cn226gk5965.
Lahti; et al., "Engineered epidermal growth factor mutants with faster binding on-rates correlate with enhanced receptor activation", FEBS Lett. (Apr. 2011), 585(8):1135-1139.
Lui, "Cell-Free Methods to Engineer Therapeutic Proteins: Improving the Efficacy of Epidermal Growth Factor", A Dissertation Submitted to the Department of Bioengineering and the Committee on Graduate Studies of Stanford University in Partial Fulfillment of the Requirements for the Degree of Doctor of Philosophy (Dec. 2010), http://purl.stanford.edu/jz962hg7602.
Lui; et al., "Discovery of Improved EGF Agonists Using a Novel In Vitro Screening Platform", Journal of Molecular Biology (Aug. 2011), 413:406-415.
Mullenbach; et al., "Modification of a receptor-binding surface of epidermal growth factor (EGF): analogs with enhanced receptor affinity at low pH or at neutrality", Protein Engineering (1998), 11(6):473-480.
Shiah; et al., "Pseudomonas Exotoxin A-Epidermal Growth Factor (EGFM) utant Chimeric Protein as an Indicator for Identifying Amino Acid Residues Important in EGF-Receptor Interaction", The Journal of Biological Chemistry (Nov. 1992), 267(33):24034-24040.
Van De Poll; et al., "A Single Amino Acid Exchange, Arg-45 to Ala, Generates an Epidermal Growth Factor (EGF) Mutant with High Affinity for the Chicken EGF Receptor", The Journal of Biological Chemistry (Sep. 1995), 270(38):22337-22343.

* cited by examiner

*Primary Examiner* — Marianne P Allen
(74) *Attorney, Agent, or Firm* — Bozicevic, Field & Francis LLP; Pamela J. Sherwood

(57) ABSTRACT

Compositions that are EGF polypeptides that possess improved biological activity as compared to the biological activity exhibited by wild-type EGF are provided. Also provided are methods for the preparation of these mutants, methods for the use of these mutants, methods for rationally designing new polypeptide mutants, and methods for screening mutants polypeptides to identify novel EGF mutants with desirable biological activities.

1 Claim, 39 Drawing Sheets
(20 of 39 Drawing Sheet(s) Filed in Color)

|   | 1 | 2 | 3 | 4 | 5 | 6 | 7 | 8 | 9 | 10 | 11 | 12 |
|---|---|---|---|---|---|---|---|---|---|----|----|----|
| A | 848 | 984 | 760 | 7032 | 768 | 792 | 760 | 728 | 864 | 888 | 736 | 856 |
| B | 824 | 7912 | 864 | 856 | 768 | 3880 | 3104 | 856 | 3096 | 848 | 832 | 8152 |
| C | 968 | 792 | 8108 | 3216 | 904 | 824 | 832 | 856 | 840 | 7568 | 808 | 6208 |
| D | 4352 | 864 | 3224 | 912 | 1080 | 848 | 776 | 856 | 784 | 848 | 5328 | 5672 |
| E | 6040 | 5408 | 856 | 3356 | 888 | 4952 | 872 | 824 | 832 | 856 | 840 | 768 |
| F | 880 | 5512 | 840 | 856 | 888 | 912 | 4576 | 960 | 800 | 840 | 1128 | 792 |
| G | 1040 | 824 | 832 | 864 | 896 | 888 | 792 | 838 | 816 | 824 | 856 | 824 |
| H | 7488 | 8072 | 824 | 8064 | 856 | 3652 | 5336 | 6456 | 912 | 768 | 816 | 784 |

SEQUENCE LISTING

<160> NUMBER OF SEQ ID NOS: 19

<210> SEQ ID NO 1
<211> LENGTH: 53
<212> TYPE: PRT
<213> ORGANISM: Artificial Sequence
<220> FEATURE:
<223> OTHER INFORMATION: synthetic peptide

<400> SEQUENCE: 1

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50

<210> SEQ ID NO 2
<211> LENGTH: 53
<212> TYPE: PRT

<213> ORGANISM: Artificial Sequence
<220> FEATURE:
<223> OTHER INFORMATION: synthetic peptide

<400> SEQUENCE: 2

Asn Ser Gly Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ala Gly Glu Arg Cys Gln Tyr Arg Asp Leu Lys
        35                  40                  45

Arg Trp Glu Leu Arg
    50

<210> SEQ ID NO 3
<211> LENGTH: 53
<212> TYPE: PRT
<213> ORGANISM: Artificial Sequence
<220> FEATURE:
<223> OTHER INFORMATION: synthetic peptide

<400> SEQUENCE: 3

Asn Ser Asp Ser Lys Cys Pro Pro Ser His Asp Glu Tyr Cys Leu His
1               5                   10                  15

Asp Gly Val Cys Met Tyr Val Glu Ala Leu Asp Arg Tyr Ala Cys Asn
            20                  25                  30

Cys Val Val Gly Tyr Thr Gly Glu Arg Cys Gln Tyr Arg Asp Leu Arg
        35                  40                  45

Trp Trp Lys Leu Arg
    50

<210> SEQ ID NO 4
<211> LENGTH: 53
<212> TYPE: PRT
<213> ORGANISM: Artificial Sequence
<220> FEATURE:
<223> OTHER INFORMATION: synthetic peptide

<400> SEQUENCE: 4

Asn Ser Asn Ser Glu Cys Pro Leu Ser His Asp Gly Tyr Cys Leu His
1               5                   10                  15

Asp Gly Val Cys Arg Tyr Ile Glu Ala Leu Asp Lys Tyr Ala Cys Asn
            20                  25                  30

Cys Val Val Gly Tyr Val Gly Glu Arg Cys Gln Tyr Arg Asp Leu Arg
        35                  40                  45

Arg Trp Glu Leu Arg
    50

<210> SEQ ID NO 5
<211> LENGTH: 53
<212> TYPE: PRT
<213> ORGANISM: Artificial Sequence
<220> FEATURE:
<223> OTHER INFORMATION: synthetic peptide

<400> SEQUENCE: 5

His Ser Asn Ser Glu Cys Pro Leu Ser His Asp Gly Tyr Cys Leu His
1               5                   10                  15

Asp Gly Val Cys Met Tyr Ile Lys Ala Leu Asp Thr Tyr Ala Cys Asn
            20                  25                  30

Cys Val Val Gly Tyr Val Gly Glu Arg Cys Gln Tyr Pro Asp Leu Lys

```
                35                  40                  45

Trp Trp Gly Leu Arg
    50

<210> SEQ ID NO 6
<211> LENGTH: 50
<212> TYPE: DNA
<213> ORGANISM: Artificial Sequence
<220> FEATURE:
<223> OTHER INFORMATION: synthetic oligonucleotide

<400> SEQUENCE: 6
gtggtggtgg ttctggtggt ggtggttctg gtggtggtgg ttctgctagc              50

<210> SEQ ID NO 7
<211> LENGTH: 50
<212> TYPE: DNA
<213> ORGANISM: Artificial Sequence
<220> FEATURE:
<223> OTHER INFORMATION: synthetic oligonucleotide

<400> SEQUENCE: 7
atctcgagct attacaagtc ctcttcagaa ataagctttt gttcggatcc              50

<210> SEQ ID NO 8
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 8
acacgacgtg aacgatagga attga                                        25

<210> SEQ ID NO 9
<211> LENGTH: 53
<212> TYPE: PRT
<213> ORGANISM: Artificial Sequence
<220> FEATURE:
<223> OTHER INFORMATION: synthetic peptide

<400> SEQUENCE: 9

Asn Ser Asn Ser Glu Cys Pro Leu Ser His Asp Gly Tyr Cys Leu Asn
  1               5                  10                  15

Asp Gly Val Cys Arg Tyr Ile Glu Ala Leu Asp Lys Tyr Ala Cys Asn
             20                  25                  30

Cys Val Val Gly Tyr Val Gly Glu Arg Cys Gln Tyr Arg Asp Leu Arg
         35                  40                  45

Arg Trp Glu Leu Arg
    50

<210> SEQ ID NO 10
<211> LENGTH: 53
<212> TYPE: PRT
<213> ORGANISM: Artificial Sequence
<220> FEATURE:
<223> OTHER INFORMATION: synthetic peptide

<400> SEQUENCE: 10

His Ser Asn Ser Glu Cys Pro Leu Ser His Asp Gly Tyr Cys Leu Asn
  1               5                  10                  15

Asp Gly Val Cys Met Tyr Ile Lys Ala Leu Asp Thr Tyr Ala Cys Asn
             20                  25                  30
```

Cys Val Val Gly Tyr Val Gly Glu Arg Cys Gln Tyr Pro Asp Leu Lys
            35                  40                  45

Trp Trp Gly Leu Arg
    50

<210> SEQ ID NO 11
<211> LENGTH: 53
<212> TYPE: PRT
<213> ORGANISM: Artificial Sequence
<220> FEATURE:
<223> OTHER INFORMATION: synthetic peptide

<400> SEQUENCE: 11

Asn Ser Asn Ser Glu Cys Pro Leu Ser His Asp Gly Tyr Cys Leu Asn
 1               5                   10                  15

Asp Gly Val Cys Arg Tyr Ile Glu Ala Leu Asp Lys Tyr Ala Cys Asn
            20                  25                  30

Cys Val Val Gly Tyr Val Gly Glu Arg Cys Gln His Arg Asp Leu Arg
            35                  40                  45

Arg Trp Glu Leu Arg
    50

<210> SEQ ID NO 12
<211> LENGTH: 53
<212> TYPE: PRT
<213> ORGANISM: Artificial Sequence
<220> FEATURE:
<223> OTHER INFORMATION: synthetic peptide

<400> SEQUENCE: 12

His Ser Asn Ser Glu Cys Pro Leu Ser His Asp Gly Tyr Cys Leu Asn
 1               5                   10                  15

Asp Gly Val Cys Met Tyr Ile Lys Ala Leu Asp Thr Tyr Ala Cys Asn
            20                  25                  30

Cys Val Val Gly Tyr Val Gly Glu Arg Cys Gln His Pro Asp Leu Lys
            35                  40                  45

Trp Trp Gly Leu Arg
    50

<210> SEQ ID NO 13
<211> LENGTH: 53
<212> TYPE: PRT
<213> ORGANISM: Artificial Sequence
<220> FEATURE:
<223> OTHER INFORMATION: synthetic peptide

<400> SEQUENCE: 13

Ser Arg Gly Ser Lys Cys Pro Pro Ser His Asp Gly Tyr Cys Leu Gln
 1               5                   10                  15

Gly Gly Val Cys Met Tyr Ile Glu Ala Leu Asp Arg Tyr Ala Cys Asn
            20                  25                  30

Cys Val Val Gly Tyr Ala Gly Arg Cys Gln Tyr Arg Asp Leu Thr
            35                  40                  45

Trp Trp Gly Arg Arg
    50

<210> SEQ ID NO 14
<211> LENGTH: 53
<212> TYPE: PRT
<213> ORGANISM: Artificial Sequence
<220> FEATURE:
<223> OTHER INFORMATION: synthetic peptide

<400> SEQUENCE: 14

Ser Arg Gly Ser Lys Cys Pro Pro Ser His Asp Gly Tyr Cys Leu His
1               5                   10                  15

Gly Gly Val Cys Met Tyr Ile Glu Ala Leu Asp Arg Tyr Ala Cys Asn
            20                  25                  30

Cys Val Val Gly Tyr Ala Gly Glu Arg Cys Gln Tyr Arg Asp Leu Thr
        35                  40                  45

Trp Trp Gly Arg Arg
        50

<210> SEQ ID NO 15
<211> LENGTH: 53
<212> TYPE: PRT
<213> ORGANISM: Artificial Sequence
<220> FEATURE:
<223> OTHER INFORMATION: synthetic peptide

<400> SEQUENCE: 15

Ser Arg Gly Ser Lys Cys Pro Pro Ser His Asp Gly Tyr Cys Leu Gln
1               5                   10                  15

Gly Gly Val Cys Met Tyr Ile Glu Ala Leu Asp Arg Tyr Ala Cys Asn
            20                  25                  30

Cys Val Val Gly Tyr Ala Gly Glu Arg Cys Gln His Arg Asp Leu Thr
        35                  40                  45

Trp Trp Gly Arg Arg
        50

<210> SEQ ID NO 16
<211> LENGTH: 53
<212> TYPE: PRT
<213> ORGANISM: Artificial Sequence
<220> FEATURE:
<223> OTHER INFORMATION: synthetic peptide

<400> SEQUENCE: 16

Asn Ser Asp Ser Glu Cys Pro Leu Ser His Asp Gly Tyr Cys Leu His
1               5                   10                  15

Gly Gly Val Cys Met Tyr Ile Lys Ala Val Asp Arg Tyr Ala Cys Asn
            20                  25                  30

Cys Val Val Gly Tyr Ile Gly Glu Arg Cys Gln Tyr Arg Asp Leu Thr
        35                  40                  45

Trp Trp Gly Pro Arg
        50

<210> SEQ ID NO 17
<211> LENGTH: 53
<212> TYPE: PRT
<213> ORGANISM: Artificial Sequence
<220> FEATURE:
<223> OTHER INFORMATION: synthetic peptide

<400> SEQUENCE: 17

Asn Ser Tyr Ser Glu Cys Pro Pro Tyr Asp Gly Tyr Cys Leu His
1               5                   10                  15

Asp Gly Val Cys Arg Tyr Ile Glu Ala Leu Asp Ser Tyr Ala Cys Asn
            20                  25                  30

Cys Val Val Gly Tyr Ala Gly Glu Arg Cys Gln Tyr Arg Asp Leu Arg
        35                  40                  45

Trp Trp Gly Arg Arg

```
<210> SEQ ID NO 18
<211> LENGTH: 62
<212> TYPE: DNA
<213> ORGANISM: Artificial Sequence
<220> FEATURE:
<223> OTHER INFORMATION: synthetic oligonucleotide

<400> SEQUENCE: 18
acacgacgtg aacgatagga attgaaacga gttcgcggcc gcttaggcac cccaggcttt    60
ac                                                                  62

<210> SEQ ID NO 19
<211> LENGTH: 64
<212> TYPE: DNA
<213> ORGANISM: Artificial Sequence
<220> FEATURE:
<223> OTHER INFORMATION: synthetic oligonucleotide

<400> SEQUENCE: 19
acacgacgtg aacgatagga attgaaacga gttcgacgag cgtcagcttg catgccctgc    60
agct                                                                64
```

MUTANT EPIDERMAL GROWTH FACTOR POLYPEPTIDES WITH IMPROVED BIOLOGICAL ACTIVITY AND METHODS OF THEIR MAKING AND USE

CROSS REFERENCE TO RELATED APPLICATIONS

Pursuant to 35 U.S.C. §119 (e), this application claims priority to the filing date of the U.S. Provisional Patent Application Ser. No. 61/575,783 filed Aug. 26, 2011; the disclosure of which are herein incorporated by reference.

FIELD OF THE INVENTION

The present invention relates to the field of epidermal growth factor (EGF) polypeptides with improved biological activity.

BACKGROUND OF THE INVENTION

Epidermal growth factor (EGF) is a 6.2 kDa polypeptide that specifically binds to the epidermal growth factor receptor (EGFR). EGF contains 53 amino acids with three internal disulfide bridges, and has the amino acid sequence shown in SEQ ID NO:1.

Binding of EGF to its receptor induces a conformational change in the receptor and receptor aggregation (Greenfield, et al., EMBO J. 8:4115-4123, 1989; Varden and Schlessinger, Biochem, 26: 1443-1451, 1987). Receptor aggregation stimulates an intrinsic tyrosine kinase activity in the cytoplasmic domain of EGFR, which in turn leads to recruitment and phosphorylation of other substrates, resulting in mitogenic signaling and/or a variety of other cellular activities (Paw on and Schlessinger, Curr. Biol. 3:434-442, 1994; Alroy and Varden, FEBS Lett. 410:83-86, 1997; Riese and Stern, Bioessays 20:41-48, 1998).

Therapies that promote EGFR signaling find use in treating a diverse range of conditions. EGF super-agonists have long been sought due to their potential applications in wound healing, tissue engineering and regenerative medicine. For example, stimulation of EGFR with EGF has been shown to accelerate wound healing, (e.g., in gastric and oral ulcers, diabetic foot ulcers, skin grafts, corneal epithelial wounds, and tympanic membrane perforations (Milani and Calabro, Microsc. Res. Tech. 52:360-371, 2001; Fujisawa, et al, J. Oral Pathol. Med. 32:358~366, 2003; Bennett, et al, Br J Surg. 90:133~146, 2003: Brown, et al, N. Engl. J. Med. 321:7~79, 1989; Lu, at al, Exp. Biol. Med. (Maywood) 226:653~64, 2001; Ma, at al, Acta Otolaryngol. 122:586~599, 2002). As another example, stimulation of EGFR has been demonstrated to regulate nerve regeneration and atherogenesis (Xian and Zhou, Mol Neurobiol 20: 157-183, 1999; Lamb, et al, Atherosclerosis 168: 191-194, 2003).

Historically, attempts to discover EGF agonists with improved biological activity by means of screening for EGFR kinase activity, reporter gene expression, or increased binding affinity to EGFR have met with limited success (see, e.g., Coco et al., (2002). Nat Biotechnol 20, 124-50; Sounau et al., (1997) Nucleic Acids Res 25, 1585-90: Souriau et al., Biol Chem 380). Similarly, attempts to engineer such mutants have faded to yield molecules with the desired activity (see e.g. U.S. Pat. No. 5,547,935, issued to Mullenbach et al. and U.S. Pat. No. 7,084,246, issued to Coco et al., hereby incorporated by reference in their entirety), due to a previous lack of understanding as to aspects of the process by which receptor binding effects cellular changes, i.e., as to intracellular trafficking and downstream signaling.

There is therefore a long-felt and previously unmet need in the art for EGF polypeptides with improved biological activity as compared to the activity exhibited by the wild-type molecule. Further, there is a long-felt and previously unmet need in the art for a high-throughput method of identifying mutant EGF polypeptides having improved biological activity as compared to the activity of wild-type EGF, which method is both effective and not excessively costly in terms of money, time and effort. Further, there is a long-felt and previously unmet need in the art for a method of rationally engineering mutant EGF polypeptides having improved biological activity. Further, there is a long-felt and previously unmet need in the art for an effective method of treating wounds using mutant EGF polypeptides having improved biological activity.

The present invention addresses these issues.

SUMMARY OF THE INVENTION

Compositions that are EGF polypeptides that possess improved biological activity as compared to the biological activity exhibited by wild-type EGF are provided. Also provided are methods for the preparation of these mutants, methods for the use of these mutants, methods for rationally designing new polypeptide mutants, and methods for screening mutant polypeptides to identify novel EGF mutants with desirable biological activities.

In some aspects, the present invention encompasses engineered mutant EGF polypeptides having improved biological activity. In some embodiments, the mutant EGF polypeptide demonstrates an EGFR binding off-rate at physiological pH that is faster than that of wild type EGF, an EGFR binding on-rate that is comparable to that of wild type EGF, and a binding affinity for EGFR at physiological or acidic pH that is weaker than the binding affinity of wild type EGF. In some embodiments, the improved biological activity is less activity in promoting phosphorylation of EGFR than wild type EGF. In some embodiments, the improved biological activity is less activity in promoting the downregulation of EGFR from the cell surface than wild type EGF. In some embodiments, the improved biological activity is more activity in promoting cellular proliferation than wild type EGF. In some embodiments, the mutant EGF polypeptide comprises a substitution in one or more residues of SEQ ID NO:1 selected from the group consisting of residues 3, 5, 8, 12, 23, 28, 38, 48, 49, and 51. In certain embodiments, the mutant EGF polypeptide is a mutant comprising substitutions at residues 38 and 49, e.g. mutant 38+49 (SEQ ID NO:20) or mutant 1.10 (SEQ ID NO:2), or a variant thereof, e.g. a polypeptide having a sequence identity of 80% or more, 85% or more, or 90% or more to such a mutant. In certain embodiments, the mutant EGF polypeptide is a mutant comprising substitutions at residues 5, 8, 12, 23, 28, 38, 48 and 51, e.g. mutant 1.78 (SEQ ID NO:3), or a variant thereof, e.g. a polypeptide having a sequence identity of 80% or more, 85% or more, or 90% or more to such a mutant.

In some embodiments, the mutant EGF polypeptide demonstrates an EGFR binding off-rate at physiological pH that is faster than that of wild type EGF, and an EGFR binding on-rate at physiological pH that is faster than that of wild type EGF. In certain embodiments, the mutant has a binding affinity for EGFR at physiological pH that is comparable to or stronger than that of wild type EGF. In certain embodiments, the mutant has a binding, affinity for EGFR at acidic pH that is weaker than that of a parent mutant from which it was derived. In some embodiments, the improved biological activity is more activity in promoting EGFR phosphorylation relative to wild type EGF. In some embodiments, the improved biological activity is less activity in promoting the downregulation of EGFR from the cell surface than wild type EGF. In some embodiments, the mutant EGF polypeptide comprises a substitution in one or more residues of SEQ ID NO:1 selected from the group consisting of residues 1, 2, 3, 5, 8, 16, 17, 21, 24, 28, 38, 44, 45, 48, 49, 51, and 52, and comprises a histidine at residues 16 and/or 44. In certain embodiments, the mutant EGF polypeptide is a mutant comprising substitutions in residues 3, 21, 38, 48, and 49, e.g. m100_16H (SEQ ID NO:4), and m100_44H (SEQ ID NO:11), or a variant thereof, i.e. a polypeptide having a sequence identity of 80% or more, 85% or more, or 90% or more to m100_216H. In certain embodiments, the mutant EGF polypeptide is a mutant comprising substitutions in residues 1, 3, 24, 28, 38, 45, and 51, e.g. m102_16H (SEQ ID NO:5) and m102_44H (SEQ ID NO:12), or a variant thereof, i.e. a polypeptide having a sequence identity of 80% or more, 85% or more, or 90% or more to m102_16H.

In some embodiments, the mutant EGF polypeptide demonstrates an EGFR binding on-rate at physiological pH that is faster than that of wild type EGF polypeptide, and a binding affinity for the EGF receptor at physiological or acidic pH that is stronger than the binding affinity of wild type EGF. In some embodiments, the improved biological activity is more activity in promoting EGFR phosphorylation, in some embodiments, the improved biological activity is more activity in promoting the downregulation of EGFR from the cell surface than wild type EGF. In some embodiments, the improved biological activity is more activity in promoting cellular migration than wild type EGF. In some embodiments, the mutant EGF polypeptide comprises a substitution in one or more residues of SEQ ID NO:1 selected from the group consisting of residues 3, 8, 10, 16, 17, 21, 24, 26, 28, 38, 48, 49, 51, and 52. In certain embodiments, the mutant EGF polypeptide is a mutant comprising substitutions in residues 3, 17, 24, 26, 28, 48, 51 and 52, e.g. m28 (SEQ ID NO:16). In certain embodiments, the mutant EGF polypeptide comprises substitutions in residues 3, 8, 10, 21, 28, 38, 48, 51, and 56, e.g. m123 (SEQ ID NO:17). In certain embodiments, the mutant EGF polypeptide comprises substitutions in residues 3, 16, 21, 38, 48, and 49, e.g. m100 (SEQ ID NO:9). In certain embodiments, the mutant EGF polypeptide comprises substitutions in residues 1, 3, 16, 21, 38, 45, and 51, e.g. m102 (SEQ ID NO: 10).

As described in greater detail below, mutant EGFR polypeptides compositions with improved biological activity were identified following a novel screening method that overcomes the hurdles in the art of purifying transcribed and translated protein prior to assaying for its biological activity. As such, in some aspects of the invention, a method is provided for identifying mutant EGFR polypeptides which exhibit increased biological activity as compared to the activity exhibited by wild-type EGF, which method includes providing a DNA library comprising a plurality of nucleic acid molecules each encoding a mutant EGF polypeptide sequence; dispensing the nucleic acid molecules into separate reaction vessels; amplifying the nucleic acid molecules in an amount sufficient to permit protein expression; translating each of the nucleic acid molecules into the mutant EGF polypeptide which it encodes using an oxidizing cell-free protein synthesis system; assessing the mutant EGF polypeptides for a parameter of biological activity; and identifying mutant EGF polypeptides having improved biological activity. In some embodiments, the parameter of biological activity is the phosphorylation of the EGF receptor, the downregulation of the EGF receptor from the cell surface, or cellular response, e.g. proliferation, migration, and/or invasion. In some aspects, the present invention encompasses mutant. EGF polypeptides identified by the method. In alternate exemplary embodiments, the mutant. EGF polypeptides identified by that method comprise an amino acid sequence selected from the group consisting of 1.10 (SEQ ID NO: 2) and 1.78 (SEQ ID NO: 3).

As also described in greater detail below, the analysis of mutant EGF polypeptides with improved biological activity has led to the surprising discovery that particular ligand-receptor binding kinetics, e.g. receptor binding on-rate ($k_{on}$), receptor binding off-rate ($k_{off}$), receptor affinity at physiological or acidic pH, unexpectedly correlate with certain improved biological activities, e.g. in promoting EGF receptor (EGFR) phosphorylation, EGFR downregulation on the cell surface, cellular responses, and the like. For example, engineering of mutant EGF polypeptides so as to have an increased receptor binding off-rate ($k_{off}$) at physiological or acidic pH results in mutant EGF polypeptides having improved biological activity, for example, in promoting EGFR-mediated cell proliferation relative to that exhibited by wild-type EGF. As another example, engineering of mutant EGF polypeptides so as to have an increased receptor binding on-rate ($K_{on}$) at physiological or acidic pH results in mutant EGF polypeptides having improved biological activity, for example in promoting EGFR-mediated migration relative to that exhibited by wild-type EGF. As a third example, engineering a mutant EGF polypeptide to increase its binding sensitivity to pH over that of the parent mutant (e.g. an off-rate at physiological pH that is faster than that of its corresponding parent mutant EGF polypeptide, and/or a binding affinity for EGFR at acidic pH that is significantly weaker than that of its corresponding parent mutant EGF polypeptide) by substituting a histidine at key residues, e.g. residue 16, results in mutant EGF polypeptides having improved biological activity in promoting more EGFR phosphorylation and less downregulation/degradation of EGFR than the EGF parent mutant.

Accordingly, in some aspects of the invention, methods are provided for identifying mutant EGF polypeptides having improved biological activity on the basis of binding kinetics, e.g. receptor binding on-rates, receptor binding off-rates, or receptor binding affinity under physiological or acidic conditions, or some combination thereof. In some embodiments, the method includes the steps of contacting a receptor or extracellular fragment thereof with a mutant EGF polypeptide; assessing the binding kinetics of the mutant EGF polypeptide to the EGFR or fragment thereof; comparing the binding kinetics of mutant EGF polypeptide to the binding kinetics of a control EGF polypeptide; and identifying a mutant EGF polypeptide having improved biological activity based on the comparison. In some embodiments, the control EGF polypeptide is a wild type polypeptide. In some embodiments, assessing the binding kinetics comprises assessing the off-rate for binding of the mutant EGF polypeptide to the EGFR. In some embodiments, an increased off-rate relative to the wild type polypeptide indicates that the mutant EGF polypeptide has improved activity in promoting cell proliferation. In some embodiments, assessing the binding kinetics comprise assessing the on-rate for binding of the mutant EGF polypeptide to the EGFR. In some embodiments, an increased on-rate relative to the wild type polypeptide indicates that the mutant EGF polypeptide has improved activity in promoting cell migration. In some embodiments, the source of the mutant polypeptide is a library, for example a DNA library comprising a plurality of nucleic acid molecules each encoding a mutant EGF polypeptide sequence. In some such embodiments, the method comprises dispensing the nucleic acid molecules into separate reaction vessels; amplifying the nucleic acid molecules in an amount sufficient to permit protein expression; translating each of the nucleic acid molecules into the mutant EGF polypeptide which it encodes, e.g. using an oxidizing cell-free protein synthesis system; and assessing the binding kinetics of the translated mutant EGF polypeptides.

In some aspects, the present invention encompasses a method of therapeutic treatment comprising administering a therapeutically effective amount of a polypeptide comprising an isolated mutant EGF polypeptide having improved biological activity to a subject in need of such treatment. In one exemplary embodiment, the subject is a mammal. In a further exemplary embodiment, the subject is a human.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION OF THE INVENTION

Figure 1:
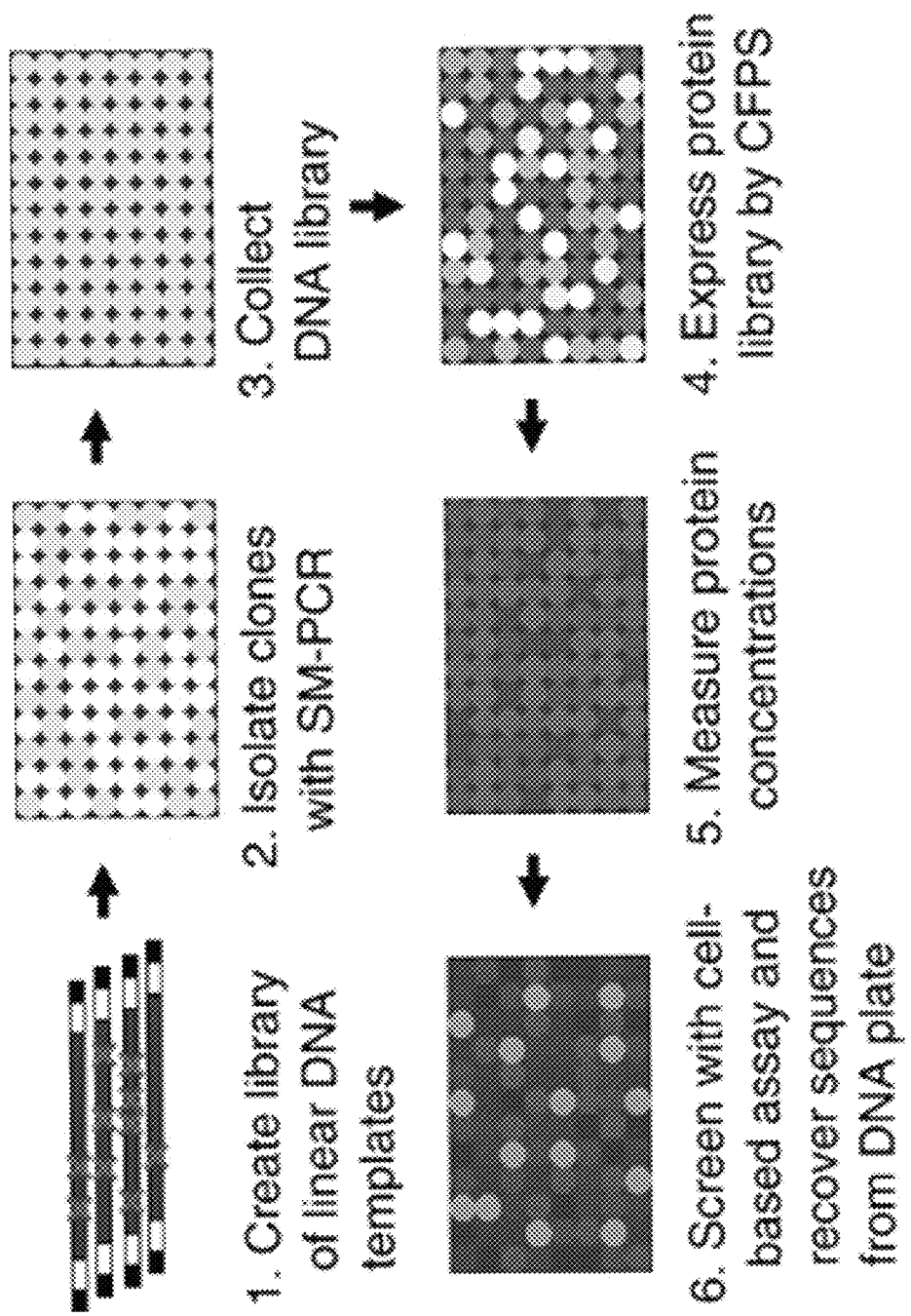
FIG. 1. Diagram of the platform's six steps to screen a library of protein mutants for improved biological activity. (1) A library of linear DNA templates is prepared with the proper elements for SM-PCR and CFPS. (2) The DNA library is diluted into microtiter plate wells to separate the templates and amplified by SM-PCR. (3) Successful SM-PCR reactions are collected into full plates for screening. (4) The protein library is then expressed by CFPS. (5) The concentration of each protein is determined and (6) the library is screened with a cell-based functional assay at a uniform dosage. The sequences of proteins that exhibit enhanced biological function are determined by sequencing the corresponding wells in the DNA plates.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and the include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Compositions that are EGF polypeptides that possess improved biological activity as compared to the biological activity exhibited by wild-type EGF are provided. Also provided are methods for the preparation of these mutants, methods for the use of these mutants, methods for rationally designing new polypeptide mutants, and methods for screening mutants polypeptides to identify novel EGF mutants with desirable biological activities. These and other objects, advantages, and features of the invention will become apparent to those persons skilled in the art upon reading the details of the compositions and methods as more fully described below. In describing the aspects of the invention, compositions and methods for their preparation will be described first, followed by methods for their use and methods for screening mutant polypeptide ligands to identify novel receptor agonists.

Mutant EGF Polypeptides and Nucleic Acids Encoding Same

The present invention features mutant epidermal growth factor (EGF) polypeptide compositions having improved biological activity. By a mutant EGF polypeptide composition, it is meant an isolated polypeptide comprising an EGF polypeptide that is a mutant, or "variant", of a native EGF polypeptide. The terms "EGF gene product", "EGF polypeptide", "EGF peptide", and "EGF protein" are used interchangeably herein to refer to native EGF polypeptides, EGF polypeptide variants, EGF polypeptide fragments and chimeric EGF polypeptides. By "native polypeptide" it is meant a polypeptide found in nature. For example, native EGF polypeptides include human EGF, the sequence for which may be found at SEQ ID NO:1, as well as EGF homologs that naturally occur in humans and EGF orthologs that naturally occur in other eukaryotes, e.g. protist, fungi, plants or animals, for example yeast, insects, nematodes sponge, mammals, non-mammalian vertebrates. By "mutant" or "variant" it is meant a mutant of the native polypeptide having less than 100% sequence identity with the native sequence. For example, a variant may be a polypeptide having 60% sequence identity or more with a full length native EGF, e.g. SEQ ID NO:1, e.g. 65%, 70%, 75%, or 80% or more identity, such as 85%, 90%, or 95% or more identity, for example, 98% or 99% identity with the full length native EGF. Variants also include fragments of a native EGF polypeptide that have 60% sequence identity or more with a fragment of native EGF having EGFR binding activity, e.g. 65%, 70%, 75%, or 80% or more identity, such as 85%, 90%, or 95% or more identity, for example, 98% or 99% identity with a native EGF fragment that can bind EGFR under physiological conditions, or the comparable sequence in a EGF homolog or ortholog. Human EGF is provided here as an example of a native EGF polypeptide, but it will be appreciated by the ordinarily skilled artisan that native EGF polypeptides from any eukaryote and variants thereof may be employed in designing mutant EGF polypeptides, these native EGF polypeptides being readily identified using publicly available resources such as PubMed or NCBI Blast, and binding activity of these native EGF polypeptides and fragments thereof being known in the art or readily determined by the ordinarily skilled artisan using the methods described herein. Exemplary mutant EGF polypeptides encompassed herein include, for example, 1.10 (SEQ ID NO:2), 1.78 (SEQ ID NO:3), m28 (SEQ ID NO:16), m123 (SEQ ID NO:17), m100 (SEQ ID NO:9), m100_16H (SEQ ID NO:4), m100_44H (SEQ ID NO:11), m102 (SEQ ID NO:10), m102_16H (SEQ ID NO:5), or m102_44H (SEQ ID NO:12), and variants thereof, where a variant of one of the aforementioned mutant polypeptides is not another aforementioned mutant polypeptide, e.g. 1.10, 1.78, m28, m123, m100, m100_16H, m100_44H, m102, m102_16H, or m102_44H. It will be understood by the ordinarily skilled artisan that "mutants and variants thereof" as used herein do not encompass native EGF polypeptide. In other words, a variant of a mutant will not comprise the sequence of wild type EGF polypeptide.

Mutant EGF polypeptides of the invention have improved biological activities that allow them to function as agonists or antagonists of wild type EGF. By "biological activity" or more specifically "EGF-specific biological activity" it is meant a biological response elicited by wild-type EGF upon binding to the EGF receptor (EGFR). Accordingly, mutant EGF polypeptides of the present invention will bind to EGFR. Biological activities of wild type EGF polypeptide that may be improved in the subject mutants include, without limitation, modulating EGFR phosphorylation, modulating EGFR downregulation from the cellular surface, modulating EGFR degradation, modulating EGFR recycling, and modulating cellular responses associated with EGF/EGFR signaling, e.g. cell growth, cell proliferation, cell differentiation and cell migration. The terms "improved" or "enhanced" biological activity as used herein denote biological activity that is quantitatively different than the activity exhibited by the corresponding wild-type EGF polypeptide, e.g. 1.5-fold different or more, 2-fold different or more, 3-fold different or more, 4-fold different or more, 5-fold different or more, 7-fold different or more, 10-fold different or more, 20-fold different or more, 30-fold different or more, 40-fold different or more, or 50-fold different or more than the activity exhibited by wild-type EGF. For example, in some instances, the improvement in biological activity may be an increase in activity. In such instances, the improvement may be an increase in activity of 1.5-fold or more, 2-fold or more, 3-fold or more, 4-fold or more, 5-fold or more, 7-fold or more, 10-fold or more, 20-fold or more, 30-fold or more, 40-fold or more, or 50-fold or more than the activity exhibited by wild-type EGF. In other instances, the improvement in biological activity may be a decrease in activity. In such instances, the improvement may be a decrease in activity of 1.5-fold or more, 2-fold or more, 3-fold or more, 4-fold or more, 5-fold or more, 7-fold or more, 10-fold or more, 20-fold or more, 30-fold or more, 40-fold or more, or 50-fold or more than the activity exhibited by wild-type EGF.

In some aspects, the improvement in EGF-specific biological activities is correlated with a difference in the binding kinetics of the mutant EGF polypeptide relative to its parent, e.g. the wild type polypeptide, or a mutant polypeptide from which it was derived. By "binding kinetics" or "kinetic binding rates" it is generally meant the characteristics of the interaction between one molecule and another, e.g. a ligand to its cognate receptor, e.g. EGF to EGFR; for example, the affinity constant ($K_A$), the on-rate, the off-rate, etc. of binding. The specificity of interaction is a function of the binding constant $K_A=[LR]/[L][R]$, where [L], [R], and [LR] are the molar concentrations of the unbound ligand, the unbound receptor, and the bound receptor complex, respectively. The reciprocal of the $K_A$ is the equilibrium dissociation constant $K_D$. In other words, $K_D=[L][R]/[LR]$. The binding constant is related to the bimolecular on-rate ($k_{on}$) and the unimolecular off-rate ($k_{off}$) as $K_D=k_{off}/k_{on}$. To characterize the interaction, any of these parameters $K_A$, $K_D$, $k_{on}$, and $k_{off}$ may be measured using any convenient assay, e.g. as known in the art or as described below.

For example, in some embodiments, the subject mutant EGF polypeptides have an on-rate under physiological and/or acidic conditions that is different from that of the polypeptide upon which it was design (the "parent polypeptide", e.g. wild type EGF, or a mutant EGF polypeptide). By "on-rate", or "$k_{on}$", it is meant the speed at which the unbound ligand becomes bound to the receptor, typically measured in $M^{-1}s^{-1}$. In some embodiments, the mutant has an on-rate that is faster than the parent polypeptide, e.g. about 1.5-fold faster to about 100-fold faster, e.g. 1.5-fold faster or more, 2-fold faster or more, 3-fold faster or more, 4-fold faster or more, 5-fold faster or more, 7-fold faster or more, 10-fold faster or more, 20 fold faster or more, 40-fold faster or more, 60-fold faster or more, 80-fold faster or more, in some instances about 100-fold faster. In other embodiments, the mutant has an on-rate that is slower than that of the parent polypeptide, e.g. about 1.5-fold slower to about 100-fold slower, e.g. 1.5-fold slower or more, 2-fold slower or more, 3-fold slower or more, 4-fold slower or more, 5-fold slower or more, 7-fold slower or more, 10-fold slower or more, 20-fold slower or more, 40-fold slower or more, 60-fold slower or more, 80-fold slower or more, in some instances about 100-fold slower. In some embodiments, the mutant has an on-rate that is comparable to, i.e. substantially the same as or negligibly different from, the parent polypeptide.

As another example, in some embodiments, the subject mutant EGF polypeptides have an off-rate under physiological and/or acidic conditions that is different from that of the parent polypeptide upon which it was design. By "off-rate" is meant the speed at which bound receptor complex dissociates into unbound ligand and unbound receptor, or "$k_{off}$", typically measured in $s^{-1}$. In some embodiments, the mutant has an off-rate that is faster than the parent polypeptide, e.g. about 1.5-fold faster to about 100-fold faster than that of the parent polypeptide, e.g. 1.5-fold faster or more, 2-fold faster or more, 3-fold faster or more, 4-fold faster or more, 5-fold faster or more, 7-fold faster or more, 10-fold faster or more, 20-fold faster or more, 40-fold faster or more, 60-fold faster or more, 80-fold faster or more, in some instances about 100-fold faster. In other embodiments, the mutant has an off-rate that is slower than that of the parent polypeptide, e.g. about 1.5-fold slower to about 100-fold slower, e.g. 1.5-fold slower or more, 2-fold slower or more, 3-fold slower or more, 4-fold slower or more, 5-fold slower or more, 7-fold slower or more, 10-fold slower or more, 20-fold slower or more, 40-fold slower or more, 60-fold slower or more, 80-fold slower or more, in some instances about 100-fold slower. In some embodiments, the mutant has an off-rate that is comparable to, i.e. substantially the same as or negligibly different from, the parent polypeptide.

As another example, in some embodiments, the subject mutant EGF polypeptides bind EGFR under physiological and/or acidic conditions with an affinity that is different from that of the parent polypeptide upon which it was design. For example, in some embodiments, the affinity of the mutant EGF polypeptide for the EGFR is 2-fold greater or more, e.g. 3-fold greater or more, 4-fold greater or more, or 5-fold greater or more, sometimes 6-fold greater or more, e.g. 7-fold greater or more, 8-fold greater or more, 9-fold greater or more, or 10-fold greater or more, sometimes 15-fold greater or more, e.g. 20-fold greater or more, 30-fold greater or more, 40-fold greater or more, or 50-fold greater or more than that of the parent polypeptide. In other embodiments, the affinity of the mutant is decreased by 2-fold or more, e.g. 3-fold or more, 4-fold or more, or 5-fold or more, sometimes 6-fold or more, e.g. 7-fold or more, 8-fold or more, 9-fold or more, or 10-fold or more, sometimes 15-fold or more, e.g. 20-fold or more, 30-fold or more, 40-fold or more, or 50-fold or more relative to that of the parent polypeptide. In some embodiments, the mutant has an affinity that is comparable to, i.e. substantially the same as or negligibly different from, the parent polypeptide.

As mentioned above, in some instances, the binding kinetics are different in the mutant polypeptide versus the parent polypeptide under acidic conditions. In other words, in some embodiments, the mutant EGF polypeptides demonstrate an increased pH sensitivity to EGFR binding. In other words, the binding of the mutant EGF polypeptide to EGFR is more sensitive to pH than the parent polypeptide, in particular, at pHs less than about 7.5, more particularly at pHs less than about 7.0, more particularly at pHs less than about 6.5, more particularly at pHs less than about 6.0, more particularly at pHs within a range of from about 5.0 to about 6.0 pH units, in some instances at pHs within a range of from about 4.0 to about 5.0, in some instances at pHs within a range of from about 3.0 to about 4.0 as compared to the parent polypeptide.

In some embodiments, the mutant EGF polypeptide exhibits an improvement in one EGF-associated biological activity, for example, modulating the phosphorylation of EGFR, modulating the downregulation/degradation of EGFR, modulating cellular proliferation, modulating cellular migration, etc., e.g. a 2-fold modulation in activity or more, e.g. a 3-fold modulation or more, a 4-fold modulation or more, a 5-fold modulation or more, in some instances, a 6-fold modulation or more, a 7-fold modulation or more, an 8-fold modulation or more, a 9-fold modulation or more, sometimes a 10-fold modulation or more. The improvement in activity may be an increase or a decrease in activity, depending on the desired outcome. For example, it may be desirable to stabilize EGFR, i.e. decrease EGFR downregulation, e.g. so as to increase cellular proliferation. In such an instance, the improved biological activity would be a decrease in activity that promotes EGFR downregulation, and an increase in activity that promotes cellular proliferation. In some embodiments, the mutant EGF polypeptide exhibits an improvement in two or more biological activities, e.g. an increase in activity promoting EGFR phosphorylation, and an increase in activity promoting cellular migration. In some embodiment, the mutant EGF polypeptide exhibits an improvement in three or more biological activities, e.g. a decrease in activity promoting phosphorylation of EGFR, a decrease in activity promoting downregulation of EGFR, and an increase in activity promoting cellular proliferation. These activities may be measured by any convenient assay, e.g. western blotting, flow cytometry, EGF depletion studies, migration assays in cell culture, etc.

Typically, the subject mutant polypeptide will comprise one or more of the binding kinetics characteristics described above, e.g. an on-rate that is different under physiological and/or acidic conditions from wild type EGF, an off-rate that is different under physiological and/or acidic conditions from wild type EGF, an affinity that is different under physiological and/or acidic conditions from wild type EGF; and one or more of the improved biological activities described above. In some instances, a particular binding kinetics characteristic may correlate with a particular biological activity.

For example, and as demonstrated in working example 2 below, mutants comprising an off-rate at physiological and acidic pH that is faster than that of wild type EGF are observed to have less biological activity in promoting the phosphorylation of EGFR than wild type EGF, less biological activity in promoting the downregulation/degradation of EGFR than wild type EGF, less degradation of EGF ligand from the media, and an increase in biological activity in promoting cellular proliferation. In some instances, the mutant EGF polypeptide comprises a substitution in one or more residues of SEQ ID NO:1 selected from the group consisting of residues 3, 5, 8, 12, 23, 28, 38, 48, 49, and 51. See, e.g. mutant 38+49 (SEQ ID NO:20) and mutant 1.10 (SEQ ID NO:2), described in working examples 1 and 2, which comprise substitutions in residues 38 and 49; and mutant 1.78 (SEQ ID NO:3), also described in working examples 1 and 2, which comprises substitutions at residues 5, 8, 12, 23, 28, 38, 48 and 51. The subject mutant polypeptides encompass such mutants and variants thereof, e.g. polypeptides have a sequence identity of 80% or more, 85% or more, 90% or more, 95% or more, or 98% or more, that comprise these binding characteristics and improved biological features. Such variants may be readily identified using the assays described herein.

As another example, and as demonstrated in working example 3 below, mutants comprising an on-rate that is faster than that of wild type EGF and a binding affinity for EGFR at physiological and acidic pH that is stronger than that of wild type EGF are sometimes observed to have an increase in biological activity promoting EGFR phosphorylation and EGFR downregulation/degradation, and an increase in promoting cellular migration. In some instances, the mutant EGF polypeptide comprises a substitution in one or more residues of SEQ ID NO:1 selected from the group consisting of residues 3, 8, 10, 16, 17, 21, 24, 26, 28, 38, 48, 49, 51, and 52. See, e.g. m28 (SEQ ID NO:16), which comprises substitutions in residues 3, 17, 24, 26, 28, 48, 51 and 52; m123 (SEQ ID NO:17), which comprises substitutions in residues 3, 8, 10, 21, 28, 38, 48, 51, and 56; m100 (SEQ ID NO:9), which comprises substitutions in residues 3, 16, 21, 38, 48, and 49; and m102 (SEQ ID NO:10), which comprises substitutions in residues 1, 3, 16, 21, 28, 38, 45, and 51, all described in working example 3. The subject mutant polypeptides encompass such mutants and variants thereof, e.g. polypeptides have a sequence identity of 80% or more, 85% or more, 90% or more, 95% or more, or 98% or more to such variants, that comprise these binding characteristics and improved biological features.

As a third example, and as described in greater detail in working example 4 below, introduction of a histidine residue into an EGF polypeptide, e.g. at residue 16, correlates with an off-rate at physiological pH that is faster than that of its corresponding parent mutant EGF polypeptide and a binding affinity for EGFR under acidic conditions that is significantly weaker than that of its corresponding parent mutant EGF polypeptide. Despite the weaker binding affinity, these mutants promote more EGFR phosphorylation and less EGFR downregulation/degradation. The fact that EGF mutants having these biochemical characteristics exhibit increased biological activity is surprising in view of the art. See Mullenbach et al. ("Modification of a receptor-binding surface of epidermal growth factor (EGF): analogs with enhanced receptor affinity at low pH or at neutrality," Protein Engineering vol. II no. 6 pp. 473-480, incorporated herein in its entirety). In some instances, the mutant EGF polypeptide comprises a substitution in one or more residues of SEQ ID NO:1 selected from the group consisting of residues 1, 2, 3, 5, 8, 16, 17, 21, 24, 28, 38, 44, 45, 48, 49, 51, and 52, and comprises a histidine at residues 16 and/or 44. See, m100_16H (SEQ ID NO:4) and m100_44H (SEQ NO:11), which comprise substitutions in residues 3, 21, 38, 48, and 49 and a histidine at residue 16 or 44. See also, e.g. m102_16H (SEQ ID NO:5) and m102_44H (SEQ ID NO:12), which comprise substitutions in residues 1, 3, 24, 28, 38, 45, and 51 and a histidine at residue 16 or 44. The subject mutant polypeptides encompass such mutants and variants thereof, e.g. polypeptides have a sequence identity of 80% or more, 85% or more, 90% or more, 95% or more, or 98% or more to such mutants, that comprise these binding characteristics and improved biological features.

Variants having the above described biological activity/activities may be readily identified using the assays described herein. For example, variants may be identified as having a desirable biological activity by contacting a receptor or extracellular fragment thereof with the variant; assessing the binding kinetics, e.g. on-rate, off-rate, and/or affinity, of the variant; comparing the binding kinetics under physiological and/or acidic conditions of the variant to the binding kinetics of a control EGF polypeptide, and determining if the variant has the desired improved biological activity based on the comparison. For example, the EGFR binding off-rate may be assessed, where an increased off-rate relative to the wild type polypeptide indicates that the mutant EGF polypeptide has improved activity in promoting cell proliferation. As another example, the EGFR binding on-rate may be assessed, where an increased on-rate relative to the wild type polypeptide indicates that the mutant EGF polypeptide has improved activity in promoting cell migration.

Variants having the above described biological activity/activities may also be rationally engineered. For example, a mutant having an overall binding affinity that is greater than that exhibited by wild-type EGF may be identified, e.g. by methods known in the art [see e.g. Cochran et at., Protein Eng Des Sel (2006), 19(6): p 245-53]. Next, amino acid substitutions which do not change EGFR binding on-rates at physiological pH but increase EGFR binding off-rate (and consequent decrease overall binding affinity) at physiological pH and decrease binding affinity at acidic pH in particular, at pHs less than about 7.5, more particularly at pHs less than about 7.0, more particularly at pHs less than about 6.5, more particularly at pHs less than about 6.0, more particularly at pHs within a range of from about 5.0 to about 6.0 pH units, as compared to wild-type EGF, are identified, and the original mutants are modified by any of a number of directed mutagenesis methods that are well-known in the art to comprise these mutations. The resulting mutants are expected to have increased biological activity in promoting EGFR phosphorylation and less biological activity in promoting the downregulation/degradation of EGFR than wild type EGF. In some embodiments, the amino acid introduced is a histidine. In some embodiments, the residue that is substituted is residue 16. Substituting a histidine residue at position 16 to arrive at mutant EGF polypeptides having the biochemical properties and biological activities of the EGF mutants of the present invention is an approach that is taught away from by the art [see e.g. Mullenbach et at., Protein Engineering vol. II no. 6 pp. 473-480]. Mullenbach et al. instead teaches replacing the 16H residue with alanine or aspartic acid in order to enhance therapeutic effects in low pH environments, and hence teaches away from modifications which increase pH sensitivity at low pH.

The subject mutant EGF polypeptides may be prepared by traditional chemical synthetic means, by recombinant means, or by a combination of both methods. For example, the polypeptides can be produced in eukaryotic organisms or synthesized in E. coli or other prokaryotes in the event the polypeptide is a chimera (that includes, in addition to the mutant EGF, for example, a label or tag), it can be encoded by a hybrid nucleic acid molecule containing one sequence that encodes the mutant EGF and a second sequence that encodes a second polypeptide. For example, the mutant EGF polypeptide may be fused to a hexa-histidine tag to facilitate purification of bacterially expressed protein, or to a hemagglutinin tag to facilitate purification of protein expressed in eukaryotic cells.

The techniques that are required to make mutant EGF polypeptides are routine in the art, and can be performed without resort to undue experimentation by one of ordinary skill in the art. For example, a mutation that consists of a substitution of one or more of the amino acid residues in EGF (e.g., a human EGF) can be created using a PCR-assisted mutagenesis technique (e.g., as known in the art and/or described herein). Mutations that consist of deletions or additions of amino acid residues to an EGF polypeptide can also be made with standard recombinant techniques. In the event of a deletion or addition, the nucleic acid molecule encoding EGF can simply be digested with an appropriate restriction endonuclease. The resulting fragment can either be expressed directly or manipulated further by, for example, ligating it to a second fragment. The ligation may be facilitated if the two ends of the nucleic acid molecules contain complementary nucleotides that overlap one another, but blunt-ended fragments can also be ligated.

As noted above, the mutant EGF polypeptides can also be prepared as fusion or chimeric polypeptides that include a mutant EGF polypeptide and a heterologous polypeptide (i.e., a polypeptide that is not EGF or a mutant thereof) as described, for example, in U.S. Pat. No. 6,451,308. The heterologous polypeptide can serve any desired function. For example, it can increase the circulating half-life of the chimeric polypeptide in vivo. The polypeptide that increases the circulating half-life may be a serum albumin, such as human serum albumin, or the Fc region of the IgG subclass of antibodies. The Fc region can include a mutation that inhibits complement fixation and Fc receptor binding, or it may be lytic (i.e., able to bind complement or to lyse cells via another mechanism, such as antibody-dependent complement lysis (ADCC; see, e.g., Morrison et al., The Immunologist 2:119-124, 1994; and Brekke et al., The Immunologist 2:125, 1994). The Fc region can be a naturally occurring or synthetic polypeptide that is homologous to the IgG C-terminal domain produced by digestion of IgG with papain. The mutant EGF polypeptides can include the entire Fc region, or a smaller portion that retains the ability to extend the circulating half-life of a chimeric polypeptide of which it is a part. In addition, full-length or fragmented Fc regions can be variants of the wild-type molecule. That is, they can contain mutations that may or may not affect the function of the polypeptides; as described further below, native activity is not necessary or desired in all cases.

In other embodiments, the chimeric polypeptide can include the mutant EGF polypeptide and a polypeptide that functions as an antigenic tag, such as a FLAG sequence. FLAG sequences are recognized by biotinylated, highly specific, anti-FLAG antibodies, as described herein (see also Blanar at al., Science 256:1014, 1992: LeClair et al., Proc. Natl. Acad. Sci. USA 89:8145, 1992). In some embodiments, the chimeric polypeptide further comprises a C-terminal c-myc epitope tag. Any other polypeptide used in the art to facilitate purification, to identify or localize a binding site, or to lyse or otherwise inhibit the activity of a cell can be fused or otherwise joined (e.g., chemically conjugated) to a mutant EGF (e.g., a mutant human EGF). In other embodiments, the chimeric polypeptide includes the mutant EGF and a polypeptide that functions to enhance expression or direct cellular localization of the mutant EGF polypeptide, such as the Aga2p agglutinin subunit (see, e.g., Boder and Wittrup, Nature Biotechnol. 15:553-7, 1997), which is incorporated herein by reference in its entirety.

Mutant EGF polypeptides may optionally be fused to a polypeptide domain that increases solubility of the product. The domain may be linked to the polypeptide through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, GRPE domain, and the like. The polypeptide may be formulated for improved stability or blood circulation times. For example, the peptides may be PEGylated, where the polyethyleneoxy group provides for enhanced lifetime in the blood stream.

The mutant EGF polypeptide(s) may be produced by eukaryotic cells or by prokaryotic cells, it may be further processed by unfolding, e.g. heat denaturation, DTT reduction, etc. and may be further refolded, using methods known in the art. Modifications of interest that do not alter primary sequence include chemical derivatization of polypeptides, e.g., acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also included in the subject invention are mutant EGF polypeptide(s) that have been modified using ordinary molecular biological techniques and synthetic chemistry so as to improve their resistance to proteolytic degradation or to optimize solubility properties or to render them more suitable as a therapeutic agent. Analogs of such polypeptides include those containing residues other than naturally occurring L-amino acids, e.g. D-amino acids or non-naturally occurring synthetic amino acids. D-amino acids may be substituted for some or all of the amino acid residues.

The mutant EGF polypeptide(s) may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The mutant EGF polypeptide(s) may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

A mutant EGF polypeptide, either alone or as a part of a chimeric polypeptide, such as those described above, can be obtained by expression of a nucleic acid molecule; such nucleic acid molecules are within the scope of the invention. Just as mutant EGF polypeptides can be described in terms of their identity to wild-type EGF polypeptides, the nucleic add molecules encoding them will necessarily have a certain identity with those that encode wild-type EGF. For example, the nucleic acid molecule encoding a mutant EGF polypeptide can be at least 65%, at least 75%, at least 85%, or at least 95% (e.g., 99%) identical to the nucleic acid encoding wild-type EGF (e.g., SEQ ID NO:1). For nucleic acids, the length of the sequences compared will generally be at least or about 110 nucleotides (e.g., at least or about 130 nucleotides, 150 nucleotides, or 159 nucleotides).

The nucleic acid molecules of the invention can vary but, due to the degeneracy of the genetic code, encode the same mutant EGF. The nucleic acid molecules can consist of RNA or DNA (for example, genomic DNA, cDNA, or synthetic DNA, such as that produced by phosphoramidite-based synthesis), or combinations or modifications of the nucleotides within these types of nucleic acids. In addition, the nucleic acid molecules can be double-stranded or single-stranded (i.e., either a sense or en antisense strand).

The nucleic acid molecules of the invention may be referred to as "isolated" when they are within, for example, an expression vector (e.g., a plasmid or viral vector). The nucleic acids, whether within an expression vector or not, can also include some or all of the non-coding sequences that lies upstream or downstream from a sequence that naturally encodes EGF. For example, the mutant EGF nucleic acids of the invention can be operably linked to regulatory sequences (such as a promoter or enhancer) that normally influence the expression of a wild-type EGF. Those of ordinary skill in the art of molecular biology are familiar with routine procedures for isolating or otherwise producing nucleic acid molecules. They can, for example, be generated by treatment of genomic DNA with restriction endonucleases, or by performance of the polymerase chain reaction (PCR). In the event the nucleic acid molecule is a ribonucleic acid (RNA), molecules can be produced, for example, by in vitro transcription. Naturally occurring sequences can then be mutated (by, for example, the procedures described here) to produce the mutant EGF polypeptides of the invention. The nucleic acid molecules of the invention can be obtained by introducing a mutation into EGF-encoding DNA obtained from any biological cell, such as the cell of a mammal. Thus, the nucleic acids of the invention can be those of a mouse, rat, guinea pig, cow, sheep, horse, pig, rabbit, monkey, baboon, dog, or cat. Typically, the nucleic acid molecules will be those of a human.

As described above, the mutant EGF polypeptide of the invention may exist as a part of a chimeric polypeptide. Accordingly, a nucleic acid molecule of the invention can contain sequences encoding the heterologous polypeptide (e.g., the "marker" or "reporter"). Examples of marker or reporter genes include beta-lactamase, chloramphenicol acetyltransferase (CAT), adenosine deaminase (ADA), aminoglycoside phosphotransferase (neo$^r$: G418$^r$), dihydrofolate reductase (DHFR), hygromycin-B-hosphotransferase (HPH), thymidine kinase (TK), lacz (encoding beta-galactosidase), and xanthine guanine phosphoribosyltransferase (XGPRT). As with many of the standard procedures associated with the practice of the invention, skilled artisans will be aware of additional useful reagents, for example, of additional sequences that can serve the function of a marker or reporter.

The nucleic acid molecules encoding the subject mutant EGF polypeptide may be contained within a vector that is capable of directing their expression in, for example, a cell that has been transduced with the vector. Accordingly, in addition to mutant EGF polypeptides, expression vectors containing a nucleic acid molecule encoding a mutant EGF polypeptide cells transfected with these vectors are within the scope of the invention.

Vectors suitable for use in the present invention include T7-based vectors for use in bacteria (see, for example, Rosenberg et al., Gene 56:125, 1987), the pMSXND expression vector for use in mammalian cells (Lee and Nathans, J. Biol. Chem. 263:3521, 1988), and baculovirus-derived vectors (for example the expression vector pBacPAK9 from Clontech, Palo Alto, Calif.) for use in insect cells. The nucleic acid inserts, which encode the polypeptide of interest in such vectors, can be operably linked to a promoter, which is selected based on, for example, the cell type in which expression is sought. For example, a T7 promoter can be used in bacteria, a polyhedrin promoter can be used in insect cells, and a cytomegalovirus or metallothionein promoter can be used in mammalian cells. Also, in the case of higher eukaryotes, tissue-specific and cell type-specific promoters are widely available. These promoters are so named for their ability to direct expression of a nucleic acid molecule in a given tissue or cell type within the body. Skilled artisans are well aware of numerous promoters and other regulatory elements which can be used to direct expression of nucleic acids.

In addition to sequences that facilitate transcription of the inserted nucleic acid molecule, vectors can contain origins of replication, and other genes that encode a selectable marker. For example, the neomycin-resistance (neo.sup.r) gene imparts G418 resistance to cells in which it is expressed, and thus permits phenotypic selection of the transfected cells. Those of skill in the art can readily determine whether a given regulatory element or selectable marker is suitable for use in a particular experimental context.

Viral vectors that can be used in the invention include, for example, retroviral, adenoviral, and adeno-associated vectors, herpes virus, simian virus 40 (SV40), and bovine papilloma virus vectors (see, for example, Gluzman (Ed.), Eukaryotic Viral Vectors, CSH Laboratory Press, Cold Spring Harbor, N.Y.).

Prokaryotic or eukaryotic cells that contain and express a nucleic acid molecule that encodes a mutant EGF polypeptide are also features of the invention. A cell of the invention is a transfected cell, i.e., a cell into which a nucleic acid molecule, for example a nucleic acid molecule encoding a mutant EGF polypeptide, has been introduced by means of recombinant DNA techniques. The progeny of such a cell are also considered within the scope of the invention.

The precise components of the expression system are not critical. For example, a mutant EGF polypeptide can be produced in a prokaryotic host, such as the bacterium *E. coli*, or in a eukaryotic host, such as an insect cell (e.g., an Sf21 cell), or mammalian cells (e.g., COS cells, NIH 3T3 cells, or HeLa cells). These cells are available from many sources, including the American Type Culture Collection (Manassas, Va.). In selecting an expression system, it matters only that the components are compatible with one another. Artisans or ordinary skill are able to make such a determination. Furthermore, if guidance is required in selecting an expression system, skilled artisans may consult Ausubel et al. (Current Protocols in Molecular Biology, John Wiley and Sons, New York, N.Y., 1993) and Pouwels et al. (Cloning Vectors: A Laboratory Manual, 1985 Suppl. 1987). The expressed polypeptides can be purified from the expression system using routine biochemical procedures, and can be used, e.g., as therapeutic agents, as described herein.

Methods of Use

In general, the mutant EGF polypeptides and nucleic acids of the subject invention may be used in any instance in which it is desirable to modulate EGFR signaling. As such, the subject mutant EGF polypeptides find use in any application in which EGFR-directed regulation of cell growth and activity is desired.

For example, EGFR receptor signaling has been extensively investigated in normal and pathological wound healing. EGFR receptor signaling has been implicated in keratinocyte migration, corneal epithelial cell migration, fibroblast function and the formation of granulation tissue. As another example, EGFR receptor signaling has been shown to promote the survival and proliferation of stem cells, e.g. neural stem cells (Tropepe, V et al. (1999) Dev Biol. 208(1):166-88), mesenchymal stem cells (Marcantonio N A et al. (2009) Biomaterials 30(27):4629-38), intestinal stem cells (Biteau et al. (2011) Development 138:1045-1055), and pancreatic beta-cells (Miettinen P, et al. Biochem Soc Trans 2008 36:280-285). As such, the subject mutant polypeptides and nucleic acids find use in the treatment of acute and chronic wounds and lesions, e.g. gastric or oral ulcers (Fujisawa, et al. J Oral Pathol Med 32:358-366, 2003), foot ulcers (e.g., diabetes-associated), corneal epithelial wounds, epidermal lesions, tympanic membrane perforations (Ma et al., Acta Otolaryngol. 122(6):586-99, 2002), necrotizing enterocolitis, and the like, and in the field of regenerative medicine, to promote ex vivo or in vivo survival and expansion of stem cells, i.e. pluripotent stem cells, tissue specific stem cells, or progenitor cells, which cells may then be differentiated ex vivo or in vivo into desired cell types to replace lost, damaged, or defective cells, e.g. following brain or spinal cord injury (Xian et al., Mol Neurobiol. 20(2-3):157-83, 1999), radiation, chemotherapy, ischemic or inflammatory insult, etc. or in disease, e.g. diabetes, neurodegenerative disease, gastrointestinal disorders, etc.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease. The terms "individual," "subject," "host," and "patient," are used interchangeably herein and refer to any mammalian subject for whom diagnosis, treatment, or therapy is desired, particularly humans.

In Vitro Applications

In some applications, the mutant EGF polypeptide is employed to modulate EGFR signaling in vitro, e.g. for research purposes, or ex vivo, e.g. to modify cells that may be returned to an individual. The subject methods may be used to modulate EGFR signaling activity in any cell that expresses EGFR. Cells of interest include pluripotent stem cells, e.g. ES cells, iPS cells, and embryonic germ cells; and somatic cells, e.g. fibroblasts, hematopoietic cells, neurons, muscle cells, bone cells, vascular endothelial cells, gut cells, and the like, and their lineage-restricted progenitors and precursors. Cells may be from any mammalian species, e.g. murine, rodent, canine, feline, equine, bovine, ovine, primate, human, etc. Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. Typically, the primary cell lines of the present invention are maintained for fewer than 10 passages in vitro.

If the cells are primary cells, they may be harvest from an individual by any convenient method. For example, cells, e.g. blood cells, e.g. leukocytes, may be harvested by apheresis, leukocytapheresis, density gradient separation, etc. As another example, cells, e.g. skin, muscle, bone marrow, spleen, liver, pancreas, lung, intestine, stomach tissue, etc. may be harvested by biopsy. An appropriate solution may be used for dispersion or suspension of the harvested cells. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc. The cells may be used immediately, or they may be stored, frozen, for long periods of time, being thawed and capable of being reused. In such cases, the cells will usually be frozen in 10% DMSO, 50% serum, 40% buffered medium, or some other such solution as is commonly used in the art to preserve cells at such freezing temperatures, and thawed in a manner as commonly known in the art for thawing frozen cultured cells.

To modulate EGFR signaling, the mutant EGF polypeptide(s)—be they polypeptides or nucleic acids that encode mutant EGF polypeptides—are provided to the cells for about 30 minutes to about 24 hours, e.g., 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours, which may be repeated with a frequency of about every day to about every 4 days, e.g., every 1.5 days, every 2 days, every 3 days, or any other frequency from about every day to about every four days. The agent(s) may be provided to the subject cells one or more times, e.g. one time, twice, three times, or more than three times, and the cells allowed to incubate with the agent(s) for some amount of time following each contacting event e.g. 16-24 hours, after which time the media is replaced with fresh media and the cells are cultured further.

In cases in which two or more different mutant EGF polypeptides are provided to the cell, i.e. a mutant EGF polypeptide cocktail, the mutant EGF polypeptides may be provided simultaneously, e.g. as two polypeptides delivered simultaneously, as two nucleic acid vectors delivered simultaneously, or as a single nucleic acid vector comprising the coding sequences for both fusion polypeptides. Alternatively, they may be provided consecutively, e.g. the first mutant EGF polypeptides being provided first, followed by the second mutant EGF polypeptide, etc. or vice versa.

The subject mutant EGF polypeptide is typically provided to cells in an effective amount, i.e. an amount that is effective to modulate EGFR signaling and hence, cellular activity. Biochemically speaking, an effective amount or effective dose of a mutant EGF polypeptide is an amount necessary to alter EGFR signaling in a cell by 30% or more, 40% or more, 50% or more, 60% or more, 70% or more, 80% or more, 90% or more, 100% or more, 200% or more, or 500% or more. Put another way, EGFR signaling will be altered about 0.5-fold or more, 1-fold or more, 2-fold or more, 5-fold or more, 8-fold or more, or 10-fold or more. The extent to which EGFR signaling is modulated by a mutant EGF polypeptide can be readily determined by a number of ways known to one of ordinary skill in the art of molecular biology. For example, changes in the level of phosphorylation of EGFR may be measured by, e.g. Western blotting. Downregulation of EGFR on the surface of the cell may be measured by, e.g., EGF and EGFR depletion studies. Cellular proliferation may be measured by, e.g., BrdU labeling. Cellular migration maybe measured e.g. in Boyden chamber studies in vitro or wound healing in vivo. In these ways, the modulatory effect of the mutant polypeptide may be confirmed.

Contacting the cells with the mutant EGF polypeptide(s) may occur in any culture media and under any culture conditions that promote the survival of the cells. For example, cells may be suspended in any appropriate nutrient medium that is convenient, such as Iscove's modified DMEM or RPMI 1640, supplemented with fetal calf serum or heat inactivated goat serum (about 5-10%), L-glutamine, a thiol, particularly 2-mercaptoethanol, and antibiotics, e.g. penicillin and streptomycin. The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors. The mutant EGF polypeptide may be provided in addition to other agents that modulate EGFR signaling. The mutant EGF polypeptide may be provided in addition to other agents that modulate the activity of other signaling pathways.

Cells that have been contacted with mutant EGF polypeptides in vitro have a number of uses. For example, the cells may be used for biological research, e.g. to better understand EGFR signaling, or in screens for the discovery of novel agents to treat disease. As another example, the cells may be transplanted to a subject for purposes such as to accelerate regeneration of tissues, e.g. in wound healing, or for gene therapy, e.g. as described below. The subject may be a neonate, a juvenile, or an adult. Of particular interest are mammalian subjects. Mammalian species that may be treated with the present methods include canines and felines; equines; bovines, ovines; etc. and primates, particularly humans. Animal models, particularly small mammals, e.g. murine, lagomorpha, etc. may be used for experimental investigations.

If the cells are to be transplanted to an individual, they may be provided to the subject alone or with a suitable substrate or matrix, e.g. to support their growth and/or organization in the tissue to which they are being transplanted. Usually, at least $1 \times 10^3$ cells will be administered, for example $5 \times 10^3$ cells, $1 \times 10^4$ cells, $5 \times 10^4$ cells, $1 \times 10^5$ cells, $1 \times 10^6$ cells or more. The cells may be introduced to the subject via any of the following routes: topical, parenteral, subcutaneous, intravenous, intracranial, intraspinal, intraocular, or into spinal fluid. The cells may be introduced by injection, catheter, or the like. Examples of methods for local delivery, that is, delivery to the site of injury, include, e.g. through an Ommaya reservoir, e.g. for intrathecal delivery (see e.g. U.S. Pat. Nos. 5,222,982 and 5,385,582, incorporated herein by reference); by bolus injection, e.g. by a syringe, e.g. into a joint; by continuous infusion, e.g. by cannulation, e.g. with convection (see e.g. US Application No. 20070254842, incorporated here by reference); or by implanting a device upon which the cells have been reversibly affixed (see e.g. US Application Nos. 20080081064 and 20090196903, incorporated herein by reference).

The number of administrations of treatment to a subject may vary. Introducing the genetically modified cells into the subject may be a one-time event; but in certain situations, such treatment may elicit improvement for a limited period of time and require an on-going series of repeated treatments. In other situations, multiple administrations of the genetically modified cells may be required before an effect is observed. The exact protocols depend upon the disease or condition, the stage of the disease and parameters of the individual subject being treated.

In Vivo Applications

The subject methods may also be used to modulate EGFR signaling in vivo, for example to promote cell proliferation, e.g. in tissue regeneration, or cell migration, e.g. in wound healing. In these in vivo embodiments, the mutant EGF polypeptide is administered directly to the individual. A mutant EGF polypeptide may be administered by any of a number of well-known methods in the art and described below for the administration of peptides and polypeptides to a subject. The mutant EGF polypeptide may be provided in addition to other agents that modulate EGFR signaling. The mutant EGF polypeptide may be provided in addition to other agents that modulate the activity of other signaling pathways.

As discussed above, the mutant EGF polypeptide is typically administered in an effective amount. The amount administered varies depending upon the goal of the administration, the health and physical condition of the individual to be treated, age, the taxonomic group of individual to be treated (e.g., human, non-human primate, primate, etc.), the degree of resolution desired, the formulation of the mutant EGF polypeptide composition, the treating clinician's assessment of the medical situation, and other relevant factors. It is expected that the amount will fall in a relatively broad range that can be determined through routine trials. For example, the amount of mutant EGF polypeptide employed to modulate EGFR signaling is not more than about the amount that could otherwise be irreversibly toxic to the subject (i.e., maximum tolerated dose). In other cases the amount is around or even well below the toxic threshold, but still in an immunoeffective concentration range, or even as low as threshold dose.

Calculating the effective amount or effective dose of mutant EGF polypeptide to be administered is within the skill of one of ordinary skill in the art, and will be routine to those persons skilled in the art. Needless to say, the final amount to be administered will be dependent upon a variety of factors, include the route of administration, the nature of the disorder or condition that is to be treated, and factors that will differ from patient to patient. A competent clinician will be able to determine an effective amount of a therapeutic agent to administer to a patient to halt or reverse the progression the disease condition as required. Utilizing $LD_{50}$ animal data, and other information available for the agent, a clinician can determine the maximum safe dose for an individual, depending on the route of administration. For instance, an intravenously administered dose may be more than an intrathecally or topically administered dose, given the greater body of fluid into which the therapeutic composition is being administered. Similarly, compositions which are rapidly cleared from the body may be administered at higher doses, or in repeated doses, in order to maintain a therapeutic concentration. Utilizing ordinary skill, the competent clinician will be able to optimize the dosage of a particular therapeutic in the course of routine clinical trials.

Individual doses are typically not less than an amount required to produce a measurable effect on the subject, and may be determined based on the pharmacokinetics and pharmacology for absorption, distribution, metabolism, and excretion ("ADME") of the mutant EGF polypeptide or of its by-products, and thus based on the disposition of the composition within the subject. This includes consideration of the route of administration as well as dosage amount, which can be adjusted for topical (applied directly where action is desired for mainly a local effect), enteral (applied via digestive tract for systemic or local effects when retained in part of the digestive tract), or parenteral (applied by routes other than the digestive tract for systemic or local effects) applications. For instance, administration of the mutant EGF polypeptide may be via injection, e.g. intravenous, intramuscular, or intrapancreatic injection, or a combination thereof.

The mutant EGF polypeptide may be administered by infusion or by local injection, e.g. by infusion at a rate of about 50 mg/h to about 400 mg/h, including about 75 mg/h to about 375 mg/h, about 100 mg/h to about 350 mg/h, about 150 mg/h to about 350 mg/h, about 200 mg/h to about 300 mg/h, about 225 mg/h to about 275 mg/h. Exemplary rates of infusion can achieve a desired therapeutic dose of, for example, about 0.5 $mg/m^2$/day to about 10 $mg/m^2$/day, including about 1 $mg/m^2$/day to about 9 $mg/m^2$/day, about 2 $mg/m^2$/day to about 8 $mg/m^2$/day, about 3 $mg/m^2$/day to about 7 $mg/m^2$/day, about 4 $mg/m^2$/day to about 6 $mg/m^2$/day, about 4.5 $mg/m^2$/day to about 5.5 $mg/m^2$/day. Administration (e.g. by infusion) can be repeated over a desired period, e.g., repeated over a period of about 1 day to about 5 days or once every several days, for example, about five days, over about 1 month, about 2 months, etc. It also can be administered prior, at the time of, or after other therapeutic interventions, such as surgical intervention to repair tissue, e.g. in the case of injury. The mutant EGF polypeptide can also be administered as part of a combination therapy, in which at least one of an immunotherapy, a diabetes therapy, a cancer therapy, etc. also is administered to the subject (as described in greater detail below).

Disposition of the mutant EGF polypeptide and its corresponding biological activity within a subject is typically gauged against the fraction of mutant EGF polypeptide present at a target of interest. For example, a mutant EGF polypeptide once administered can accumulate with a glycoconjugate or other biological target that concentrates the material in cancer cells and cancerous tissue. Thus dosing regimens in which the mutant EGF polypeptide is administered so as to accumulate in a target of interest over time can be part of a strategy to allow for lower individual doses. This can also mean that, for example, the dose of mutant EGF polypeptide that are cleared more slowly in vivo can be lowered relative to the effective concentration calculated from in vitro assays (e.g., effective amount in vitro approximates mM concentration, versus less than mM concentrations in vivo).

As an example, the effective amount can be gauged from the $EC_{50}$ of a given mutant EGF polypeptide concentration. By "$EC_{50}$" is intended the plasma concentration required for obtaining 50% of a maximum effect in vivo. In related embodiments, dosage may also be determined based on $ED_{50}$ (effective dosage). In general, with respect to the mutant EGF polypeptides of the present disclosure, an effective amount is usually not more than 100× the calculated $EC_{50}$. For instance, the amount of a mutant EGF polypeptide that is administered is less than about 100×, less than about 50×, less than about 40×, 35×, 30×, or 25× and many embodiments less than about 20×, less than about 15× and even less than about 10×, 9×, 9×, 7×, 6×, 5×, 4×, 3×, 2× or 1× than the calculated $EC_{50}$. The effective amount may be about 1× to 30× of the calculated $EC_{50}$, and sometimes about 1× to 20×, or about 1× to 10× of the calculated $EC_{50}$. The effective amount may also be the same as the calculated $EC_{50}$ or more than the calculated $EC_{50}$. The $EC_{50}$ can be calculated by modulating EGFR activity or cellular activity in vitro. The procedure can be carried out by methods known in the art or as described in the examples below.

Effective amounts of dose and/or dose regimen can readily be determined empirically from assays, from safety and escalation and dose range trials, individual clinician-patient relationships, as well as in vitro and in vivo assays such as those described herein and known in the art. For example, if a concentration used for carrying out the subject method in mice ranges from about 1 mg/kg to about 25 mg/kg based on the body weight of the mice, an example of a concentration of the mutant EGF polypeptide that can be employed in human may range about 0.083 mg/kg to about 2.08 mg/kg. Other dosage may be determined from experiments with animal models using methods known in the art (Reagan-Shaw et al. (2007) *The FASEB Journal* 22:659-661).

The mutant EGF polypeptide can be incorporated into a variety of formulations. More particularly, mutant EGF polypeptide may be formulated into pharmaceutical compositions by combination with appropriate pharmaceutically acceptable carriers or diluents. Pharmaceutical preparations are compositions that include one or more mutant EGF polypeptide present in a pharmaceutically acceptable vehicle. "Pharmaceutically acceptable vehicles" may be vehicles approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which a compound of the invention is formulated for administration to a mammal. Such pharmaceutical vehicles can be lipids, e.g. liposomes, e.g. liposome dendrimers; liquids, such as water and oils, including those of petroleum, animal, vegetable or synthetic origin, such as peanut oil, soybean oil, mineral oil, sesame oil and the like, saline; gum acacia, gelatin, starch paste, talc, keratin, colloidal silica, urea, and the like. In addition, auxiliary, stabilizing, thickening, lubricating and coloring agents may be used.

Pharmaceutical compositions may be formulated into preparations in solid, semi-solid, liquid or gaseous forms, such as tablets, capsules, powders, granules, ointments, solutions, suppositories, injections, inhalants, gels, microspheres, and aerosols. As such, administration of the mutant EGF polypeptide can be achieved in various ways, including transdermal, intradermal, oral, buccal, rectal, parenteral, intraperitoneal, intradermal, intracheal, etc., administration. The active agent may be systemic after administration or may be localized by the use of regional administration, intramural administration, or use of an implant that acts to retain the active dose at the site of implantation. The active agent may be formulated for immediate activity or it may be formulated for sustained release.

For inclusion in a medicament, the mutant EGF polypeptide may be obtained from a suitable commercial source. As a general proposition, the total pharmaceutically effective amount of the mutant EGF polypeptide administered parenterally per dose will be in a range that can be measured by a dose response curve.

Mutant EGF polypeptide therapies, i.e. preparations of mutant EGF polypeptide(s) to be used for therapeutic administration, may be sterile. Sterility is readily accomplished by filtration through sterile filtration membranes (e.g., 0.2 µm membranes). Therapeutic compositions generally are placed into a container having a sterile access port, for example, an intravenous solution bag or vial having a stopper pierceable by a hypodermic injection needle. The mutant EGF polypeptide-based therapies may be stored in unit or multi-dose containers, for example, sealed ampules or vials, as an aqueous solution or as a lyophilized formulation for reconstitution. As an example of a lyophilized formulation, 10-mL vials are filled with 5 ml of sterile-filtered 1% (w/v) aqueous solution of compound, and the resulting mixture is lyophilized. The infusion solution is prepared by reconstituting the lyophilized compound using bacteriostatic Water-for-Injection. Alternatively, the mutant EGF polypeptide may be formulated into lotions for topical administration.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The nucleic acids or polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249:1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Therapies that exhibit large therapeutic indices are preferred.

The data obtained from cell culture and/or animal studies can be used in formulating a range of dosages for humans. The dosage of the active ingredient typically lines within a range of circulating concentrations that include the ED50 with low toxicity. The dosage can vary within this range depending upon the dosage form employed and the route of administration utilized. The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

Screening Methods

In some aspects the invention encompasses screening methods for identifying mutant EGF polypeptides with improved biological activity. To that end, it has been shown that certain characteristic binding kinetics at physiological or acidic pH, e.g. faster or slower on-rate of binding to EGFR, faster or slower off-rate of binding to EGFR, weaker or stronger affinity to EGFR, correlate with improved biological activity, e.g. modified activity in promoting EGFR phosphorylation, modified activity in promoting EGFR downregulation from the cell surface, modified activity in promoting cellular proliferation, modified activity in promoting cellular migration and invasion, and the like. Accordingly, screening mutant EGF polypeptides for mutants with altered binding kinetics should identify mutants that will be useful in promoting cellular activity in the body, which may in turn be used to treat disease.

Additionally, novel systems such as cell-free protein synthesis systems and efficient methods of determining protein concentrations are disclosed herein which remove long-standing, previously intractable technical barriers which previously prohibited the use of cell-based assays for screening purposes. As such, using the systems and methods disclosed herein, it becomes possible to screen mutant EGF polypeptides directly for those having improved biological activity, e.g. in promoting EGFR phosphorylation, promoting down-regulation of EGFR from the cell surface, or in promoting cellular responses including, for example, proliferation, migration or invasion, so as to identify mutants that will be useful in promoting cellular activity in the body so as to treat disease.

For example, a method for identifying a mutant EGF polypeptide having improved biological activity may comprise contacting a receptor or extracellular fragment thereof with a mutant EGF polypeptide, assessing one or more parameters of the mutant EGF polypeptide to the EGF receptor or fragment thereof, comparing the one or more parameters of the mutant EGF polypeptide to the one or more parameters of a control EGF polypeptide, and identifying a mutant. EGF polypeptide having improved biological activity based on the comparison.

Cellular parameters are quantifiable components of cells, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values.

As will be readily apparent to the ordinarily skilled artisan, a number of output cellular parameters may be quantified when screening mutant EGF polypeptides for those with improved biological activity. For example, one or more parameters pertaining to the kinetics of EGF-EGFR binding may be measured, e.g. the on-rate, the off-rate, the affinity, e.g. a physiological or acidic pH. As another example, a biological activity may be measured, for example, the amount/degree of phosphorylation of the EGFR, e.g. by Western blotting; the amount of EGFR on the cell surface, e.g. by depletion studies; the amount of cell proliferation, e.g. by BrdU incorporation; the amount of cell migration; e.g. by tissue-culture based assays; etc. As yet another example, the expression of a reporter downstream of EGFR, i.e. a reporter operably linked to a promoter whose activity is regulated by EGFR signaling, may be measured. Any convenient parameter that reflects the binding kinetics or biological activity of EGF may be measured. In some instances, multiple parameters are measured.

The screens may comprise a cell-free assay. In other words, the EGFR or fragment thereof that is contacted by the mutant EGF polypeptide is an isolated EGFR polypeptide, e.g. suspended in solution or bound to a substrate, e.g. plate, column, or bead, e.g. surface plasmon resonance (SPA) bead. Additionally or alternatively, the screen may comprise a cell-based assay. In other words, the EGFR or fragment thereof that is contacted by the mutant EGF polypeptide is expressed by a cell, and the cell is contacted with the mutant EGF polypeptide.

In some embodiments, the mutant EGF polypeptides that are assessed are rationally engineered, i.e. by directed mutation. In other embodiments, the source of mutant EGF polypeptides to be tested is a library. Any convenient library of mutant EGF polypeptides may be used. One example is a library prepared from a DNA library by random mutagenesis. Any mutagenesis technique can be used to introduce diversity into a gene of interest, and the cell-free platform offers the convenience of using linear DNA templates, thereby avoiding the need for cloning into plasmids. The only requirement is the addition of T7 RNA polymerase promoter and terminator elements, which can be easily appended onto mutated genes by PCR assembly [Woodrow, K. A., 1.0. Airen, and J. R. Swartz, J Proteome Res, 2006. 5(12): p. 3288-300]. Single molecule PCR (SM-PCR) is then used to amplify the single DNA molecules to provide sufficient template for protein expression. After SM-PCR, a fluorescent dye is used to easily detect the presence of DNA template in the 96-well plates. The DNA template in each well of the microtiter plates is then translated into protein by oxidizing CFPS [Goerke, A. R. and J. R. Swartz, Biotechnol Bioeng, 2008. 99(2): p. 351-67., Yin, G. and J. R. Swartz, Biotechnology and Bioengineering, 2004. 86(2): p. 188-195.]. CFPS allows expression of the proteins in soluble form, and its accessible environment provides great flexibility in optimizing protein expression. Protein product concentrations may be measured in a 96-well plate format by incorporating a 14C-labeled mixture of fifteen amino acids during CFPS. The amino acid mixture minimizes bias in radioactive incorporation due to mutations. Samples from each CFPS reaction are then precipitated and collected in parallel using a cell harvester, and the protein concentrations determined by scintillation counting. The sequences of proteins in a library prepared by this high-throughput can be obtained after recovering their DNA from the corresponding wells in the SM-PCR plates. CFPS components exhibited no adverse effects or interference in three different cell assays tested (proliferation, directional migration, and chemotactic migration), providing the unexpected advantage of eliminating the need for protein purification or processing before screening.

In another aspect, the invention encompasses mutant EGF polypeptides identified by the screening method described above. In alternative exemplary embodiments, the mutant EGF polypeptide identified by the claimed method comprises SEQ ID NO:2 and SEQ ID NO:3. In another embodiment, the mutant EGF polypeptide identified by the claimed method comprises a polypeptide which exhibits statistically significant biological activity at a concentration at which the activity of wild-type EGF is equivalent to background. In another embodiment, the mutant EGF polypeptide identified by the claimed method comprises a polypeptide which exhibits biological activity greater than that exhibited by wild-type EGF at the same concentration.

Reagents, Devices and Kits

Also provided are reagents, devices and kits thereof for practicing one or more of the above-described methods. The subject reagents, devices and kits thereof may vary greatly. For examples, kits for use in screening methods to identify novel mutant EGF polypeptides comprising one or more of the characteristics described herein may include one or more mutant EGF polypeptides or a mutant EGF polypeptide library, control polypeptides, cells, buffers, etc. As another example, kits for use in therapeutic methods may comprise one or more mutant EGF polypeptides, such as a label or additional therapeutic agent.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

EXPERIMENTAL EXAMPLES

Example 1

Screening and Selection of Mutant EGF Polypeptides 1.10 ("T10", SEQ ID NO: 2) and 1.78 ("T78", SEQ ID NO: 3)

Directed evolution is a powerful strategy for protein engineering; however, evolution of pharmaceutical proteins has been limited by the reliance of current screens on binding interactions. Here, we present a method that identifies protein mutants with improved overall cellular efficacy, an objective not feasible with previous approaches. Mutated protein libraries were produced in soluble, active form by means of cell-free protein synthesis. The efficacy of each individual protein was determined at a uniform dosage with a high-throughput protein product assay followed by a cell-based functional assay without requiring protein purification. We validated our platform by first screening mock libraries of epidermal growth factor (EGF) for stimulation of cell proliferation. We then demonstrated its effectiveness by identifying EGF mutants with significantly enhanced mitogenic activity at low concentrations compared to that of wild-type EGF. This is the first report of EGF mutants with improved biological efficacy despite much previous effort. Our platform can be extended to engineer a broad range of proteins, offering a general method to evolve proteins for improved biological efficacy.

In the past few decades, directed evolution has emerged as a powerful strategy for understanding and engineering a protein's biological function (Arnold, F H et al. (2001) How enzymes adapt lessons from directed evolution. Trends Biochem, Sci., 26, pp. 100-106; Brannigan, J A et al. (2002) Protein engineering 20 years on. Nat. Rev. Mol. Cell Biol., 3, pp. 964-970; Vasserot A P et al. (2003) Optimization of protein therapeutics by directed evolution. Drug Discov. Today, 8, pp. 118-126; Yuen, C M et al. (2007) Dissecting protein structure and function using directed evolution, Nat. Methods, 4, pp. 995-997). Many directed evolution platforms, such as phage display (Sidhu, S S et al. (2007) Phage display for engineering and analyzing protein interaction interfaces. Curr. Opin. Struct. Biol., 17, pp. 481-487) and yeast surface display (YSD) (Pepper, L R et al. (2008) A decade of yeast surface display technology: where are we now?. Comb. Chem. High Throughput Screening, 11, pp. 127-134) have been developed. In general, the screening criteria used in these platforms are based on binding interactions, making them effective methods to evolve proteins with high binding affinity against a target of interest. However, this reliance on binding interactions limits the capacities of current platforms to engineer a protein's overall biological function, and this limitation has severely restricted the evolution of improved protein agonists (Ciardelli, T L (1996) Reengineering growth factors "through the looking glass". Nat. Biotechnol., 14 p. 1652, Jones, D S et al. (2008) Developing therapeutic proteins by engineering ligand-receptor interactions. Trends Biotechnol., 26, pp, 498-505). In many cases, a protein's binding affinity toward, for example, a receptor does not correlate with biological efficacy, and maximizing affinity can even be counterproductive (Chang, D Z et al. (1996) A point mutation in interleukin-2 that alters ligand internalization. J. Biol. Chem., 271, pp. 13349-13355; J. M. Haugh (2004) Mathematical model of human growth hormone (hGH)-stimulated cell proliferation explains the efficacy of hGH variants as receptor agonists or antagonists. Biotechnol. Prog., 20, pp. 1337-1344; Reddy, C C et al. (1996) Engineering epidermal growth factor for enhanced mitogenic potency. Nat. Biotechnol., 14, pp. 1696-1699). This is due to myriad additional factors that influence cell signaling, including binding kinetics, receptor internalization, and intracellular protein trafficking (Lazzara, M J (2009) Quantitative modeling perspectives on the ErbB system of cell regulatory processes, Exp. Cell Res., 315, pp. 717-725; Lemmon, M A et al. (2010) Cell signaling by receptor tyrosine kinases. Cell, 141, pp. 1117-1134).

Thus, there is a great need for an efficient, general method to screen libraries of mutant proteins for overall biological function. Such technology has not been introduced due to many challenging requirements. First, the screening platform must be able to express complex mammalian proteins, which often contain disulfide bonds, in soluble, active form. Ideally, the proteins would also be in their native state without extensions or attachments to avoid interfering with natural cell signaling and protein trafficking. Second, the expression system needs to be robust and capable of producing diverse protein mutants for full evaluation of randomized libraries. Third, each member of the protein library must be tested at a uniform dosage for accurate screening. This necessitates the measurement of each protein's concentration, since mutated proteins often express at highly variable yields. This is especially important when searching for minor improvements and using nonlinear biological assays. Fourth, the protein library should be assessable without time-consuming and expensive purification or processing. Finally, the platform must judge each protein on the basis of its overall effect on target cells and be compatible with a variety of cellular assays.

Current evolution platforms fail to provide several of these requirements. A few techniques that screen combinatorial libraries based on kinase activity or reporter gene expression have been reported, but they suffer from several drawbacks, including lack of general applicability, limited throughput, requirement for protein purification, and/or introduction of artifacts due to the use of multivalent phage display (Chang, D Z et al. (1996) A point mutation in interleukin-2 that alters ligand internalization. J. Biol. Chem., 271, pp. 13349-13355; Coco, W M et al. (2002) Growth factor engineering by degenerate homoduplex gene family recombination. Nat. Biotechnol., 20, pp, 1246-1250: Souriau, C et al. (1997) A simple luciferase assay for signal transduction activity detection of epidermal growth factor displayed on phage. Nucleic Acids Res., 25, pp. 1585-1590; Souriau, C et al. (1999) Direct selection of EGF mutants displayed on filamentous phage using cells overexpressing EGF receptor. Biol. Chem., 380, pp. 451-458). Furthermore, these techniques still can only evaluate a protein's biological activity based on intermediate metrics.

We report here a directed evolution platform that accomplishes all of the above requirements to enable protein engineering directly for improved biological efficacy (FIG. 1). This technology takes a radical new approach, incorporating single-molecule PCR (SM-PCR) (Rungpragayphan, S et al. (2004) Rapid screening for affinity-improved scFvs by means of single-molecule-PCR-linked in vitro expression. J. Mol, Catal. B: Enzym., 28, pp. 223-228) cell-free protein synthesis (CFPS) (Goerke, A R et al (2008) Development of cell-free protein synthesis platforms for disulfide bonded proteins. Biotechnol. Bioeng., 99, pp. 351-367; J. Swartz (2006)

Developing cell-free biology for industrial applications. J. Ind. Microbial. Biotechnol., 33, pp. 476-485), assessment of product concentration, and a cell-based assay, which are all performed in microtiter plates. Coupling these methods with multiple innovations, we can produce a library of protein mutants in soluble, active form and measure each individual protein's effect on mammalian cells in a high-throughput format.

To validate our platform, we chose epidermal growth factor (EGF) as a model protein and screened for enhanced stimulation of cell proliferation. EGF plays an important role in the healing process, and a more potent EGF agonist has potential applications in wound healing, tissue engineering, and regenerative medicine (Werner, S (2003) Regulation of wound healing by growth factors and cytokines. Physiol. Rev., 83, pp. 835-870; Hardwicke, J (2008) Epidermal growth factor therapy and wound healing—past, present and future perspectives. Surgeon, 6, pp. 172-177; Marcantonio, N A et al. (2009) The influence of tethered epidermal growth factor on connective tissue progenitor colony formation. Biomaterials, 30, pp. 4629-4638). EGF is also a difficult target because it undergoes a complex cell signaling and trafficking pathway after binding to its receptor (EGFR) (Hardwicke, J (2008) Epidermal growth factor therapy and wound healing—past, present and future perspectives. Surgeon, 6, pp. 172-177; Wiley, H S (2003) Trafficking of the ErbB receptors and its influence on signaling Exp. Cell Res., 284, pp. 78-88). Many previous studies attempted to discover an enhanced EGF agonist by screening for (1) EGFR kinase activity (Coco, W M et al. (2002) Growth factor engineering by degenerate homoduplex gene family recombination. Nat. Biotechnol., 20, pp. 1246-1250), (2) reporter gene expression (Souriau, C et al. (1997) A simple luciferase assay for signal transduction activity detection of epidermal growth factor displayed on phage. Nucleic Acids Res., 25, pp. 1585-1590; Souriau, C et al. (1999) Direct selection of EGF mutants displayed on filamentous phage using cells overexpressing EGF receptor. Biol. Chem., 380, pp. 451-45), or (3) increased binding affinity to EGFR (Cochran, J R et al. (2006) Improved mutants from directed evolution are biased to orthologous substitutions. Protein Eng. Des. Sel., 19, pp. 245-253). But none of the identified EGF mutants in the first two studies stimulated cell proliferation at lower concentrations than wild-type (WT) EGF. In addition, we tested two high-affinity EGF mutants from the third study and found no improvement in mitogenic activity.

We first assessed the sensitivity of our platform by screening mock libraries composed of known ratios of WT and mutated EGF proteins, showing that we could identify proteins with differing activities when they represented only a hundredth of the library population and that we could differentiate between proteins with high, intermediate, and low biological activity levels. We then screened a true library of EGF mutants and isolated two enhanced EGF agonists, 1.10 (SEQ ID NO:2) and 1.78 (SEQ. ID NO:3) that stimulate cell proliferation at significantly lower concentrations than WT EGF, the first time such an improvement in activity has been reported. The successful screening of mock and true libraries establishes our platform's ability to screen protein libraries directly for improved biological activity. Moreover, this platform can be extended to engineer a range of proteins and can be adapted to screen for different effects using any plate-based functional assay.

Materials and Methods

Mock Library Preparation.

Wild type human EGF was cloned into the pK7 plasmid (Goerke, A R et al. (2008) Development of cell-free protein synthesis platforms for disulfide bonded proteins. Biotechnol. Bioeng., 99, pp. 351-367) and point mutants were constructed using the QuikChange method (Stratagene). Linear templates were generated by two-step PCR Woodrow, K A at al. (2006) Rapid expression of functional genomic libraries, J. Proteome Res., 5, pp. 3288-3300). In the first PCR, the EGF gene and T7 expression elements were amplified with the following primers: 5'-ACACGACGTGAACGATAGGAAT-TGAAACGAGTTCGCGGCCGCTTAGGCAC-CCCAGGCTTTAC-3' (SEQ ID NO:18) and 5'-ACAC-GACGTGAACGATAGGAATTGAAACGAGTTCGACG-AGCGTCAGCTTGCATGCCCTGCAGCT-3' (SEQ ID NO:19). This PCR product was then amplified in a second PCR to produce the final template with the sca2 homoprimer (5'-ACACGACGTGAACGATAGGAATTGA-3' (SEQ ID NO:8)) (Rungpragayphan, S et al. (2004) Rapid screening for affinity-improved scFvs by means of single-molecule-PCR-linked in vitro expression. J. Mol. Catal. B: Enzym., 28, pp. 223-228). DNA concentrations were measured with the Qubit Quantitation Platform (Invitrogen); and mock libraries were created by mixing DNA templates in the desired ratios by mass.

True Library Preparation.

The true DNA library was obtained from an intermediate sort of a previous EGF engineering project using YSD (Cochran, J R et al. (2006) Improved mutants from directed evolution are biased to orthologous substitutions. Protein Eng. Des. Sel., 19, pp. 245-253).

The library was amplified by PCR from the YSD construct (pCT vector) using generic vector primers (forward: 5'-GTG-GTGGTGG TTCTGGTGGT GGTGGTTCTG GTGGTG-GTG GTTCT GCTAGC-3' (SEQ ID NO:6); reverse: 5'-ATCTCGAGCT ATTACAAGTC CTCTTCAGAA ATAAGCTTT TGTTC GGATCC-3' (SEQ ID NO:7). The correct length product was purified through gel electrophoresis and gel extraction (Qiagen).

The library was then digested with NheI and BamHI and ligated into the pBL1 plasmid, a T7-based expression vector. pBL1 was constructed by inserting NheI and BamHI restriction enzyme sites inside the coding region of the pK7 plasmid (Goerke, A R et al. (2008) Development of cell-free protein synthesis platforms for disulfide bonded proteins. Biotechnol. Bioeng., 99, pp. 351-367). Linear template including the T7 expression elements was amplified with primers that contained the sca2 homoprimer, as described above.

Single-Molecule PCR.

Mock libraries were diluted to ~10-100 templates per microliter in TE buffer [20 mM Tris-HCl, 0.5 mM EDTA (ethylenediaminetetraacetic acid), pH 7.5] with 0.1% blue dextran to prevent nonspecific absorption. DNA was the added to SM-PCR reactions for a final template concentration of ~0.22 templates per reaction.

SM-PCR reactions (7.5 µl) were performed in 96-well or 384-well PCR plates (VWR) with the following final concentrations: 0.2 mM deoxynucleotide triphosphates, 0.25 µM sca2 homoprimer (Rungpragayphan, S et al. (2004) Rapid screening for affinity-improved scFvs by means of single-molecule-PCR-linked in vitro expression, J. Mol. Catal. B: Enzym., 28, pp. 223-228), and PfuTurbo Polymerase (0.03 U/µl) with 1×Pfu buffer (Stratagene). The reactions were cycled 80 times with the following protocol: 94° C. for 10 s, 65° C. for 10 s, and 72° C. for 10 s. To minimize contamination, reactions were mixed with a dedicated pipetman in a laminar flow hood. Before every use, the flow hood was cleaned with DNA-OFF DNA removal solution (Takara).

Product was detected with the Quant-iT PicoGreen dsDNA Reagent (Invitrogen). One microliter of the SM-PCR reaction was added to 100 µl of PicoGreen Reagent diluted 2000-fold.

Fluorescence was detected at 485-nm excitation and 535-nm emission wavelengths with a Mithras LB 940 (Berthold Technologies). Control samples were periodically measured to determine the fluorescence cutoff value for DNA product.

Cell-Free Protein Synthesis (CFPS).

The PANOx-SP cell-free system as used for protein expression. CFPS reaction mixtures were composed of the following: 20 mM magnesium glutamate, 10 mM ammonium glutamate, 175 mM potassium glutamate, 1.2 mM ATP, 0.86 mM each CTP, GTP, and UTP, 10 mM potassium phosphate, folinic acid (34 μg/mL), E. coli tRNAs (170 μg/mL), 33 mM phosphoenol pyruvate, 1.5 mM spermidine, 1 mM putrescine, 0.33 mM nicotinamide adenine dinucleotide (oxidized form), 0.27 mM coenzyme A, 2.7 mM sodium oxalate, 2 mM each of the 20 unlabeled amino acids, T7 RNA polymerase (100 μg/mL), 4 mM oxidized glutathione, 1 mM reduced glutathione, DsbC (100 μg/mL), Gam (100 μg/mL), and 0.24 (v/v) of E. coli KGK10 S30 extract, (Knapp, K G et al. (2007) Cell-free synthesis of proteins that require disulfide bonds using glucose as an energy source. Biotechnol. Bioeng., 97, pp. 901-908).

Protein was radiolabeled by adding 1.6 μCi of I-[U-14C] leucine or I-[U-14C]amino acid mixture (Perkin Elmer). To encourage formation of disulfide bonds, the S30 extract was pretreated with 50 μM iodoacetamide for 1 h at room temperature. When stated, IFs were supplemented to a final concentration of 4 μM. After preparation, all CFPS reaction mixtures were incubated at 37° C. for 3 h.

Standard reactions from a plasmid template were performed in 30 μl volume and contained 53.3 μg/ml DNA. For library screening, reactions were performed in 10 μl volume in 96-well plates and 1 μl of unpurified SM-PCR product was used as template. Standard protein concentrations were measured by spotting 4 μl of the CFPS reactions on individual filter papers, washing the papers in ice-cold 5% TCA, and performing scintillation counting.

To measure protein concentration in 96-well plates, 4 μl of each CFPS reaction was precipitated in phosphate-buffered saline buffer with 10% TCA and bovine serum albumin (1 mg/ml) for 30 min at 4° C. Precipitated protein was then captured on glass fiber filter mats (Perkin Elmer) with a Mach IIIM Harvester (Tomtec). Scintillation counting was performed with a Wallac MicroBeta Counter (Perkin Elmer).

Cell Proliferation Assays.

BJ-5ta cells, human immortalized foreskin fibroblast cells that express human EGFR (American Type Culture Collection), were plated in 96-well plates at a density of 2500 cells per well in 100 μl of full medium [Dulbecco's modified Eagle's medium (DMEM)] supplemented with 1% penicillin/streptomycin (Pen/Strep), 1% I-glutamine, 1% sodium pyruvate, 20% M199, and 10% fetal bovine serum. All cell culture reagents were from invitrogen. After 24 h, cells were serum-starved for 48 h in serum-free medium (DMEM supplemented with 1% Pen/Strep, 1% I-glutamine, 1% sodium pyruvate, and 20% M199). The medium was then replaced with 100 μl of serum-free medium containing the indicated concentrations of treatment protein.

When indicated, the standard serum-free medium used during protein treatment was replaced with advanced media (Advanced DMEM supplemented with 1% Pen/Strep, 1% I-glutamine, 1% sodium pyruvate, and 20% M199) or supplemented with human recombinant insulin. After an additional 48 h, 1 μCi of [3H]TdR (GE Healthcare) was added to each well in 50 μl of serum-free medium.

[3H]TdR incorporation was measured 24 h later by freezing the plates at −80° C. overnight, thawing the plates at room temperature, harvesting the cells onto glass fiber filter mats (Perkin Elmer) with a Mach IIIM Harvester (Tomtec), and performing scintillation counting with a Wallac MicroBeta Counter (Perkin Elmer).

Directional Cell Migration Assay.

Approximately 4 cm by 1 cm wide silicon strips were placed in the center of 6-well tissue culture treated plates. BJ-5ta cells were then plated at a density of $3 \times 10^5$ cells/well in full medium. After 24 hr, cells were serum-starved for 48 hr in serum-free medium. The silicon strip was then gently removed with tweezers to create an artificial wound in the cell monolayer. The cells were incubated for 10 min at 37° C. to allow for recovery. The medium was then removed and replaced with serum-free medium containing 25 nM of the indicated EGF protein. Pictures of the wound gap were taken with an inverted phase contrast microscope using a 4× objective every 12 hours for 3 days. Wound width was measured at 3 locations in each well, and percent closure was calculated relative to the width at 0 hr.

Chemotactic Cell Migration Assay.

Costar transwells (8.0 μm pores, 6.5 mm diameter) were coated on both sides with bovine fibronectin (10 μg/ml) overnight at 4° C., washed 3 times with PBS, and then blocked with 1% bovine serum albumin (BSA) in PBS at 37° C. for 1 h prior to usage, $2.5 \times 10^5$ cells in 200 μl of serum-free medium with 1% BSA were placed into the upper chamber of the coated transwells and allowed to migrate toward media containing 0.3 nM of the indicated protein in the lower chamber for 3 hr under tissue culture conditions. Non-migrated cells were removed by wiping the upper side of the membrane with a cotton swab. The transwells were washed three times with PBS, fixed with methanol, and stained with modified Giemsa. Pictures were taken of the migrated stained cells in nine random high-powered fields (20×) using light microscopy, and the number of migrated cells was counted.

Statistical Analysis.

Statistical analysis comparing the [3H]TdR incorporation of WT and mutants 1.10 and 1.78 was performed with a one-tailed independent Student's t test. P values are from comparison between the indicated mutant and WT EGF at the stated treatment concentration with n=6, using four batches of protein on four different days.

Results

Platform Methodology and Development.

Figure 2:
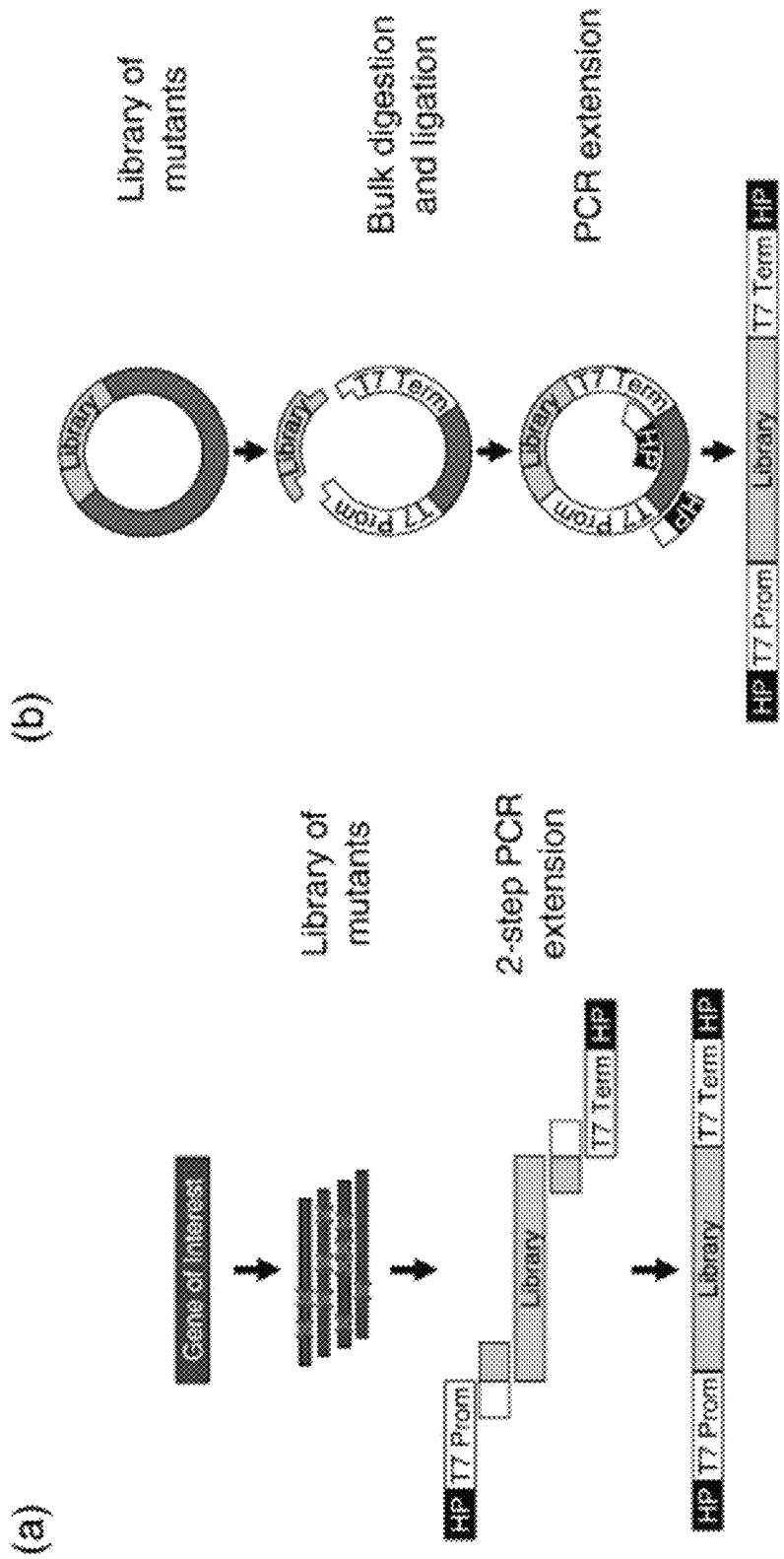
FIG. 2. Library preparation. DNA libraries can be prepared by PCR assembly or bulk cloning. (a) In the first approach, mutations are introduced into a gene of interest and the library is extended with homoprimer sites (HP) and T7 promoter and terminator elements (T7 Prom and T7 Term, respectively) for SM-PCR and CFPS. (b) In the second, an existing library is bulk cloned from its original vector into a T7 expression vector. Linear template is amplified by PCR with primers that contain the HP site and anneal outside of the T7 expression elements.

The first step is the preparation of a DNA library (FIG. 2). Any mutagenesis technique can be used to introduce diversity into a gene of interest, and the cell-free platform offers the convenience of using linear DNA templates, thereby avoiding the need for cloning into plasmids. The only requirement is the addition of T7 RNA polymerase promoter and terminator elements, which can be easily appended onto mutated genes by PCR assembly (Woodrow, K A et al. (2006) Rapid expression of functional genomic libraries J. Proteome Res., 5, pp. 3288-3300).

Figure 6:
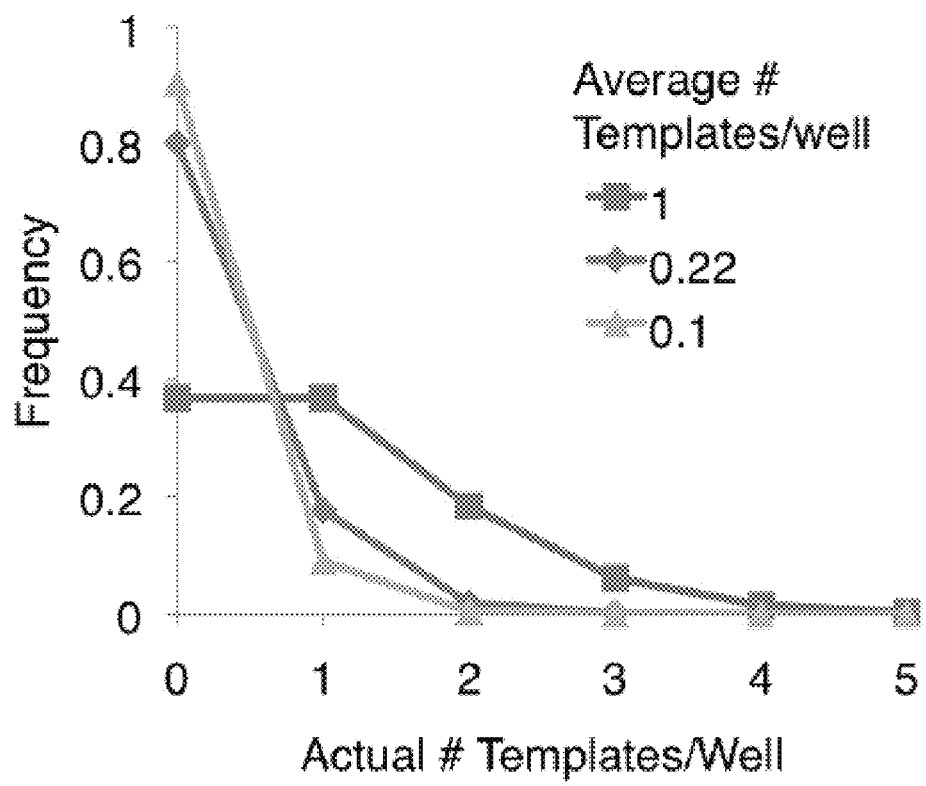
FIG. 6. Template distribution with SM-PCR is governed by the Poisson distribution. An average concentration of ~0.22 molecules/well was chosen to maximize the number of wells with a single template and minimize the number of wells with two or more templates.
Figure 7:
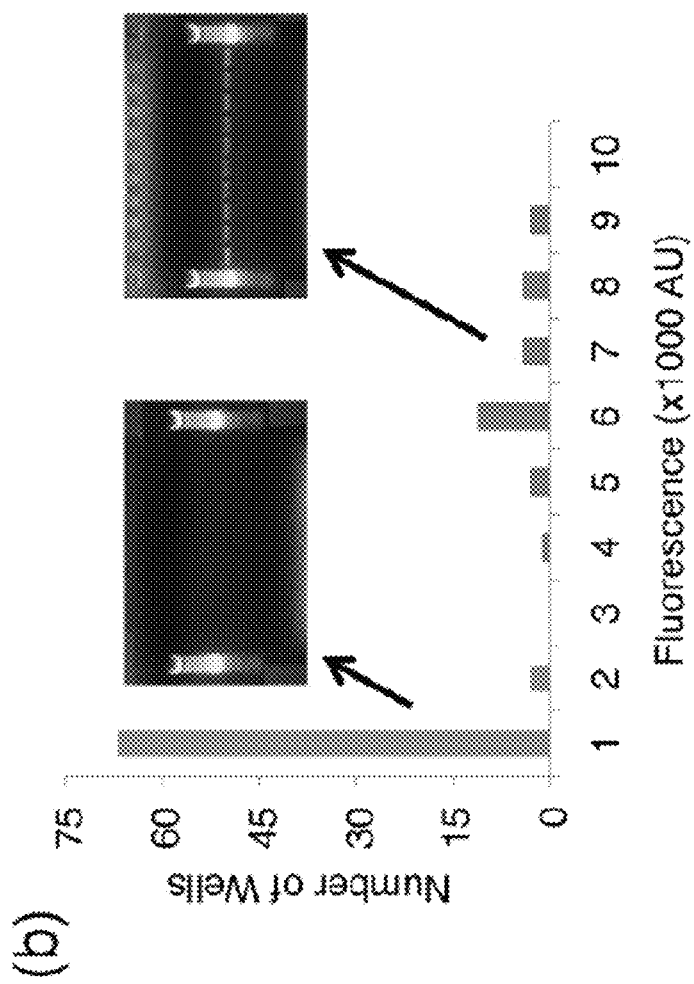
FIG. 7. Verification of SM-PCR with a fluorescent dye. An example reading from a 96-well plate after SM-PCR to check for the presence of DNA product, presented in plate (a) and histogram (b) formats. Fluorescence is presented in arbitrary units (AU). Wells with DNA are green. Accuracy of the dye assay can be confirmed by running samples on agarose gels. A band at the expected molecular weight of ~600 base pairs is only seen in positive wells.

Next, the DNA library is diluted to ~0.22 molecules per well into microtiter plate wells to separate the templates. This low average concentration minimizes the probability of wells containing two or more templates (FIG. 6). SM-PCR is then used to amplify the single DNA molecules to provide sufficient template for protein expression. To prevent aberrant products often seen in SM-PCR reactions, the templates are amplified using a single homoprimer, which is complementary to both the 5' and the 3' ends of the templates Rungpragayphan, S et al. (2004) Rapid screening for affinity-improved scFvs by means of single-molecule-PCR-linked in vitro expression. J. Mol. Catal. B: Enzym., 28, pp, 223-22, Rungpragayphan, S et al. (2007) SIMPLEX: single-molecule PCR-linked in vitro expression: a novel method for high-throughput construction and screening of protein libraries. Methods Mol. Biol. 375, pp, 79-94) (FIG. 2). We optimized the homoprimer and polymerase concentrations to consistently produce only the desired product and used the Pfu. DNA polymerase to minimize the risk that PCR errors would result in multiple PCR products in that well. After SM-PCR, a fluorescent dye is used to detect the presence of amplified DNA template in the 96-well plates (FIG. 7). This allows us to judge the quality of SM-PCR reactions and to move forward only with wells that contain template, eliminating wasted reagents in subsequent steps (due to the extensive dilution, ~75% of the wells are empty).

Figure 8:
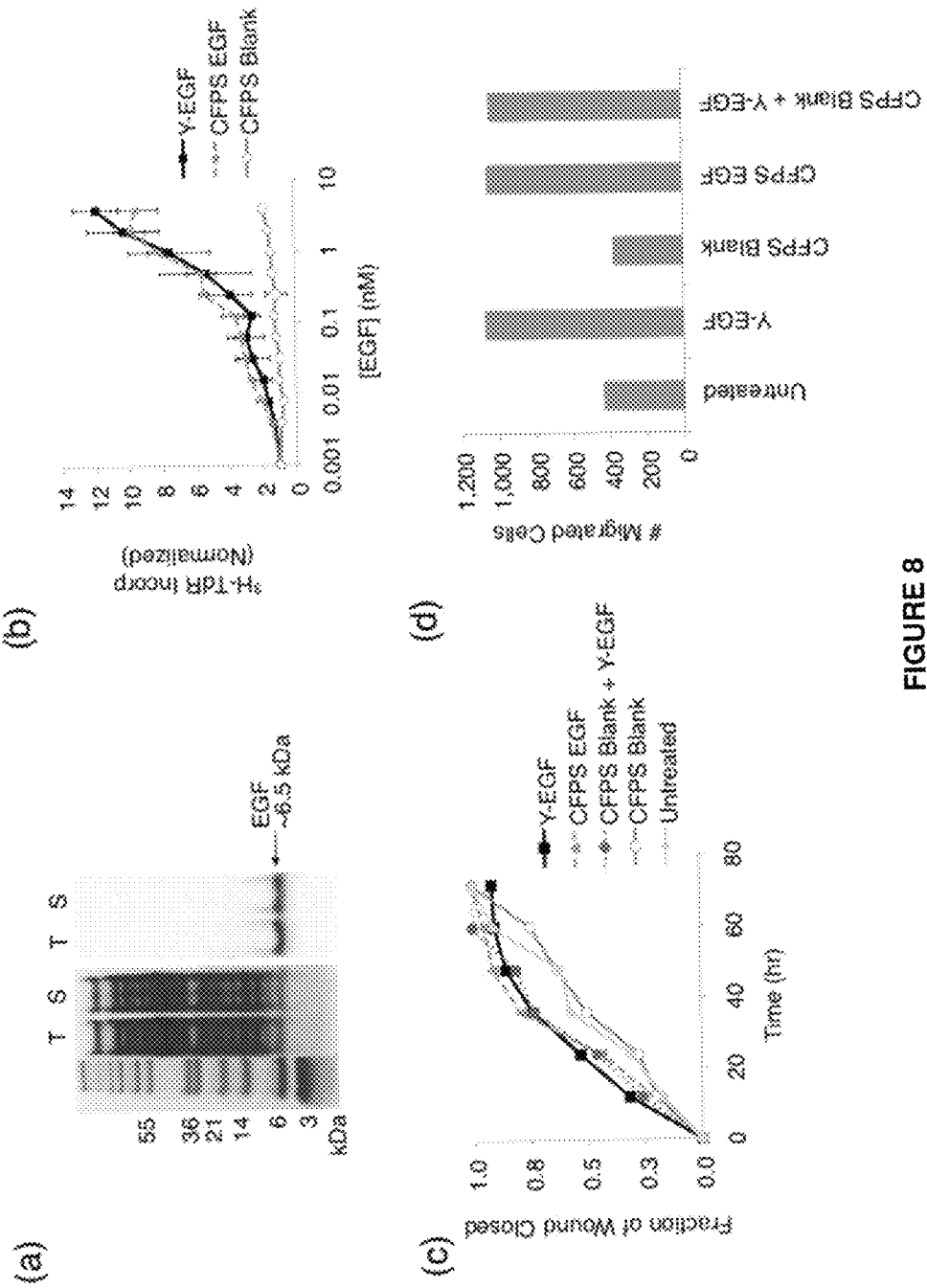
FIG. 8. Expression of active, soluble wild-type EGF by CFPS. (a) Autoradiogram showing total (T) and soluble (S) fractions of 14C-labeled wild-type EGF expressed by CFPS (CFPS EGF), Activity of CFPS-produced EGF was confirmed by comparison with blank CFPS reactions (CFPS Blank) and purified EGF expressed in *S. cerevisiae* (Yeast EGF) using three cell-based assays: cell proliferation (b), directional migration (c), and chemotactic migration (d). Treatments with serum-free media (SFM) or CFPS Blank+ Yeast EGF were occasionally used as additional negative controls, Error bars, s.d. (n=3).

The DNA template in each well of the microliter plates is then translated into protein by oxidizing CFPS (Goerke, A. R. & Swartz, J. R. (2008). Development of cell-free protein synthesis platforms for disulfide bonded proteins. Biotechnol Bioeng. 99, 351-367). CFPS allows us to express the proteins in soluble form, and its accessible environment provides us with great flexibility in optimizing protein expression. For example, to prevent degradation of the linear DNA templates and increase protein yields, we supplemented the standard CFPS reaction with the Gam protein from bacteriophage λ, which inhibits DNA nuclease activity (Sitaraman, K. (2004) A novel cell-free protein synthesis system. J. Biotechnol., 110, pp. 257-263). Because EGF contains three disulfide bonds, we also altered the reaction to create an oxidizing environment and added a disulfide bond isomerase (DsbC) for proper folding (Goerke, A R et al. (2008) Development of cell-free protein synthesis platforms for disulfide bonded proteins. Biotechnol. Bioeng., 99, pp. 351-367). With these modifications, we showed that soluble and active WT EGF was consistently produced, as verified by three cell-based assays (FIG. 8).

Figure 3:
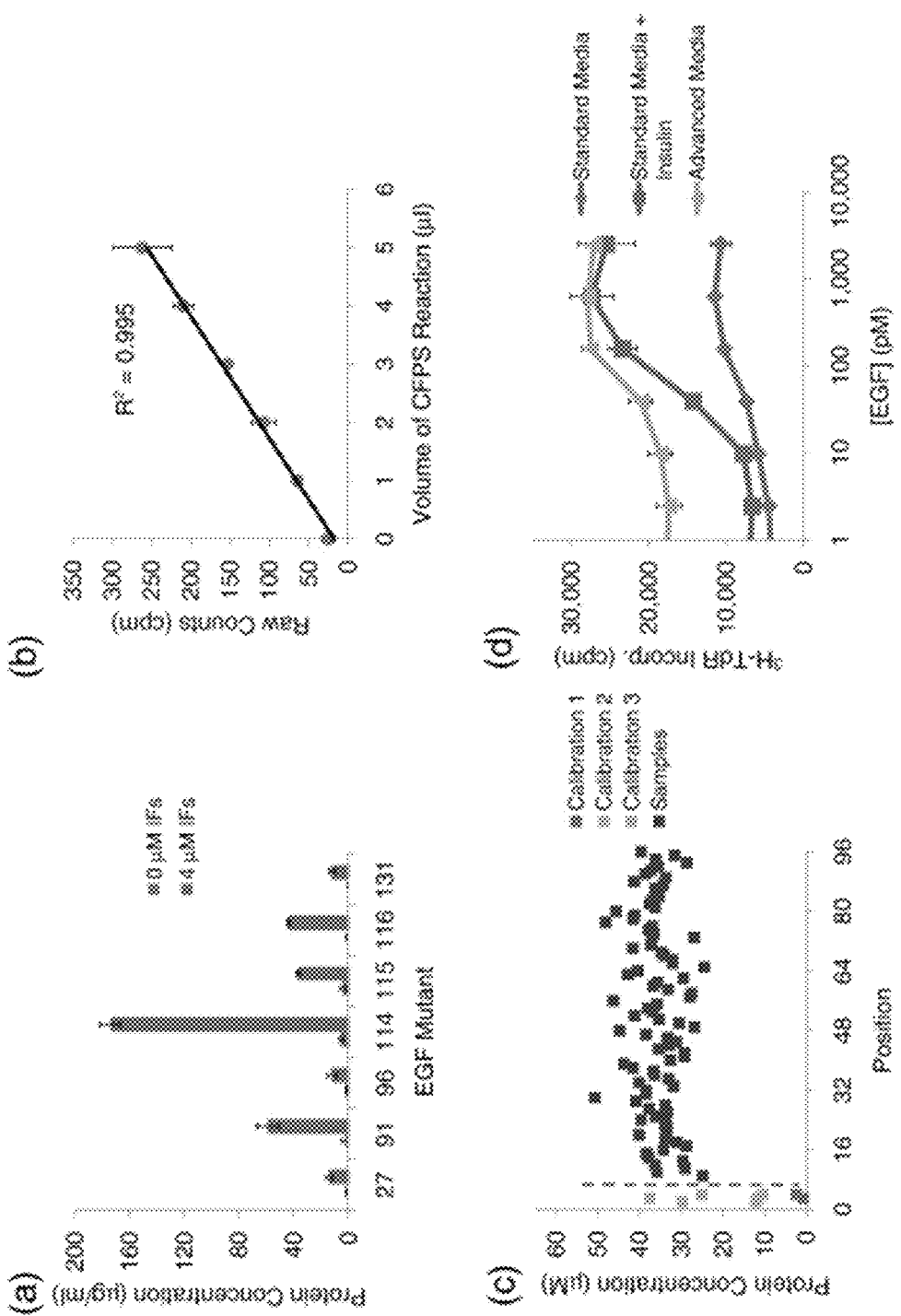
FIG. 3. Platform development. (a) CFPS expression levels of seven poorly expressing EGF mutants with and without the addition of 4 μM IFs. Error bars, SD. (n=3). (b) Linear correlation between the amount of CFPS-produced EGF and the counts detected using the 96-well product assay. Error bars, SD. (n=3), (c) Protein concentration measurements of 88 identical CFPS reactions, conducted in a 96-well plate format. The first column of every plate (left of the dotted line) is used for calibration standards to account for plate-to-plate variation. (d) Cell proliferation assayed by [3H]TdR incorporation after treatment with WT EGF in different serum-free medium formulations. Error bars, SD. (n=3).
Figure 9:
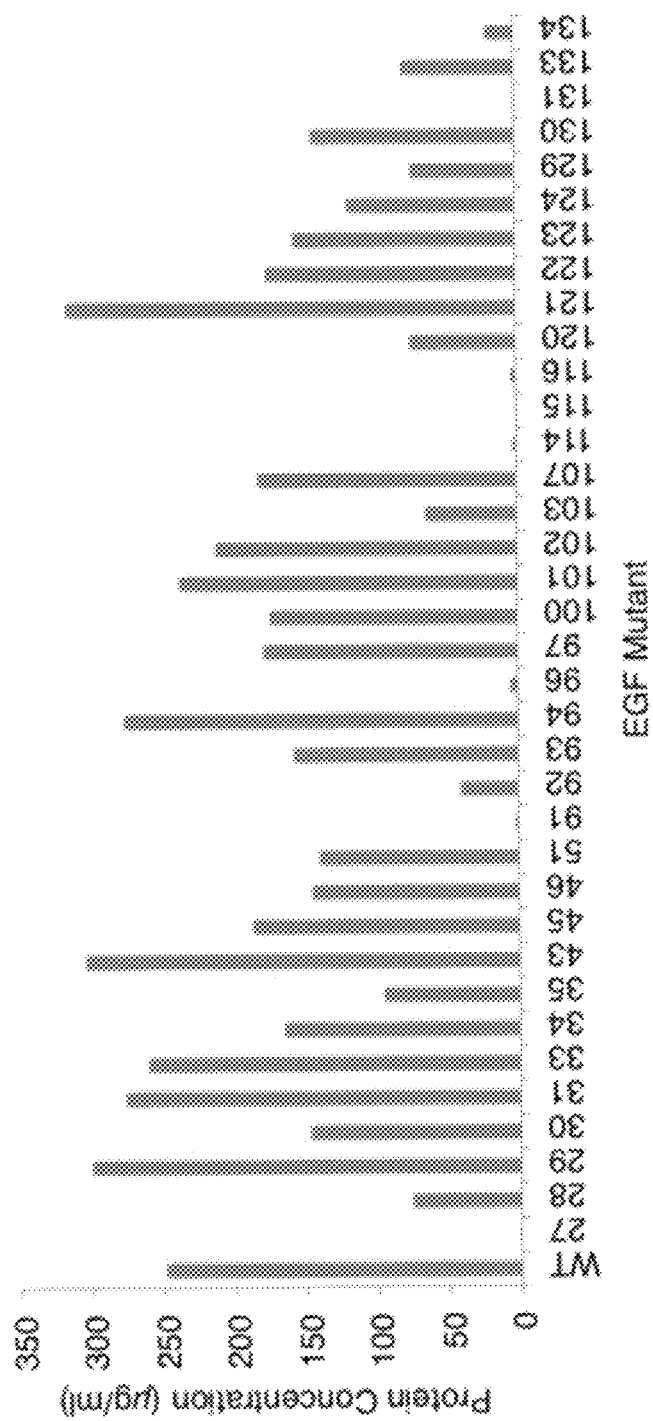
FIG. 9. CFPS expression levels of EGF wild-type (WT) and 36 EGF mutants previously identified from yeast surface display libraries 15. Seven EGF mutants (27, 91, 114, 115, 116, and 131) were not able to be expressed using CFPS.

To assess the ability to express a library of EGF mutants by CFPS, we tested a variety of previously isolated EGF mutants24 and found that neatly 0 were not produced (FIG. 9). The poorly produced mutants contained mutations in the first six codons, and these occurred frequently, since the previous screen favored isolates with N-terminal changes. We hypothesized that these mutations caused secondary structure in the mRNA and slowed translation initiation. To overcome this limitation, we increased the concentrations of the three *Escherichia coli* initiation factors ("Ifs", (IF-1, IF-2, and IF-3). This resulted in expression of all the candidates and provided confidence that our platform could fully evaluate a diverse protein library (FIG. 3a). Despite the addition of IFs, expression levels still varied significantly among the pool (relative SD of 78%). Therefore, in order to screen the library at a uniform dosage, we developed a method to efficiently measure product concentrations in a 96-well plate format by incorporating a 14C-labeled mixture of 15 amino acids during CFPS. The amino acid mixture minimizes bias in radioactive incorporation due to mutations. Taking advantage of the fact that only the product is produced in cell-free reactions, we then precipitated samples from each CFPS reaction with cold trichloroacetic acid (TCA) and collected them in parallel using a cell harvester. The product concentrations were then determined by scintillation counting. This method provides an accurate measurement of protein concentration, as illustrated by a linear calibration plot (FIG. 3b; typical assay SD≈10%), and calibration standards were included on every plate to account for variability (FIG. 3c). The assay is readily automatable, and the results enable approximately the same concentration of each mutant EGF to be used in the cell proliferation assays.

The next stage of the screen is to test the protein library for biological activity using a cell-based assay. Our platform's microliter plate format makes it compatible with a range of biological assays. Because of the >$10^6$ dilution of the CFPS reaction product solutions, the unpurified CFPS-produced EGF exhibited identical potency relative to that of purified EGF in three different cell assays (proliferation, directional migration, and chemotactic migration; FIG. 8), eliminating the need for any protein purification or processing before screening. For further platform validation, we chose to use cell proliferation, measured by [3]thymidine ([3H]TdR) incorporation, as our screen for biological activity. Proliferation is a widely applicable cellular readout and, in the case of EGF, could be applied to identify an enhanced variant for wound healing applications. Since cellular processing plays a major role in the biological response, we used BJ-5ta human foreskin fibroblast cells for library screening, a cell type relevant for wound healing. We optimized a variety of parameters including initial cell number, treatment times, and medium composition to maximize the dynamic range of the assay for high-throughput screening. For example, we found that medium supplemented with insulin resulted in a more sensitive assay for screening (FIG. 3d).

The final step is to obtain the sequences of proteins identified in the screen by recovering their DNA from the corresponding wells in the SM-PCR plates. Further rounds of screening can be performed to confirm and/or enhance biological activity.

Validation with EGF Mock Libraries.

Figure 4:
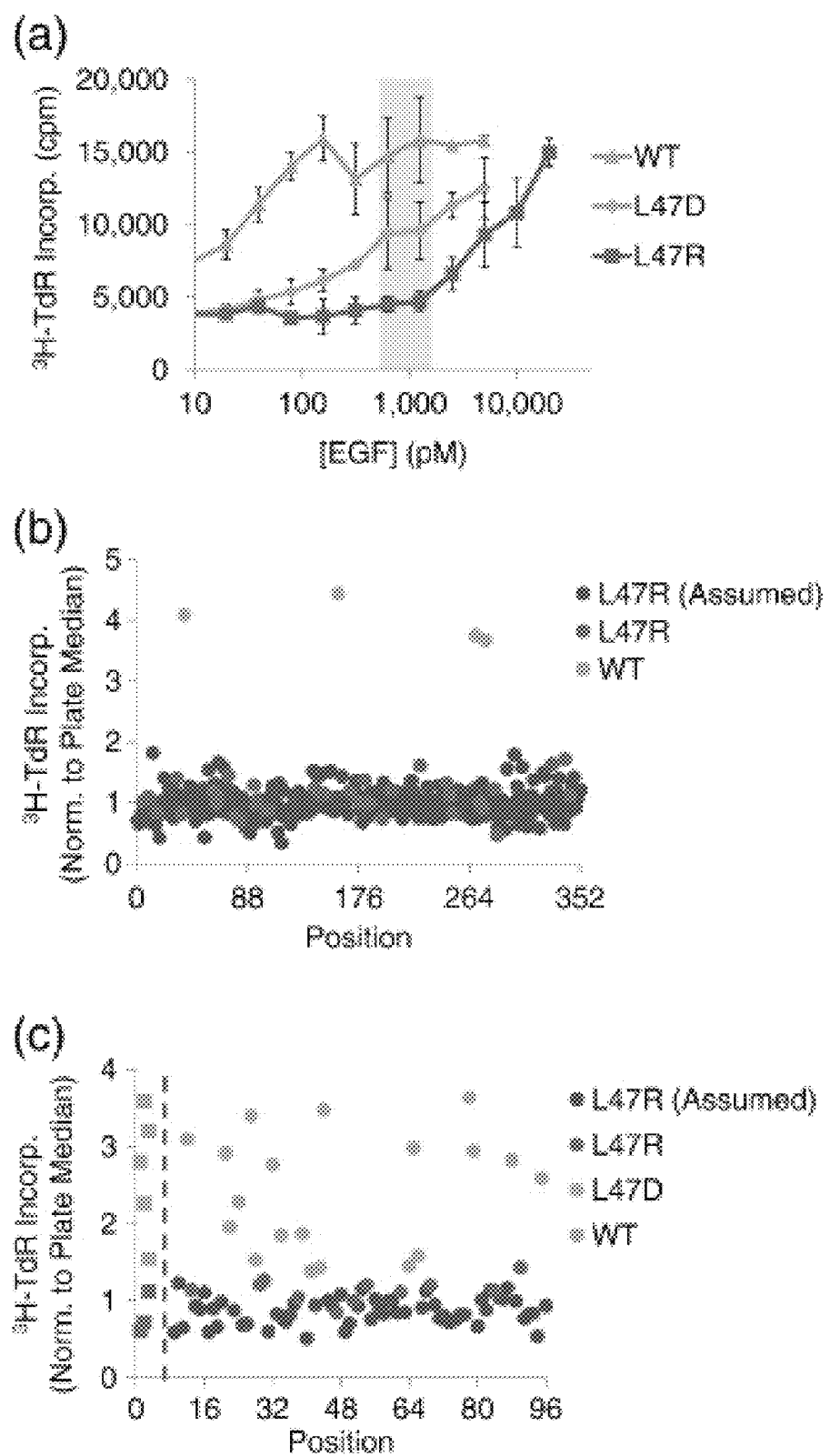
FIG. 4. Platform validation with EGF mock libraries. (a) WT EGF and two point mutants (L47D and L47R) were produced by CFPS and quantified by [14C]leucine incorporation and scintillation counting. They stimulated high, intermediate, and low levels of cell proliferation at 1 nM, as measured by a [3H]TdR incorporation assay. Error bars, SD. (n=3). DNA templates for WT, L47D, and L47R were combined in different ratios to create mock libraries. Results of screening a mock library composed of WT-L47R templates at a ratio of 1:100 (b) and WT-L47D-L47R templates at a ratio of 1:1:8 (c). [3H]TdR incorporated counts were normalized to each plate's median. Controls were included on every plate and are shown as squares left of the dotted line [not shown in (b) for clarity]. Library members are shown as circles. Clones of interest and a random selection of background wells were sequenced and are colored accordingly. Unsequenced background wells (blue) are assumed to be L47R. All product concentrations were measured and doses were normalized to approximately 1 nM.

To test the capabilities of our platform, we screened two mock libraries composed of WT and mutated EGF proteins, Two EGF mutants were created by substituting leucine 47 with arginine (L47R) or aspartic acid (L47D). The L47R mutation abolishes and the L47D mutation weakens EGF's biological activity (FIG. 4a). At 1 nM doses, WT EGF and the two variants stimulate high, intermediate, and low levels of cell proliferation. Mock libraries could not be constructed with EGF mutants that are more potent than WT, because such mutants had not yet been discovered. Therefore, we mixed DNA templates encoding WT and the less active EGF mutants in different ratios and screened these mock libraries on the basis of the stimulation of cell proliferation with 1 nM doses.

Figure 10:
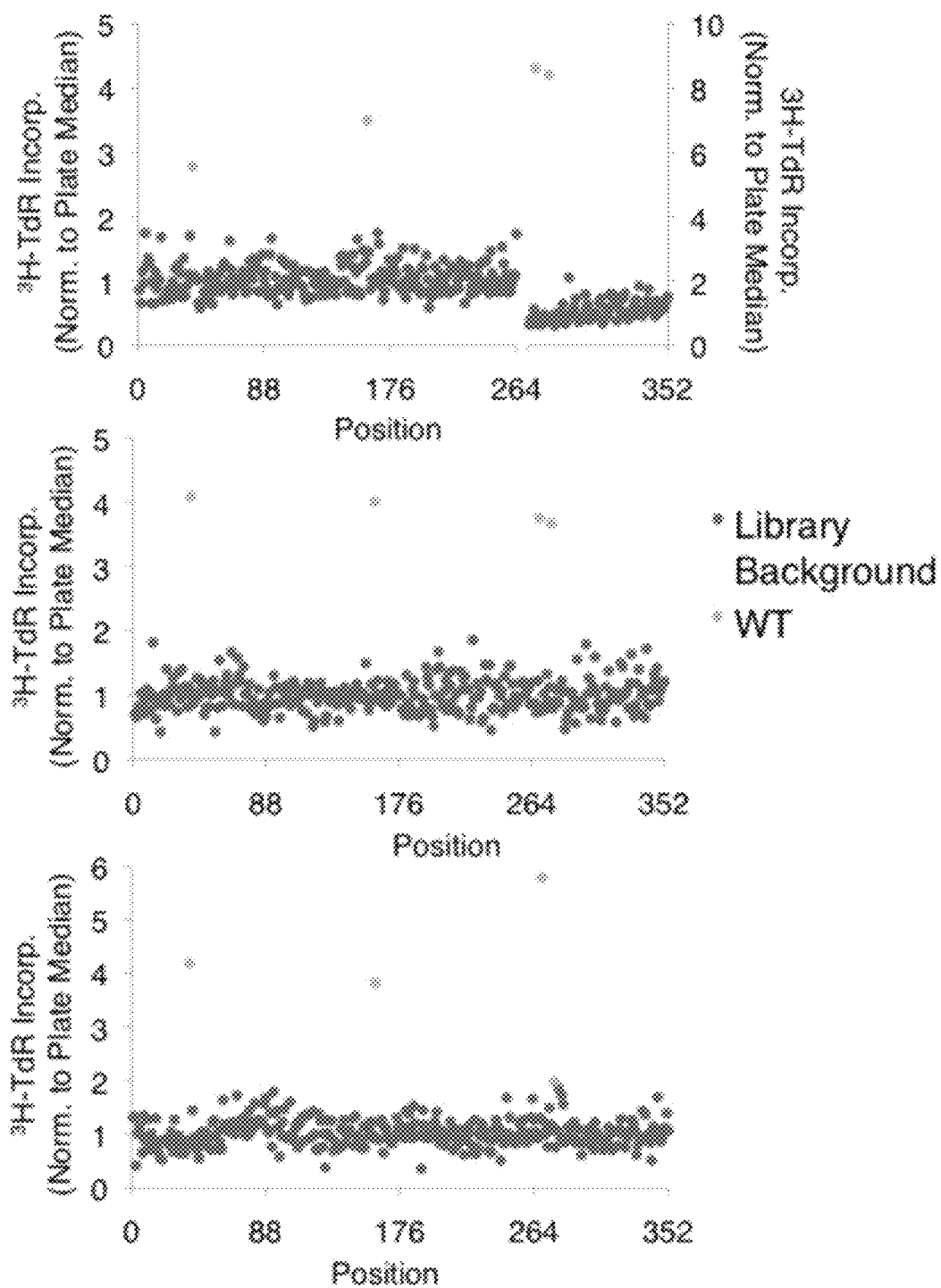
FIG. 10. Results of screening the WT:L47R::1:100 mock library. Four DNA plates (52 members) of the WT:L47R::1: 100 mock library were screened three times. The four WT wells (green) were identified every time except once. The fourth plate in the first screen produced abnormally high proliferation responses as indicated by the break in the x-axis and the use of a new y-axis to the right.

We first created a mock library composed of DNA templates for WT EGF and L47R in a ratio of 1 to 100. We screened 352 members (four plates) of this library and identified four "hits," which were confirmed to be WT EGF by DNA sequencing (FIG. 4b). The four plates were screened three times to assess the reproducibility of our screen, resulting in a single false negative and no false positives (FIG. 10). Thus, we demonstrated that our platform can identify mutants that exist at a 1% frequency with a single-pass probability of approximately $11/12=92\%$.

To further challenge our platform, we tested its ability to resolve intermediate differences in activity with a second mock library composed of WT EGF, L47D, and L47R at a ratio of 1:1:8. We screened 88 members of this library and identified 9 WT and 10 L47D clones (FIG. 4c). The WT EGF and L47D wells produced a consistent level of proliferation (relative SD of 10% and 20%, respectively) and also matched on-plate controls; the average [3H]TdR incorporation of the WT and L47D wells differed from that of controls by 3% and 5%, respectively. In the context of screening, a cutoff of 30% improvement over the plate median captures all of the WT and L47D clones and only one L47R sequence. Since protein evolution typically requires several rounds of screening, such false positives would be eliminated in the subsequent round.

Identification of Enhanced EGF Agonists.

After successful validation with mock libraries, we then applied our platform to identify EGF mutants with enhanced biological potency compared to WT EGF. Realizing that the plate-based format imposes a limitation on the library size, we screened a focused library that was biased to contain folded, functional EGF mutants. YSD had previously been used to screen an EGF library with randomized and recombined mutations to identify mutants with increased affinity for EGFR.24 We chose to begin with an intermediate sort from that study, with the goal of obtaining a pool of EGF mutants with at least a moderate level of binding affinity to EGFR (Kds less than 1 µM) but without significant enrichment. This library was converted from the YSD construct to a format for CFPS and SM-PCR using a bulk cloning procedure that appends two amino acids at the N- and C-termini but is able to preserve all mutations in the target protein (FIG. 2b). We confirmed that diversity was retained by sequencing 17 clones. We found no redundant gene sequences, and the number of mutations ranged from 2 to 11 amino acids.

Figure 5:
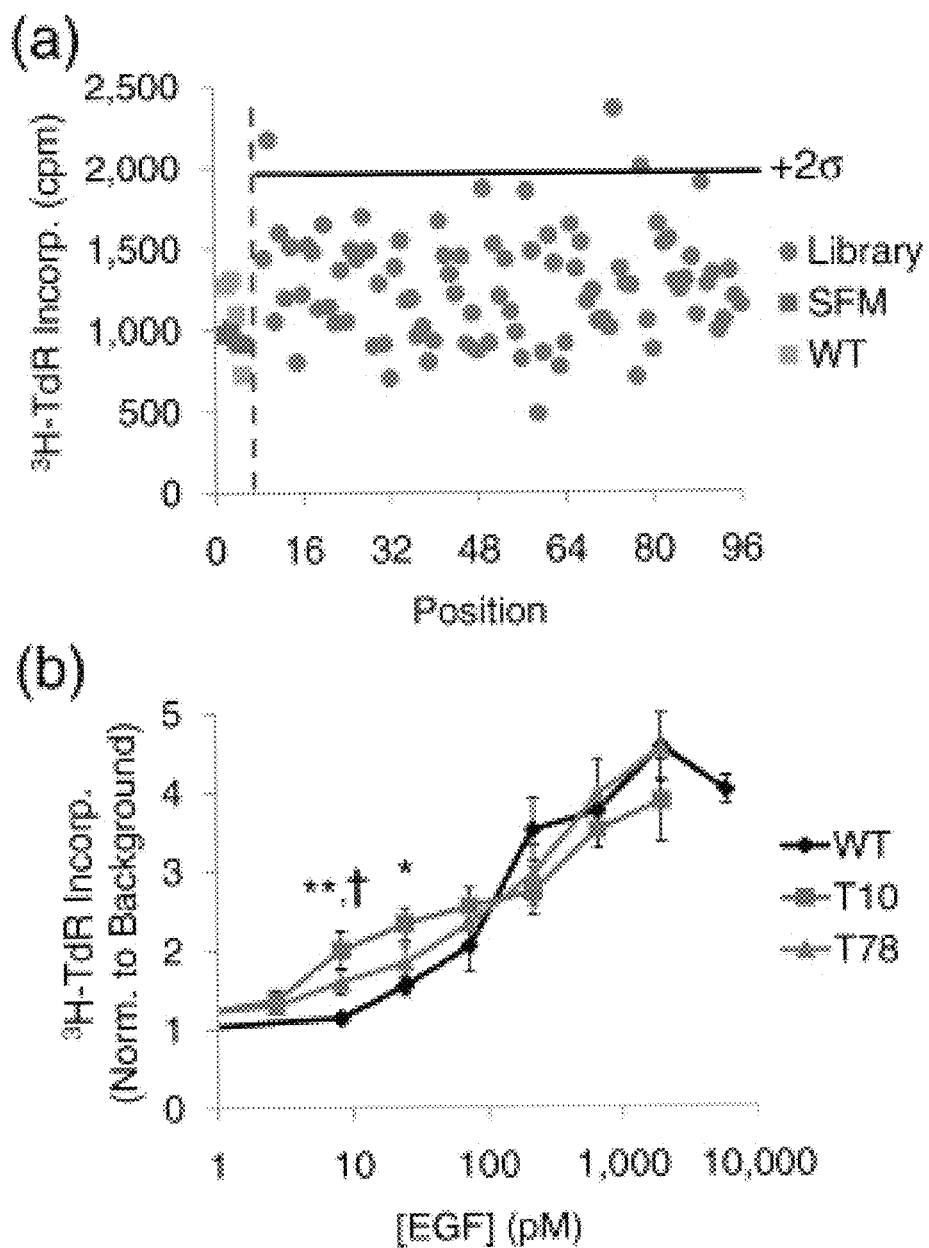
FIG. 5. Identification of enhanced EGF agonists. (a) An example plate from screening a true EGF library. On-plate controls are shown as squares left of the dotted line. Serum-free medium (SFM) was used as a negative control, and WT EGF at ~20 pM was included for comparison. Three clones at positions 10, 73, and 78 (named 1.10, 1.73 ("T73"), and 1.78) stimulated cell proliferation greater than 2 SDs above the plate median (indicated by the continuous line), (b) Proliferation dose responses of 1.10 and 1.78. Error bars, SEM. (n=6) (*P=0.02 and **P=0.007 for 1.10; †P=0.02 for 1.78; all P values from comparison to WT EGF).

To identify EGF mutants with enhanced biological activity, we screened this library at a 10 pM treatment dose, less than that at which WT EGF stimulates cell proliferation. Results from one example plate are shown with on-plate untreated and WT EGF treated controls (FIG. 5a). In this plate, three mutants stimulated proliferation greater than 2 SDs above the plate median (approximately a 50% increase) and were selected for further testing. Two of those candidates, named 1.10 and 1.78 (see Table 1), repeatedly demonstrated improved stimulation of cell proliferation at low doses. Remarkably, dose-response curves reveal that both 1.10 and 1.78 stimulate significant cell proliferation at ~8 (P=0.007 for 1.10 and P=0.02 for 1.78) (FIG. 5b). At this concentration, WT EGF stimulation is equivalent to background. Mutant 1.10 also stimulates significantly higher cell proliferation compared to WT EGF at ~25 pM (P=0.02). Positive identification of enhanced EGF agonists underscores the ability of our platform to screen directly for mutants with improved biological function.

tive EGF mutants we tested. CFPS also enables rapid expression in only a few hours while precisely labeling the proteins with radioactive amino acids. Thus, we can measure the concentration of every protein in the library and treat cells at a uniform dosage. Screening based on specific activity significantly reduces false positives and negatives and increases the ability to detect small improvements in activity.

After CFPS, the protein library can be assessed in cell-based assays as is. No purification or processing was necessary for the three different cell assays we tested. Proteins are also produced in soluble form with no fusions except for an N-terminal methionine to initiate translation, removing the risk of interference in cell signaling and trafficking from additional amino acids or tethered particles. Finally, the protein mutants can be evaluated with any microtiter-plate-based functional assay for agonist and antagonist activity.

It is important to stress the requirement for the product concentration assay and uniform treatment dosage. This is even more critical when imprecise, nonlinear assays are used to detect modest improvements in specific activities. In fact, without incorporating the ability to standardize doses, our discovery of enhanced EGF mutants would have been highly unlikely. In a screen that does not correct for variation in protein expression levels, the only mutants that would be recognized are those that provide increased active expression as well as increased specific activity, an event that is much rarer than increased activity alone.

We validated our platform by screening two EGF mock libraries for the ability to identify EGF variants with differing mitogenic activity. Proteins with higher activity were identified when they represented only a hundredth of the library population. Furthermore, the platform could differentiate between proteins with high, intermediate, and low biological activity. As a complete demonstration, we screened a true EGF library and identified two enhanced agonists, both of which stimulate cell proliferation at concentrations nearly 10-fold lower than those of WT EGF. Several previous attempts have been made to engineer EGF for enhanced stimulation of cell proliferation, but have succeeded only in

TABLE 1

Amino acid sequences of wild-type EGF (SEQ ID NO: 1), mutant 1.10 (SEQ ID NO: 2), and mutant 1.78 (SEQ ID NO: 3). Mutations are underlined in bold type.

| Clone | Sequence |
|---|---|
| EGFwt | NSDSECPLSHDGYCLHDGVCMYIEALDKYACNCVVGYIGERCQYRDLKWWELR |
| 1.10 | NSGSECPLSHDGYCLHDGVCMYIEALDKYACNCVVGYAGERCQYRDLKRWELR |
| 1.7 | NSDSKCPPSHDEYCLHDGVCMYVEALDRYACNCVVGYTGERCQYRDLRWWKLR |

Discussion

We have developed a novel protein evolution platform that enables the direct screening of protein libraries for mutants with improved therapeutic efficacy. Unlike previous techniques, our platform is a general method to evolve proteins using directly relevant bioassays. Libraries can be quickly prepared by PCR without cloning or, if desired, can be adapted from other expression systems, as shown here with a YSD library. Although our CFPS system is based on E. coli, it can produce a broad range of proteins in soluble, active form, as the open environment enables flexible optimization. Furthermore, the addition of IFs expanded the ability of CFPS to express diverse protein libraries, demonstrated by the increase in expression from 80% to 100% of the representaengineering EGF mutants with reduced receptor affinity and equivalent biological activity to that of WT EGF (Reddy, C C et al. (1996) Engineering epidermal growth factor for enhanced mitogenic potency. Nat. Biotechnol., 14, pp, 1696-1699; Coco, W M et al. (2002) Growth factor engineering by degenerate homoduplex gene family recombination. Nat Biotechnol., 20, pp. 1246-1250; Souriau, C et al. (1999) Direct selection of EGF mutants displayed on filamentous phage using cells overexpressing EGF receptor. Biol. Chem., 380, pp. 451-458). None of the previous approaches have demonstrated efficacy at concentrations significantly below that of WT EGF, which is a more meaningful achievement for therapeutic applications. Not only was that achieved by our screen, but we also identified a mutant, 1.10, with a relatively flat stimulation versus dose curve. This assessment suggests that 1.10 would have a broader therapeutic window and be more effective over a range of concentrations, making it ideal for applications such as slow-release formulations.

Besides having potential in wound healing and regenerative medicine, the enhanced EGF agonists we identified could also help illuminate the EGF/EGFR signaling pathway. Despite extensive studies of the EGF/EGFR system, the mechanisms that govern biological potency remain unclear. Many functional characteristics, such as binding affinity, on and off rates, and affinities at low pH, are hypothesized to affect activity, Mutants such as 1.10 and 1.78, which have three and eight nonredundant mutations, respectively (Table 1), will help to identify the principles relating mutations in primary sequence to these functional characteristics, as well as the contributions of these characteristics to overall biological potency. The change in shape from the sigmoidal WT EGF dose-response curve to the flatter 1.10 response is also surprising and suggests a unique mechanism for 1.10's enhanced mitogenic activity. Preliminary data suggest that 1.10 and 1.78 actually have weaker affinities to the EGFR compared to WT EGF. Further characterization of these mutants is ongoing.

Thus, the platform presented here dramatically expands capabilities for evolving proteins beyond previous dependence on binding interactions. In doing so, it also provides new opportunities to investigate sequence-structure-function relationships. The microtiter-plate-based format does impose a limitation on library size. However, this can be partially overcome by the use of robotic systems, and comparable library sizes have been used successfully for many applications including enzyme engineering (Arnold, F H et al. (2001) How enzymes adapt: lessons from directed evolution, Trends Biochem. Sci., 26, pp. 100-106). In addition, the low false-negative and false-positive rates reduce the need for oversampling and multiple screening rounds. As we described, our platform's strongest use may be in combination with a higher-throughput affinity evolution platform, such as phage display or YSD, to initially focus a large library before screening promising candidates for improved biological unction. Certainly, such an approach was important for the success of this study.

Example 2

Characterization of Enhanced EGFR Agonists 1.10 and 1.78

We sought to identify the mechanisms by which mutants 1.10 and 1.78 described in example 1 were able to achieve enhanced activity. We characterized equilibrium binding affinity, pH sensitivity, and on- and off-rates of binding to EGFR We also assessed the EGF and EGFR depletion and correlated receptor depletion with cell proliferation. Finally, we investigated the sequence-structure/function relationships of one enhanced EGF mutant by characterizing the effects of its three point mutations alone and in pairs. Our results support pH sensitivity as key indicators of biological potency. However, contrary to previous reports, we show that this is not solely due to reduced EGFR depletion. In addition, 1.10 and 1.78 have comparable on-rates and faster off-rates compared to wild-type EGF, resulting in a weaker binding affinity. As such, these mutant EGF polypeptides, which have weaker binding affinity but improved biological activity, contradict current hypotheses on the importance of strong binding affinity to promoting biological activity.

Materials and Methods

Expression of Wild-Type EGF and EGF Mutants by Cell Free Protein Synthesis.

Wild-type EGF and mutants 1.10 and 1.78 were previously constructed in the pBL1 plasmid, which contains T7 promoter and terminator elements. Single and double point mutations were performed by the Quikchange site-directed mutagenesis protocol (Stratagene). All templates were confirmed by DNA sequencing (Sequetech, Mountain View, Calif.). The PANOx-SP cell-free system was used for protein expression. CFPS reaction mixtures were composed of the following: 20 mM magnesium glutamate, 10 mM ammonium glutamate, 175 mM potassium glutamate, 1.2 mM ATP, 0.86 mM each of CTP. GTP and UTP, 10 mM potassium phosphate, 34 µg/mL folinic acid, 170 µg/mL $E.$ $coli$ tRNAs, 33 mM phosphoenol pyruvate, 1.5 mM spermidine, 1 mM putrescine, 0.33 mM NAD, 0.27 mM coenzyme A, 2.7 mM sodium oxalate, 2 mM each of the 20 unlabeled amino acids, 100 µg/mL T7 RNAP, 4 mM oxidized glutathione (GSSG), 1 mM reduced glutathione (GSH), 100 µg/mL DsbC, 100 µg/mL Gam, and 0.24 v/v of $E.$ $coli$ KC6 S30 extract. Protein was radiolabeled by adding 5 µM of L-[U-14C]-Leucine (Perkin Elmer). To encourage formation of disulfide bonds, KC6 extract was pre-treated with 1 mM iodoacetamide (IAM) for 30 min at room temperature. After preparation, all CFPS reaction mixtures were incubated at 37° C. for 3 hours. Standard reactions from a plasmid template were performed in 30 µl volume and contained 53.3 µg/ml DNA. Protein concentrations were measured by spotting 4 µl of the CFPS reactions on individual filter papers, washing the papers in ice-cold 5% trichloroacetic acid (TCA), and performing scintillation counting. Expression of a single product at the correct molecular weight was verified by SDS-PAGE and autoradiography.

Cell Culture

BJ5ta Cells.

BJ5ta cells (ATCC CRL-4001) were propagated in complete medium: DMEM supplemented with 20% (v/v) Medium 199, 1% penicillin-streptomycin, 1% L-glutamine, 1% sodium pyruvate, 10% fetal bovine serum, and 10 µg/mL hygromycin B selective agent. All cell culture reagents were purchased from Gibco unless otherwise noted. Cells were grown in a humidified incubator at 37° C. and 5% CO2. Frozen cell aliquots were thawed and cultures in the absence of selective agent for 24 h prior to medium renewal and addition of hygromycin B. Cell cultures were passaged once cells reached 70-80% confluency (after approximately 3 days). Prior to use in biological assays. BJ-5ta cells were grown in serum-free medium (identical to the medium detailed above but without hygromycin B and fetal bovine serum) for 48 hr.

NR6WT Cells.

NR6WT cells were propagated in complete medium: MEMα supplemented with 1% (v/v) penicillin-streptomycin, 1% L-glutamine, 1% sodium pyruvate, 1% MEM nonessential amino acids, 7.5% fetal bovine serum, and 350 µg/mL G418 selective agent. All cell culture reagents were purchased from Gibco unless otherwise noted. Cells were grown in a humidified incubator at 37° C. and 5% CO2. Frozen cell aliquots were thawed and grown for 24 h in the absence of selective agent prior to medium renewal and addition of G418. Cells were passaged once cultures reached 70-80% confluency (after approximately 3 days). Prior to use in biological assays, cells were grown in serum-free medium for 24 hr. Serum-free medium is identical to the complete medium detailed above, but without fetal bovine serum and G418 and supplemented with 1% dialyzed FBS (Invitrogen).

On-Cell Competition Binding.

BJ5ta and NR6WT cells were cultured as described. With no serum starvation, cells were removed from tissue culture plates with 0.05% trypsin-EDTA. After neutralization with complete medium, cells were centrifuged and resuspended in ice-cold PBS with 1 mg/ml BSA (PBS/BSA) at a concentration of 25,000 cells and 50,000 per 50 µl for BJ5ta and NR6WT, respectively. Equal volume of PBS/BSA with 200 µM phenylarsine oxide (PAO) was added and cells were incubated for 20 min at 4° C. 100 µl of the cell mixture was then aliquoted into separate sterile round-bottom polystyrene tubes (Falcon) and immediately diluted with ice cold 1 mL PBS/BSA. Cells were then spun at 1000 RPM for 5 min at 4° C. and buffer was decanted (all future washes were performed under these conditions). Cells were resuspended in ice-cold 800 µl PBS/BSA. 100 µl of 10× concentrated EGF produced by CFPS was then added and cells were incubated at 4° C. with gentle shaking for 30 min. 100 µl of 5 nM FLAG-tagged wild-type EGF produced in yeast was then added as a competitor. Cells were incubated for an additional 6 hr at 4° C. with gentle shaking. As a negative control, no FLAG-tagged EGF was added. As a positive control, no CFPS EGF was added.

The amount of FLAG-tagged EGF bound to the cells was measured by flow cytometry using a FACSCalibur flow cytometer (Becton Dickinson) and analyzed using FlowJo software (Tree Star). EGF binding was detected by labeling cells with a mouse anti-FLAG antibody conjugated to R-phycoerytherin (Prozyme PJ315) in a 50 µl volume and final concentration of 10 µg/ml, Cells were then washed by adding 1 mL PBS/BSA as before and stored on ice for analysis by flow cytometry. Data was plotted and fitted to calculate IC50s using KaleidaGraph software (Synergy Software).

pH Sensitivity.

BJ5ta cells were cultured as described. With no serum starvation, cells were removed from tissue culture plates with 0.05% trypsin-EDTA. After neutralization with complete medium, cells were centrifuged and resuspended in ice-cold PBS with 1 mg/ml BSA (PBS/BSA) at a concentration of 25,000 cells per 50 µl. Equal volume of PBS/BSA with 200 µM phenylarsine oxide (PAO) was added and cells were incubated for 20 min at 4° C. 100 µl of the cell mixture was then aliquoted into separate sterile round-bottom polystyrene tubes (Falcon) and immediately diluted with ice-cold 1 mL PBS/BSA. Cells were then spun at 1000 RPM for 5 min at 4° C. and buffer was decanted (all future washes were performed under these conditions). Cells were resuspended in 100 µl PBS/BSA with 100 nM of the indicated EGF produced by CFPS. Cells were incubated at 4° C. with gentle shaking for 4 hours. Cells were washed and incubated with 100 µl of ice-cold citrate-phosphate buffer at the desired pH for 5 min with gentle shaking. Cells were then washed again and free (unliganded) EGFR was labeled with 50 µl of 100 nM FLAG-tagged wild-type EGF produced in yeast, Cells were incubated for 15 min at 4° C. with gentle shaking. The amount of FLAG-tagged EGF bound to the cells was measured by flow cytometry using a FACSCalibur flow cytometer (Becton Dickinson). EGF binding was detected by labeling cells with a mouse anti-FLAG antibody conjugated to R-phycoerytherin (Prozyme PJ315) in a 50 µl volume and final concentration of 10 µg/ml. Cells were then washed by adding 1 mL PBS/BSA as before and stored on ice for analysis by flow cytometry. Negative controls (no FLAG-tagged EGF) and positive controls (no CFPS EGF) were included with every experiment.

EGFR Depletion.

BJ5ta cells were seeded into 6-well tissue culture plates with 2 mL complete medium without selection agent at densities of 25,000 cells/well. After 24 h, the complete medium was aspirated, the cells were washed with PBS, and 2 mL serum-free medium was added to each well. Cells were serum starved for 48 h. The medium was aspirated and serum-starved cells were treated with 2 mL of wild-type or mutant EGF in serum-free medium at indicated concentrations and incubation times. For dose responses, serial dilutions of 1:10 were prepared and cells were treated for 4 hours. Following treatment, the medium was aspirated, cells were washed with 2 mL PBS, and then detached from the tissue culture plate using 0.05% Trypsin-EDTA (Gibco). The trypsinization reaction was quenched with 2 mL serum-free medium supplemented with 1% (w/v) bovine serum albumin and the cell suspension mixture was transferred to a sterile roundbottom polystyrene tube (Falcon). Paraformaldehyde (PFA) was added to the cell suspension to a final concentration of 1.5% (v/v) and the suspension mixture was vortexed and incubated at room temperature for 10 min. The fixed cells were washed with 1 mL PBS, pelleted by centrifugation at 2000 RPM for 5 min, and resuspended in 100 µL PBS with 1 mg/ml BSA. (PBS/BSA). Fixed cells were stored at 4° C. prior to analysis by flow cytometry.

The amount of EGFR remaining on cell surface after treatment with wild-type or mutant EGF was measured by flow cytometry using a FACSCalibur flow cytometer (Becton Dickinson). Primary antibody (clone 199.12, Lab Vision) directed against the extracellular domain of EGFR was added to fixed cells at a final concentration of 5 µg/mL in PBS/BSA and incubated at 4° C. for 30 min. Cells were washed with 1 mL ice-cold PBS/BSA and pelleted by centrifugation. Cells were resuspended in 50 µL PBS/BSA with secondary goat anti-mouse R-phycoerytherin antibody (Sigma, 1:50 dilution) and then incubated at 4° C. with shaking for 30 min. Cells were washed with PBS/BSA as before and stored on ice for analysis by flow cytometry.

A second primary antibody (clone 225) against the extracellular domain of EGFR was used to confirm the EGFR depletion results. Experiments were performed as described above with two exceptions. 1) Clone 225 competes with EGF binding to EGFR. Thus, before the cells were fixed with PFA, they were incubated with 200 µL of citrate-phosphate buffer pH 3.5 for 5 min to strip any bound EGF from the cells. The cells were then washed by adding 1 mL PBS/BSA, pelleted by centrifugation at 2000 RPM for 5 min, and resuspended in PFA. 2) Cells were labeled with clone 225 at a final concentration of 10 µg/ml.

EGF Depletion.

BJ5ta cells were plated in 10 cm tissue culture dishes in 10 mL of complete medium and cultured until approximately 70% confluent. The cells were then washed with PBS and incubated in serum-free media. After 48 hrs, the cells were incubated in serum-free media containing 1 mg/ml BSA and indicated concentrations of wild-type EGF or mutant 1.10 (Note: all dilutions of EGF were also performed in serum-free media containing 1 mg/ml BSA to prevent loss due to non-specific adsorption). EGF with high specific radioactivity was produced by CFPS as described above except that the concentration of unlabeled amino acids was decreased to 0.1 mM and the concentration of 14C-labeled leucine was increased to 40 µM. At the indicated timepoints, 9 mL of the cell medium was removed and transferred to 50 mL conical falcon tubes (Corning). Medium was cooled on ice and protein was precipitated by addition of 1 mL 100% trichloroacetic acid (TCA) and incubation for 30 min at 4° C. Precipitated protein was pelleted by centrifugation at 10,000 RPM for 15 min at 4° C. The pellet was washed once with ice-cold 5% TCA, vortexed, and centrifuged again as before. The pellet was then resuspended in 5 mL scintillation fluid. Vortexing and pipette mixing was used to break up the pellet. The scintillation fluid was then decanted into scintillation vials for counting. For each experiment, a blank CFPS reaction mixture was diluted equivalently to EGF and precipitated in parallel to measure background counts. Background counts were subtracted from all the readings. Positive controls with wild-type EGF incubated without cells at 4° C. and 37° C. were also included in the experiments to illustrate that EGF was not lost due to nonspecific absorption or degradation.

Cell Proliferation.

BJ5ta cells were plated in 96-well plates at densities of 2,500 cells/well (BJ5ta), in 100 µl of complete medium. After 24 hr, cells were serum-starved for 48 hr (BJ5ta). The medium was then replaced with 100 µl of serum-free medium containing serial dilutions of growth factors. After an additional 48 hr, 1 µCi of 3H-TdR (GE Healthcare) was added to each well in 50 µl of serum-free medium. 3H-TdR incorporation was measured 24 h later by freezing the cells overnight at −80° C. and harvesting the cells onto glass fiber filtermats (Perkin Elmer) using a Mach IIIM harvester (Tomtec). Filtermats were dried for at least three hours in a dry incubator or overnight on the bench and scintillation counting was performed with a Wallac MicroBeta (Perkin Elmer).

Cell Migration.

Costar transwells (Corning 3422, 8.0 µm pores, 6.5 mm diameter) were coated on both sides with 10 µg/ml bovine fibronectin (Sigma F1141-2MG, 1 mg/ml) overnight at 4° C. in buffer (50 mM Tris-HCl, 500 mM NaCl, pH 7.5), Tranwells were then washed 3 times with PBS, and then blocked with PBS with 1% BSA (PBS/BSA) at 37° C. for 1 hr prior to usage. 2.5×105 BJ5ta cells in 200 µl of serum-free medium with 1% BSA were placed into the upper chamber of coated transwells and allowed to migrate toward the lower chamber media containing 800 µl of the indicated concentration of EGF for 3 hr under tissue culture conditions. Non-migrated cells were removed by wiping the upper side of the membrane with Q-tips. The transwells were washed three times with PBS, fixed by adding 1 mL methanol to the lower chamber for 15 min at room temperature, and stained with modified Giemsa (Sigma GS500) diluted 1:20 with Milli-Q water by adding 1 to the lower chamber for 1 hr at room temperature. Pictures were taken of the migrated-stained cells in nine random high-powered fields (20×) using light microscopy, and the number of migrated cells was counted using ImageJ software.

Direct Cell Binding Assays.

For the equilibrium binding titrations of EGF to EGFR, BJ-5ta human fibroblast cells were pretreated for 20 min with 100 µM phenylarsine oxide to inhibit EGFR internalization. Then equilibrium receptor binding affinities were measured after incubation with EGF for 6 hours at 4° C. Cells were labeled with a FITC-conjugated antibody directed against an N-terminal FLAG epitope tag on EGF and analyzed using a Guava easyCyte flow cytometer (Millipore). Mean fluorescence values of cell binding were obtained, and data was fit using KaleidaGraph (Synergy Software).

Cell surface measurements of EGFR binding off-rates Receptor binding off-rates were measured using BJ-5ta cells pretreated for 20 min with 100 µM phenylarsine oxide to inhibit EGFR internalization, Cells were incubated with 25 nM EGF for 10 min at 37° C. washed, and incubated in phosphate buffered saline at 4° C. for various times. The level of EGF persisting on the cell surface was detected by a FITC-conjugated antibody directed against an N-terminal FLAG epitope tag on. EGF and analyzed using a Guava easyCyte flow cytometer (Millipore). Mean fluorescence values of cell binding were obtained, and data was fit using KaleidaGraph (Synergy Software).

EGFR Activation and Immunoblotting.

BJ-5ta fibroblasts were incubated with EGF (five-fold dilutions from 20 nM to 6.4 pM) for 15 min at 37° C. Cells were treated with NP-40 lysis buffer supplemented with protease and phosphatase inhibitors, Cell lysates were resolved by SDS-PAGE under reducing conditions and analyzed by western blot with primary antibodies directed against actin or phosphorylated or total EGFR and a horseradish peroxidase-conjugated secondary antibody, Western blots were developed using chemiluminescence and imaged using a Chemidoc System (BioRad).

Results

EGF Mutants T10 and T78 have Weaker Binding Affinity to EGFR.

Figure 11:
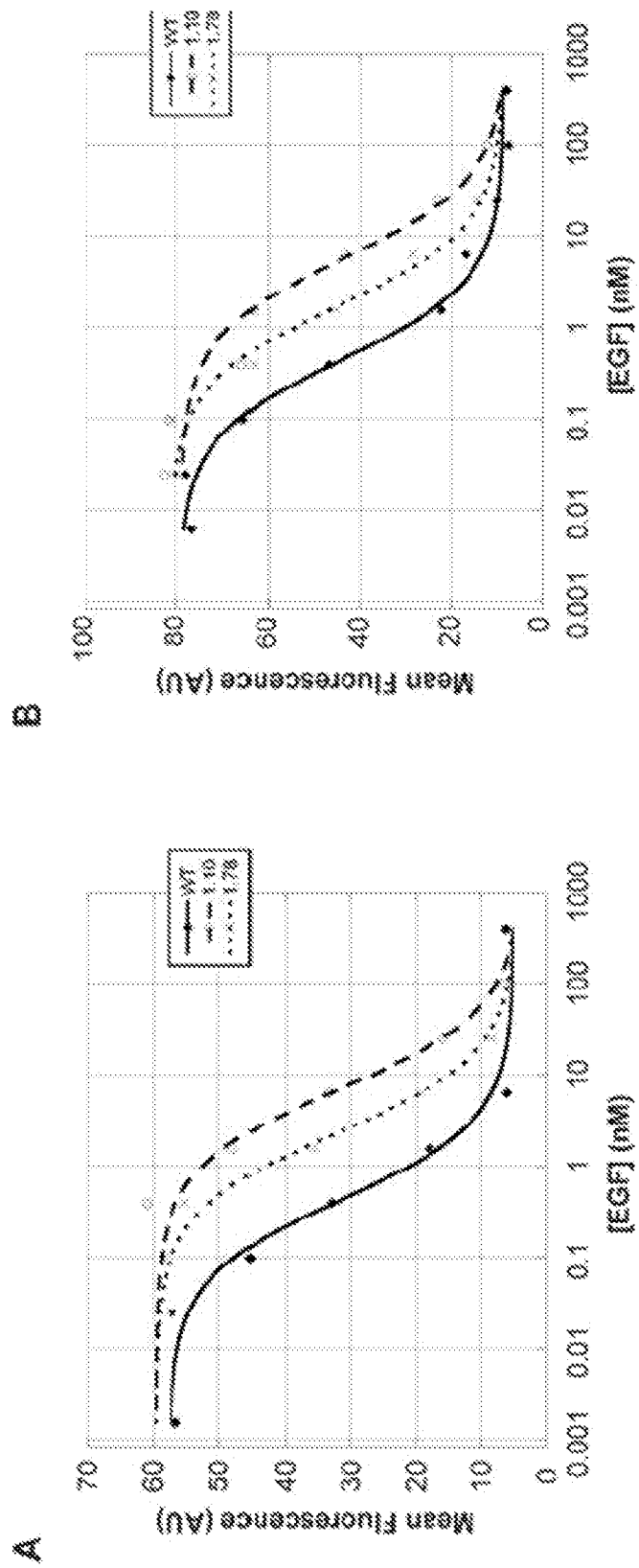
FIG. 11. Competition binding of wild-type EGF and mutants 1.10 and 1.78 on fibroblast cells FLAG-tagged EGF expressed and purified from *S. cerevisiae* was competed off of (A) BJ5ta and (B) NR6WT cells by varying concentrations of wild-type EGF (WT) and mutants 1.10 and 1.78 expressed by CFPS. Three independent experiments were performed. Representative data are shown.

We first characterized the equilibrium binding of EGF mutants T10 ("1.10", SEQ ID NO:2) and T78 ("1.78", SEQ ID NO:3) to EGFR. Wild-type EGF and mutants 1.10 and 1.78 were expressed by cell-free protein synthesis (CFPS). They were produced without epitope tags to prevent any possible interference in binding to EGFR. Thus, to measure their binding to EGFR on the cell surface, we performed competition binding assays using FLAG-tagged EGF expressed and purified from *S. cerevisiae* (Y-EGF). BJ5ta human fibroblast cells were incubated with varying concentrations of wild-type EGF and mutants 1.10 and 1.78 and a constant concentration of Y-EGF for six hours. To prevent EGFR internalization, we kept the cells at 4° C. and pretreated them with the phosphatase inhibitor phenylarsine oxide (PAO). Cells were then labeled with a fluorescently-labeled antibody against the FLAG epitope tad and analyzed by flow cytometry. We found that EGF mutants 1.10 and 1.78 have approximately 15- and 6-fold weaker binding affinity to EGFR, respectively, compared to wild-type EGF (FIG. 11 and Table 2). Identical results were also measured with NR6WT cells, a mouse fibroblast cell line devoid of mouse EGFR that has been transfected to express human EGFR.

TABLE 2

Half-maximal inhibitory concentrations from competition binding on fibroblast cells. Competition binding experiments were performed on BJ5ta and NR6WT cells to compare the relative binding affinities of wild-type EGF and mutants 1.10 and 1.78. Three independent experiments were performed with three different batches of EGF protein. Inhibition curves, representing competition binding of FLAG-tagged EGF, were fit using KaleidaGraph software and the average and standard deviations of the half-maximal inhibitory concentrations (IC50 values) are given.

| Ligand | IC50 (nM) | |
|---|---|---|
| | BJ5ta cells | NR6WT cells |
| Wild-type EGF | 0.4 ± 0.1 | 0.5 ± 0.3 |
| Mutant 1.10 | 7 ± 2 | 6 ± 2 |
| Mutant 1.78 | 2.3 ± 0.3 | 3 ± 1 |

EGF Mutants 1.10 and 1.78 Weaker Binding Affinity to EGFR is Mediated by a Faster Off-Rate of Binding.

Figure 12:
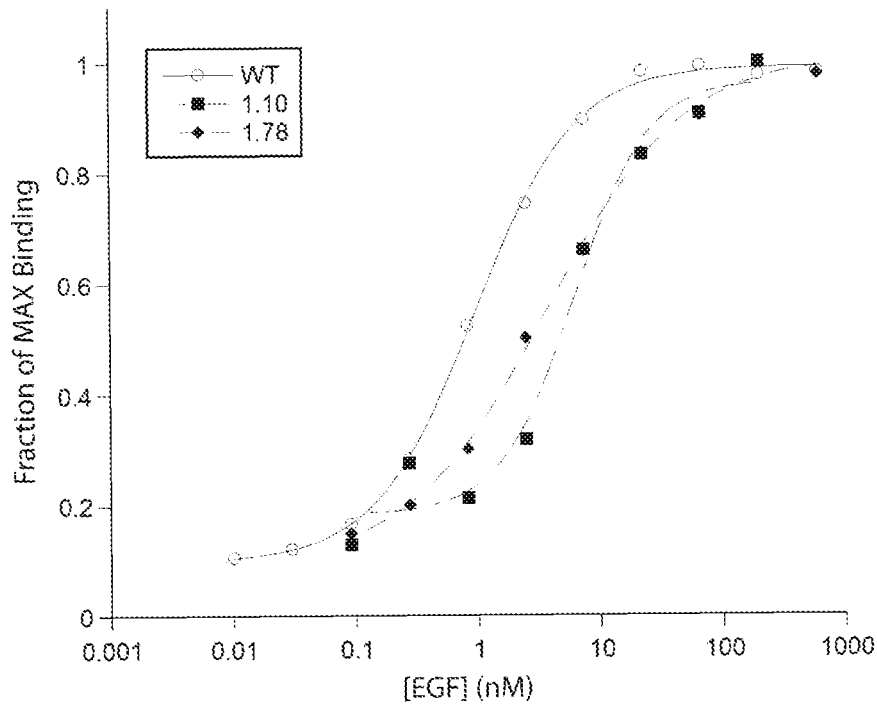
FIG. 12. Binding of wild-type EGF (open circles, solid line), 1.10 (black diamonds, dashed line), and 1.78 (black squares, double dashed line) to EGFR expressed on the cell surface. This figure shows equilibrium binding titrations of EGF to EGFR on BJ-5ta human fibroblast cells pretreated for 20 min with 100 µM phenylarsine oxide to inhibit EGFR internalization. Equilibrium receptor binding affinities were measured after incubation with EGF for 6 hours at 4° C. Cells were labeled with a FITC-conjugated antibody directed against an N-terminal FLAG epitope tag on EGF and analyzed using a Guava easyCyte flow cytometer (Millipore).
Figure 13:
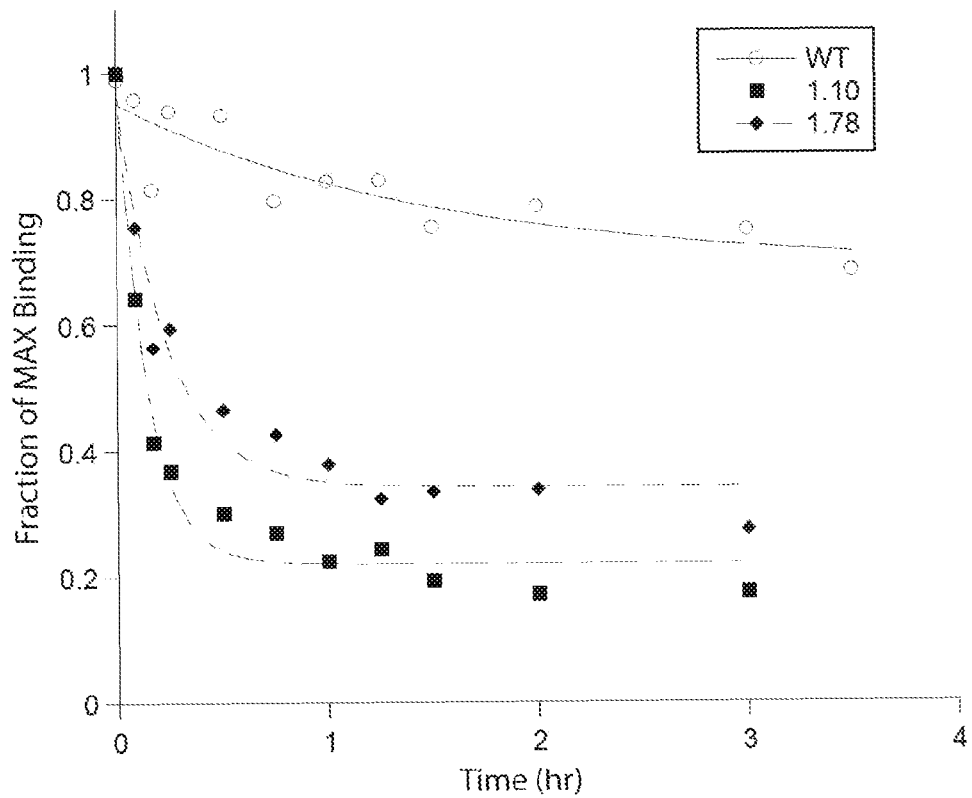
FIG. 13. Off-rates of EGF binding to EGFR on BJ5Tα cells. EGFwt (open circles, solid line), 1.10 (black diamonds, dashed line), and 1.78 (black squares, double dashed line). Receptor binding off-rates were measured using BJ-5ta cells pretreated for 20 min with 100 µM phenylarsine oxide to inhibit EGFR internalization. Cells were incubated with 25 nM EGF for 10 min at 37° C., washed, and incubated in phosphate buffered saline at 4° C. for various times. The level of EGF persisting on the cell surface was detected by a FITC-conjugated antibody directed against an N-terminal FLAG epitope tag on EGF and analyzed using a Guava easyCyte flow cytometer (Millipore).

We further characterized the equilibrium binding of EGF mutants 1.10 (SEQ ID NO:2) and l78 (SEQ ID NO: 3) to EGFR. In this case, wild-type EGF and mutants 1.10 and 1.78 were recombinantly expressed in *S. cerevisiae* as described in Cochran at al PEDS 2006. These EGF proteins contained an N-terminal FLAG tag and a C-terminal hexahistidine tag, allowing direct binding of EGF to cell surface EGFR to be measured by flow cytometry using an FITC-conjugated anti-FLAG antibody. BJ5ta human fibroblast cells were incubated with varying concentrations of wild-type EGF and mutants 1.10 and 1.78 for 6 hr at 4° C. To prevent EGFR internalization, cells were incubated at 4° C. and pre-treated with the phosphatase inhibitor phenylarsine oxide (PAO). We found that EGF mutants 1.10 and 1.78 had weaker binding affinity to EGFR ($K_D$=6 nM and 4 nM, respectively), compared to wild-type EGF ($K_D$=1 nM). (FIG. 12). Receptor binding off-rates were measured using BJ-5ta cells pretreated with PAO. Cells were incubated with 25 nM EGF for 10 min at 37° C., washed, and incubated in phosphate buffered saline at 4° C. for various times, and binding was measured as above. Mutants 1.10 and 1.78 exhibited faster off-rates of binding ($2\times10^{-3}$ s$^{-1}$ and $1\times10^{-3}$ s$^{-1}$, respectively) compared to wild-type EGF ($2\times10^{-4}$ s$^{-1}$) (FIG. 13). Kinetic on-rates of binding were calculated from $K_D=k_{off}/k_{on}$, and were similar for wild-type EGF, 1.10, and 1.78. See Table 3 below.

TABLE 3

| Ligand | $K_D$ (nM) | $K_{off}$ (s$^{-1}$) | $K_{on}$ (M$^{-1}$ s$^{-1}$) (calculated) |
|---|---|---|---|
| Wild-type EGF | 1 | 2E−04 | 2E+05 |
| Mutant 1.10 | 6 | 2E−03 | 3E+05 |
| Mutant 1.78 | 4 | 1E−03 | 3E+05 |

EGF Mutants 110 and 1.78 are pH Sensitive

Figure 14:
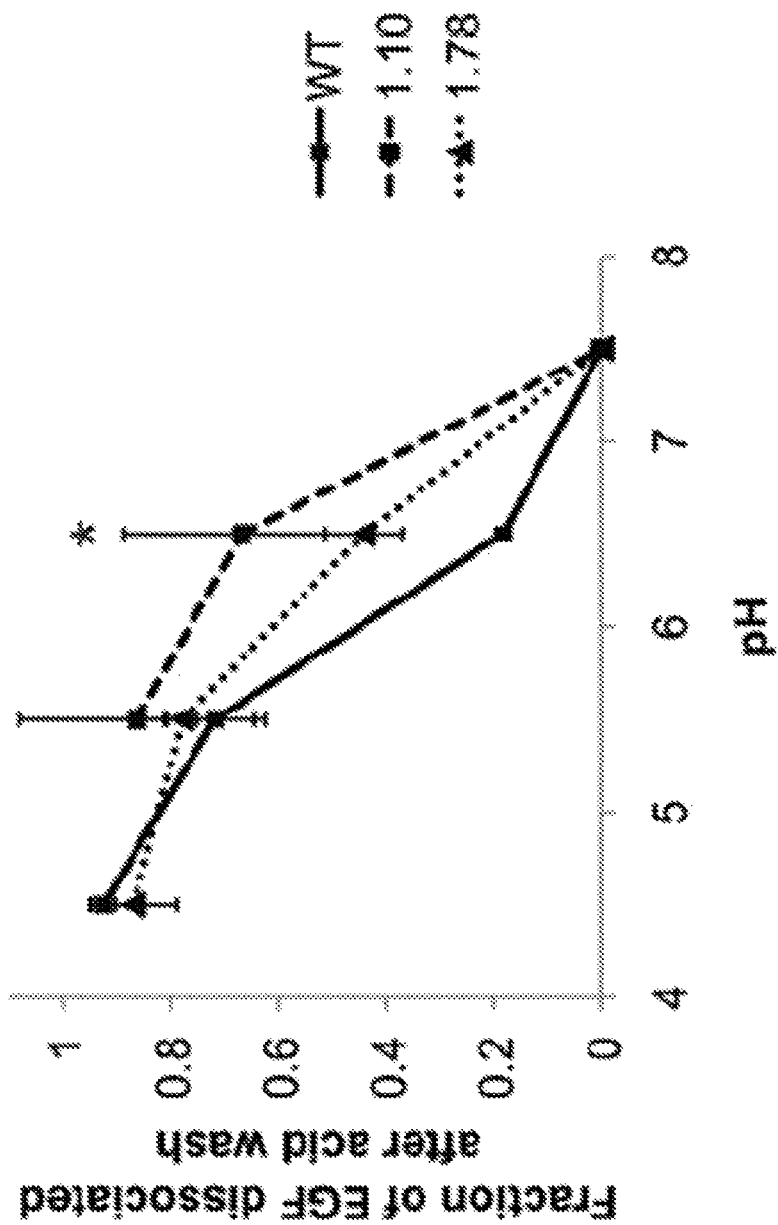
FIG. 14. pH sensitivity of wild-type EGF and mutants 1.10 and 1.78 binding to EGFR on the cell surface. The amount of wild-type EGF (WT) and mutant 1.10 and 1.78 that dissociated after a 5 min wash with varying pH buffers was measured by labeling with Y-EGF and flow cytometry. Data represents average and standard deviation of independent experiments (n=3 for wild-type EGF and mutant 1.10; n=2 for mutant 1.78; *P=0.02 for mutant 1.10 compared to wild-type EGF).

A second aspect of binding that can have a significant effect on biological efficacy is pH sensitivity. The level of binding at endosomal pH can determine the fraction of EGF and EGFR that is trafficked back to the cell surface or to lysosomes for degradation (French, A. R., et al., Intracellular trafficking of epidermal growth factor family ligands is directly influenced by the pH sensitivity of the receptor/ligand interaction. J Biol Chem, 1995. 270(9): p. 4334-40: Reddy, C. C., et al., Engineering epidermal growth factor for enhanced mitogenic potency. Nat Biotechnol, 1996. 14(13): p. 1696-9; Maeda, K. et al. pH-dependent receptor/ligand dissociation as a determining factor for intracellular sorting of ligands for epidermal growth factor receptors in rat hepatocytes. Control Release, 2002, 82(1): p 71-8: Sarkar, C. A., et al., Rational cytokine design for increased lifetime and enhanced potency using pH-activated "histidine switching". Nat Biotechnol, 2002. 20(9): p. 908-13). For example, fast dissociation of transforming growth factor α (TGFα) at low pH is believed to contribute to its enhanced activity under ligand-limiting conditions (French. A. R., et al., Intracellular trafficking of epidermal growth factor family ligands is directly influenced by the pH sensitivity of the receptor/ligand interaction. J Biol Chem, 1995. 270(9): p. 4334-40; Reddy, C. C., A. Wells, and D. A. Lauffenburger, Comparative mitogenic potencies of EGF and TGF alpha and their dependence on receptor-limitation versus ligand limitation. Med Bid Eng Comput, 1998. 36(4): p. 499-507). To investigate if mutants 1.10 and 1.78 exhibited greater pH sensitivity than wild-type EGF, we incubated BJ5ta cells with saturating concentrations of EGF for four hours at 4° C. We then briefly washed the cells with varying pH buffers and labeled them with FLAG-tagged Y-EGF followed by a fluorescently-labeled antibody against the FLAG epitope tag. Cells were analyzed by flow cytometry, and the level of Y-EGF binding indicated the amount of EGF that dissociated during the acid washes, We found that both mutants 1.10 and 1.78 were more pH sensitive than wild-type EGF, with significantly more mutant 1.10 than wild-type EGF dissociating during only a five minute incubation at pH 6.5 (70% for mutant 1.10 compared to 20% for wild-type EGF, P=0.02) (FIG. 14). The larger error bars for mutant 1.10 reflect the higher variability of the assay due to its weaker binding affinity.

EGF Mutants 1.10 and 1.78 Reduce Depletion of Cell Surface EGFR.

After EGF binding, EGFR is rapidly internalized by the cell and is trafficked for recycling or degradation. The amount of EGF that remains bound to EGFR influences the sorting process. Free receptors are more likely to be shuttled back to the cell surface and become available for another round of activation and signaling (Roepstorff, K., et al., Differential effects of EGFR ligands on endocytic sorting of the receptor. Traffic, 2009. 10(8): p. 1115-27; Wiley, H. S., Trafficking of the ErbB receptors and its influence on signaling. Exp Cell Res, 2003. 284(1): p. 78-88), Our results above indicated that mutants 1.10 and 1.78 had increased pH sensitivity compared to wild-type EGF. We hypothesized this could result in reduced degradation of EGFR and higher levels of EGFR remaining at the cell surface, explaining the improved, biological activities of the mutants.

Figure 15:
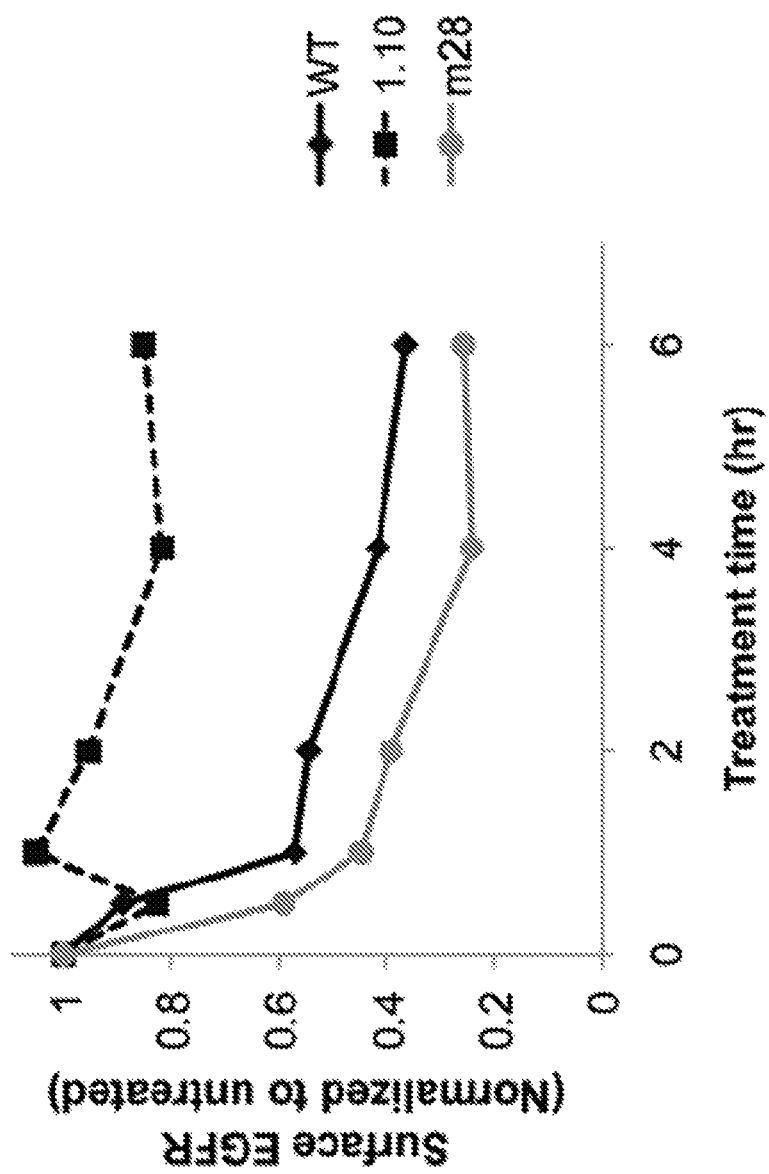
FIG. 15. Time-course of cell surface EGFR depletion after treatment with wildtype EGF and EGF mutants 1.10 and m28. BJ5ta cells were treated with 0.1 nM of wild-type EGF (WT) and mutants 1.10 and m28 and the levels of surface EGFR were measured by flow cytometry at various timepoints. EGFR levels were normalized to untreated controls analyzed in parallel at each timepoint.

To compare the levels of EGFR depletion from the cell surface, we treated serum starved BJ5ta fibroblast cells with wild-type EGF and mutant 1.10 at a single concentration (0.1 nM). We measured the amount of surface EGFR at different timepoints by labeling cells with a primary antibody (clone 199.12) against the EGFR extracellular domain and a fluorescently-labeled secondary antibody and analyzing the cells by flow cytometry (FIG. 15). As a positive control, we also treated cells with previously identified EGF mutant m28 (see example 4), which stimulates more EGFR depletion than wild-type. We found that mutant 1.10 stimulated very low levels of EGFR depletion (surface EGFR levels at 85% of untreated controls) even after six hours. In contrast, treatment with wild-type EGF and mutant m28 reduced surface EGFR levels to 35% and 25% of untreated controls, respectively.

Figure 16:
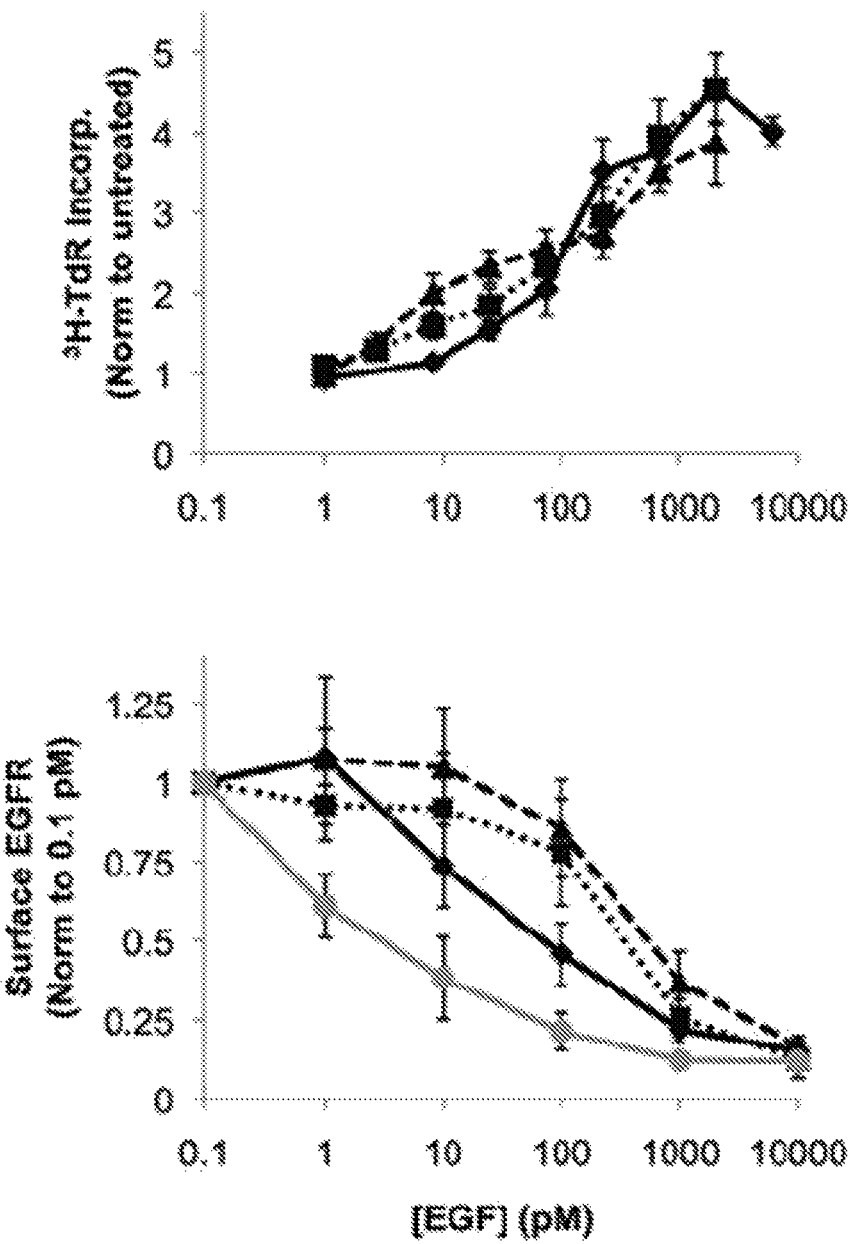
FIG. 16. Cell proliferation and EGFR depletion after treatment with wild-type EGF and EGF mutants in BJ5ta cells treated with varying concentrations of wild-type EGF (WT) and mutants 1.10, 1.78, and m28. The level of cell proliferation was measured by 3H-thymidine incorporation (3H-TdR) and the level of surface EGFR was measured by labeling with antibodies to EGFR and analyzing by flow cytometry. Cell proliferation data is the average and standard error of six experiments on four days, each individually normalized to background incorporation. EGFR depletion data is the average and standard deviation of three independent experiments.
Figure 17:
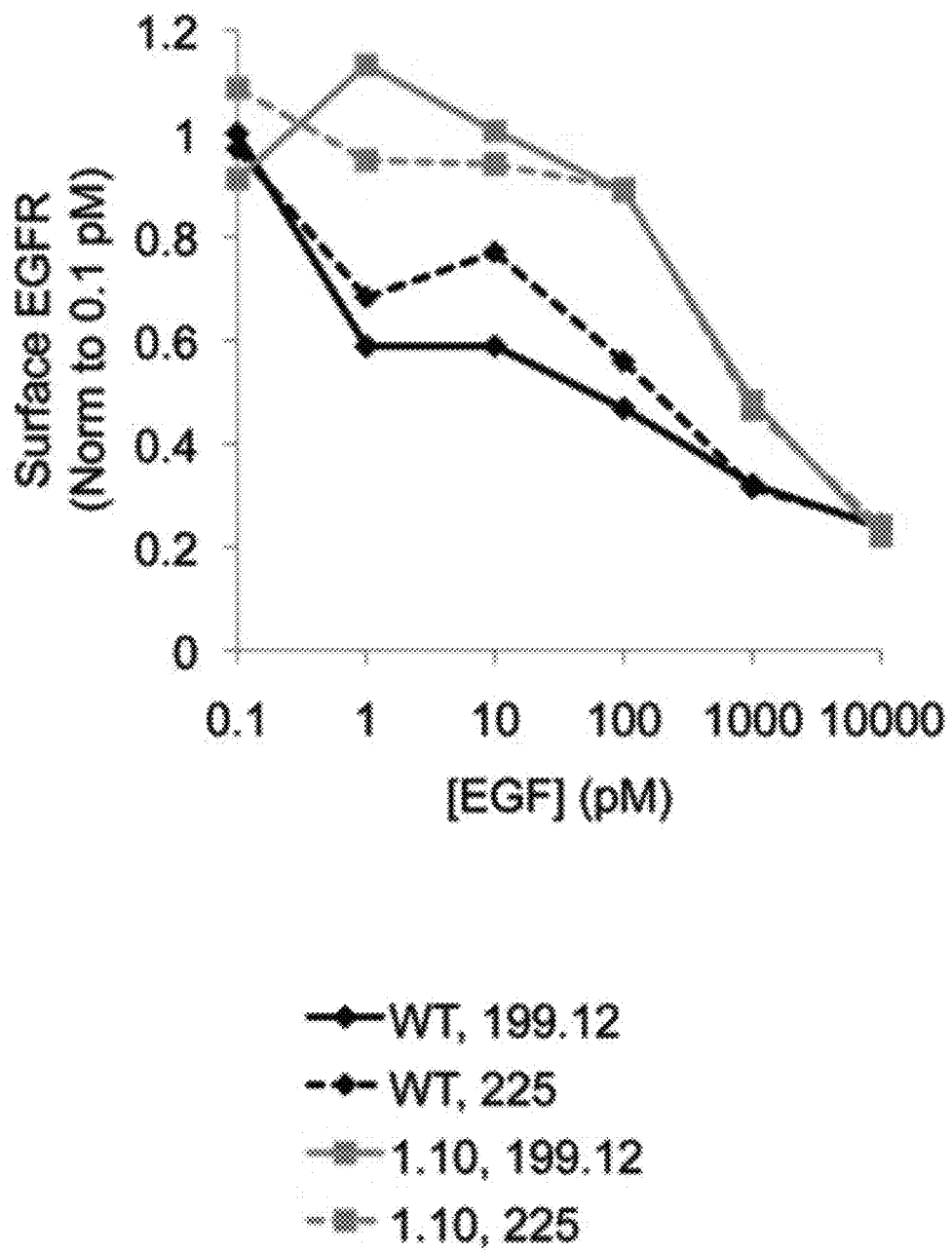
FIG. 17. Comparison of EGFR depletion after treatment with wild-type EGF and mutant 1.10 using two EGFR antibodies. The EGFR depletion results for mutant 1.10 using EGFR antibody clone 199.12 were confirmed by comparison with a second competitive EGFR antibody (clone 225). Surface EGFR levels measured by the two antibodies were within experimental error.

We explored the differences in EGFR depletion further by comparing the steady-state levels of cell surface EGFR after treatment with varying concentrations of EGF. We treated serum-starved BJ5ta cells with different concentrations of wild-type EGF and mutants 1.10, 1.78, and m28 for four hours. We then labeled the cells and analyzed them by flow cytometry (FIG. 16), in agreement with the time-course experiment above, we found that m28 stimulates significantly more EGFR depletion than wild-type EGF. Even after treatment with only 1 pM, m28 resulted in a 40% reduction in surface EGFR levels—a significant difference from wild-type EGF which stimulated almost no depletion at 1 pM (P=0.002). The titration of EGF concentrations revealed that both mutants 1.10 and 1.78 stimulated less EGFR depletion than wild-type EGF. Treatment with 10 pM of wild-type EGF lowered surface EGFR expression to 80% of background levels while 10 pM of mutants 1.10 and 1.78 did not appear to stimulate any EGFR depletion. This difference became most significant after treatment with 100 pM of EGF. Wild-type EGF resulted in EGFR depletion to less than 50% of original levels while mutants 1.10 and 1.78 maintained surface EGFR levels at around 80% (P=0.01 comparing wild-type EGF and mutant 1.10; P=0.03 comparing wildtype EGF and mutant 1.78). These results were also confirmed using a second primary antibody to EGFR (clone 225) (FIG. 17). Unlike clone 199.12, this antibody competes with EGF binding to EGFR, and a brief acid strip was used to remove any EGF bound to the cells.

These results indicated that mutants 1.10 and 1.78 might enhance cell proliferation by reducing depletion of EGFR from the cell surface. The difference between cellular responses to treatments with wild-type EGF and mutants 1.10 and 1.78 became even more distinct when cell proliferation and EGFR depletion were directly compared (FIG. 16). Wild-type EGF stimulated depletion of EGFR at lower concentrations than at which it stimulated cell proliferation, This order was reversed for mutants 1.10 and 1.78. Both mutants 1.10 and 1.78 stimulated cell proliferation at lower concentrations than at which they induced EGFR depletion. This switch suggested that mutants 1.10 and 1.78 substantially alter the internalization and trafficking of EGFR after ligand binding.

EGF Mutant 1.10 is not Depleted from the Cell Medium.

In addition to depletion of receptors, internalization and degradation can also cause significant depletion of ligand. The mechanism by which mutant 1.10 reduced levels of EGFR depletion might also prevent depletion of ligand from the cell medium. To measure ligand depletion, we produced 14C-labeled wild-type EGF and mutant 1.10 by CFPS with high specific radioactivity (greater than 1 cpm μl-1 nM-1). Serum-starved BJ5ta fibroblast cells were incubated under tissue culture conditions with serum-free medium containing 10 or 100 pM EGF. To prevent loss of EGF duo non-specific absorption to tube and plate surfaces, the medium was supplemented with 1 mg/ml bovine serum albumin (BSA). At indicated times, the cell medium was removed, and full-length EGF was precipitated by addition of trichloroacetic acid (TCA) to a final concentration of 10% w/v and incubation at 4 for 30 min. Here, the BSA in the medium also acted as a carrier protein to aid protein precipitation and formed a visible white precipitate. Precipitated protein was then pelleted by centrifugation, washed once with ice-cold 5% TCA, and measured by scintillation counting.

Figure 18:
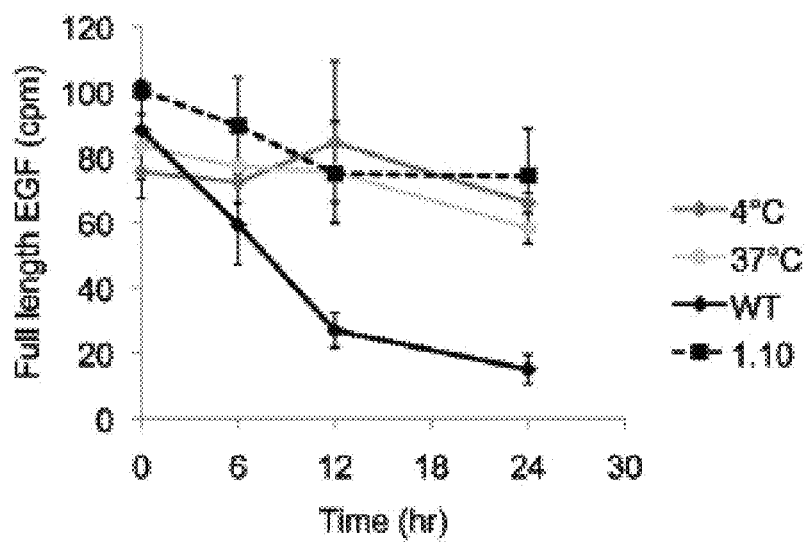
FIG. 18. Depletion of wild-type EGF and mutant 1.10 from cell medium. BJ5ta fibroblast cells were incubated with serum-free medium containing 1 mg/ml BSA and (A) 10 pM or (B) 100 pM 14C-labeled wild-type EGF (WT) and mutant 1.10. At different times, the amount of full length EGF remaining in the cell medium was measured by precipitating the protein with 10% trichloroacetic acid and performing scintillation counting. Positive controls of wild-type EGF incubated without cells at 4° C. and 37° C. were included. Data represents average and standard deviations of triplicate experiments performed on two different days.
Figure 18:
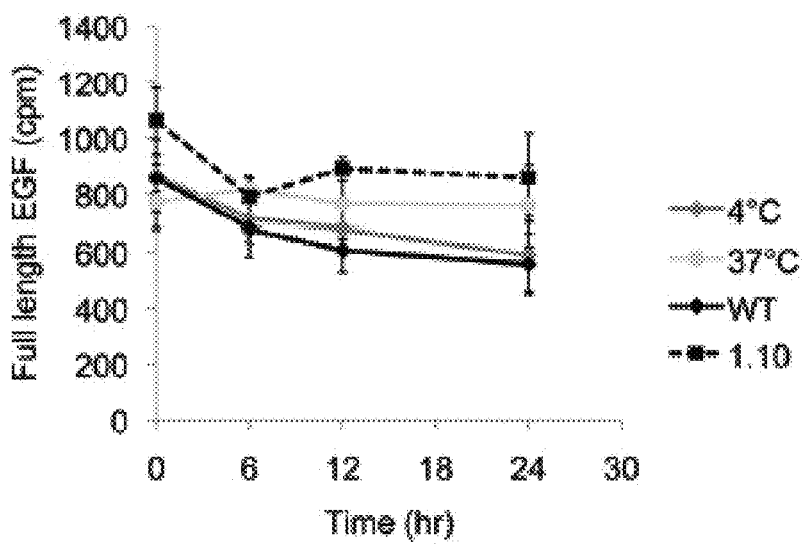

We found that wild-type EGF was dramatically depleted from the cell medium at the low starting concentration of 10 pM (FIG. 18A). Control samples of wild-type EGF incubated without cells at 37° C. or 4° C. remained near original levels. In contrast, mutant 1.10 was not depleted. Thus, at the concentrations where mutant 1.10 enhances cell proliferation compared to wild-type EGF, mutant 1.10 is able to sustain a higher ligand concentration in the medium. In combination with reduced EGFR depletion from the cell surface, this is a strong explanation for its enhanced biological activity compared to wild-type EGF. At the higher concentration of 100 pM, we found that neither wild-type EGF or mutant 1.10 undergoes significant depletion (FIG. 18B). This also agrees with their proliferation dose responses, as at 100 pM wild-type EGF and mutant 1.10 stimulate equivalent levels of cell proliferation.

EGF Mutants 1.10 and 1.78 Elicit Reduced Levels of EGFR Phosphorylation.

Figure 19:
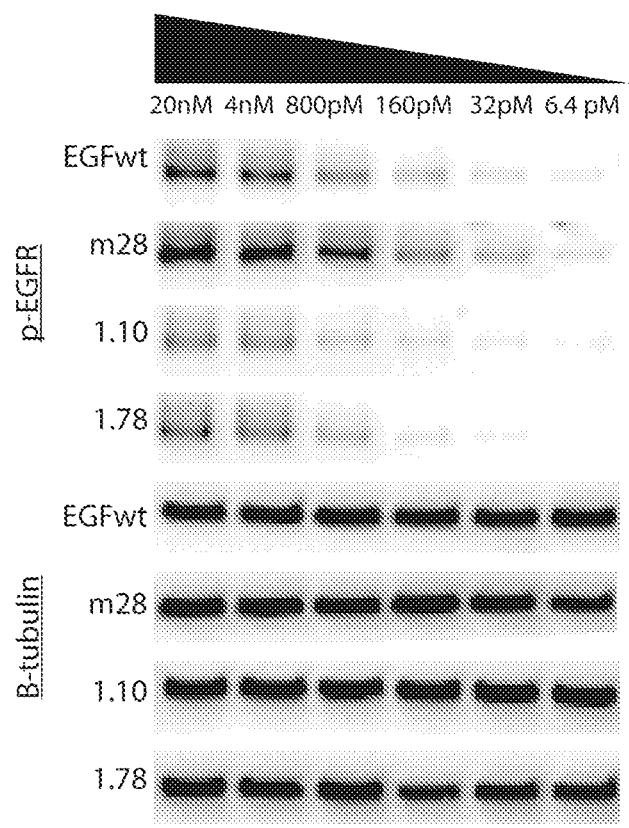
FIG. 19. EGFR Phosphorylation after treatment with mutants 1.10 and 1.78 is weaker compared to wild-type EGF Activation of EGFR in BJt5a cells after 3 minute stimulation with wild-type EGF, mutant 28, mutant 1.10, and mutant 1.78. Western blot analysis of phosphorylated EGFR (p-EGFR, top panel) and β-tubulin loading control (β-tubulin, lower panel).

We measured the ability of mutants 1.10 and 1.78 (expressed in *S. cerevisiae*) to stimulate EGFR phosphorylation (FIG. 19). The treatment of BJ5ta fibroblast cells for 3 minutes with EGF mutants 1.10 and 1.78 induced weaker levels of EGFR phosphorylation at all concentrations tested compared to wild-type EGF. EGF mutant m28 (see Example 3 below) is also included as a control for comparison, and induces greater levels of EGFR phosphorylation compared to wild-type EGF.

EGF Mutants 1.10 and 1.78 do not Enhance Chemotactic Cell Migration.

Figure 20:
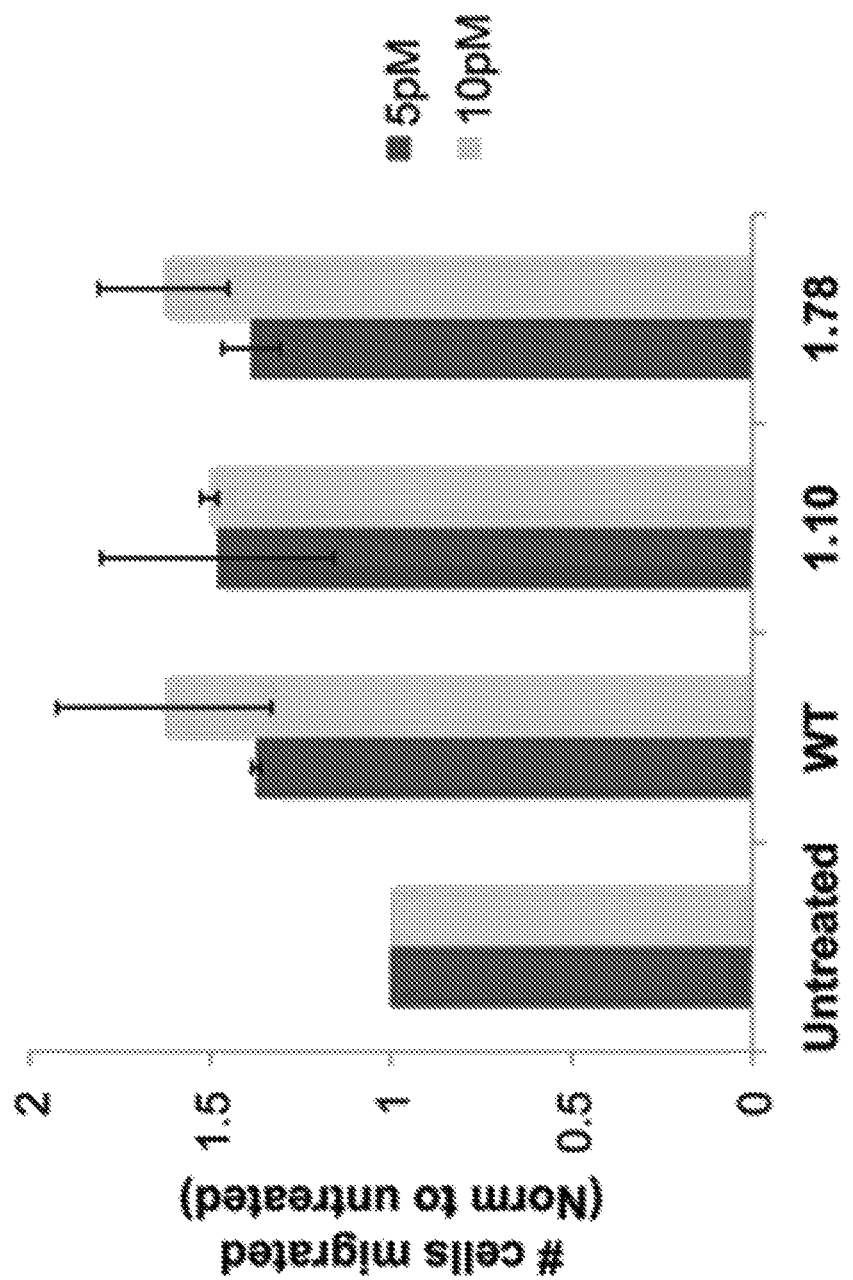
FIG. 20, Chemotactic cell migration after treatment with wild-type EGF and EGF mutants 1.10 and 1.78. BJ5ta cells were plated on one side of a porous membrane and allowed to migrate for 3 hours through the membrane towards 5 and 10 pM of wild-type EGF (WT) and mutants 1.10 and 1.78. Data was normalized to the number of cells which migrated towards media with no EGF. Averages and standard deviations of two independent experiments at each concentration are shown. Positive controls were included on each plate and were typically 3-fold over background.

In addition to cell proliferation, EGF is known to stimulate cell migration (Carpenter, G. and S. Cohen, Epidermal growth factor. J Biol Chem, 1990. 265(14): p. 7709-12; Tadaki. D. K. and S. K. Niyogi, Epidermal growth factor: Cellular and molecular function, in Growth Factors and Cytokines in Health and Disease, L. Derek and B. Carolyn, Editors. 1996, JAI, p. 85-121). Therefore, we assessed if mutants 1.10 and 1.78 improved cell migration compared to wildtype EGF. We used a chemotactic migration assay performed in modified Boyden chambers, which divide tissue culture wells into two regions by a porous membrane. BJ5ta cells were plated in one compartment in serum-free media and media with EGF was added to the other, Cells were allowed to migrate through the membrane for three hours, and the number of cells that migrated was quantified by digital photography and cell counting. From an initial characterization with wild-type EGF, we selected two treatment concentrations of 5 and 10 pM to compare wild-type EGF and mutants 1.10 and 1.78. At 5 and 10 pM, wild-type EGF stimulated more cell migration than untreated controls but was far from saturation. We found that mutants 1.10 and 1.78 did stimulate cell migration but only at levels equivalent to wild-type EGF (FIG. 20).

Characterization of Single and Double Point Mutations of Mutant 1.10

Figure 21:
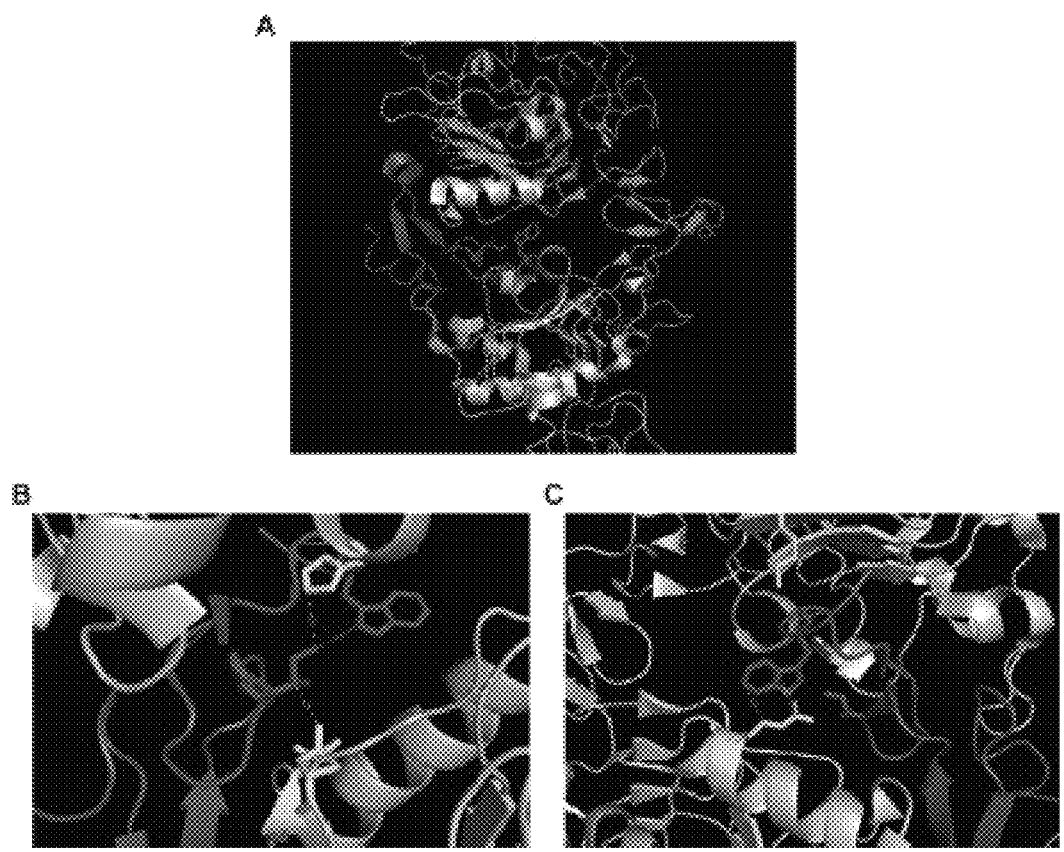
FIG. 21. Mutated residues in 1.10 mapped onto the crystal structure of EGF bound to EGFR. (A) Crystal structure of wild-type EGF bound to EGFR (PDB ID 1IVO [46]) with EGF in blue and EGFR in gray. Mutant 1.10 contains mutations D3G, I38A, and W49R. Side chains of residues I38 and W49 are highlighted in red. Residue D3 was not resolved in the crystal structure. The first N-terminal amino acid that was resolved (residue E5) is in red (no side chain showing). Closeups of (8) I38 and (C) W49 are shown, EGFR residues within 4 Å are highlighted in yellow. For I38, EGFR residues 12N and 17L are in the bottom of the picture and 409H is at the top. For W49, EGFR residue 29R is at the bottom and 465K is at the top.

To gain further insight into the mechanism of mutant 1.10's enhanced mitogenic activity, we examined its three point mutations (D3G, I38A, and W49R) using the crystal structure of EGF bound to EGFR (FIG. 21) (Ogiso, H., et al., Crystal structure of the complex of human epidermal growth factor and receptor extracellular domains, Cell, 2002, 110(6): p. 775-87). The N-terminus of EGF (including D3) does not interact directly with EGFR and the first four amino acids were not resolved in the crystal structure of EGF bound to EGFR. In contrast, EGF residues I38 and W49 are located in the interface between EGF and EGFR. However, only W49 has an obvious role in EGF-EGFR binding. The tryptophan ring is aligned with an arginine residue in EGFR, creating a cation-π interaction (Dougherty, D. A., Cation-pi interactions in chemistry and biology: a new view of benzene, Phe, Tyr, and Trp, Science, 1996. 271(5246): p. 163-8; Crowley, P. B. and A. Golovin, Cation-pi interactions in protein-protein interfaces. Proteins, 2005. 59(2): p. 231-9). Thus, of the three mutations, only W49R appeared to have an obvious effect on the binding of EGF to EGFR. But, all three mutations could influence mutant 1.10's biological activity through second sphere effects, as EGF is a very small protein. We cloned all six single and double point mutations into the CFPS plasmid pK7 and characterized their binding affinities, pH sensitivity, EGFR depletion, and mitogenic activity.

The Single W49R Mutation Weakens Binding Affinity but Both I38A and W49R Mutations are Required to Match Mutant 1.10.

Figure 22:
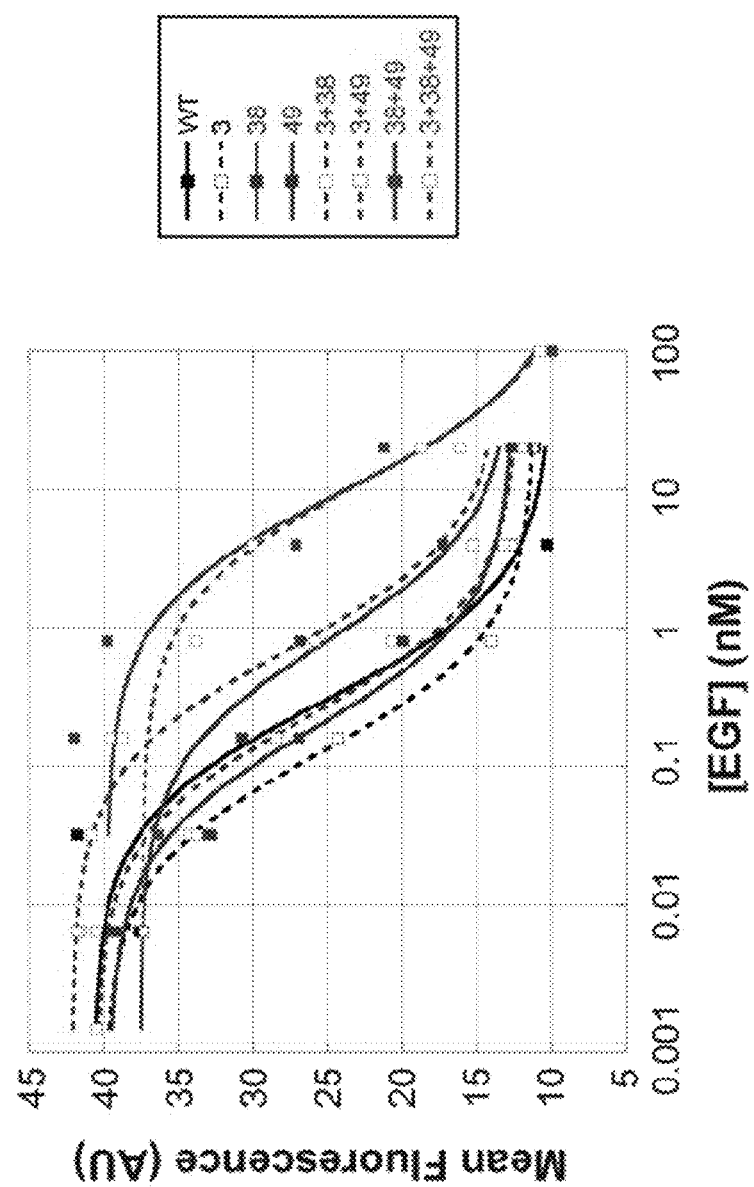
FIG. 22. Competition binding of wild-type EGF and 1.10 single and double point mutants. FLAG-tagged EGF (expressed and purified from *S. cerevisiae*) was competed off of BJ5ta cells by varying concentrations of wild-type EGF (WT) and single and double point mutations of D3G, I38A, and W49R, as indicated by the residue numbers in the legend (i.e. 3+38=D3G and I38A double mutant). Curves were fitted using KaleidaGraph software and are colored according to mutations: WT (black), I38A (green), W49R (blue) and I38A/W49R (red). Dashed and solid lines are with and without the D3G mutation, respectively. Three independent experiments were performed. Representative data are shown.

We performed competition binding experiments between the EGF mutants and YEGF on BJ15ta cells (FIG. 22 and Table 4). The effects of the single point mutations generally agreed with rough predictions from the crystal structure. W49R was the only one single mutation that weakened the binding affinity of EGF to EGFR, although the W49R mutant's binding affinity still remained stronger than mutant 1.10. The full reduction in binding affinity required the combination of I38A and W49R, despite the fact that I38A alone did not change the binding affinity of EGF to EGFR. Interestingly, the D3G mutation also had an inconsistent effect. Its introduction into wild-type EGF and the I38A/W49R double mutant slightly strengthened binding to EGFR but had no effect on the I38A and W49R single mutants.

TABLE 4

Competition binding of mutant 1.10 single and double point mutants. Competition binding experiments were performed on BJ5ta to compare the binding affinities of wild-type EGF (WT) and the mutant 1.10 single and double point mutants. Three independent experiments were performed with three different batches of protein. Curves were fit using kaleidaGraph software and the average and standard deviations of the half-maximal inhibitory concentrations (IC50 values) are given.

|  | Mutated residues | IC50 on BJ5ta cells (nM) |
|---|---|---|
| WT | — | 0.4 ± 0.1 |
| Single | 3 | 0.15 ± 0.03 |
| mutants | 38 | 0.4 ± 0.1 |
|  | 49 | 0.7 ± 0.2 |
| Double | 3 + 38 | 0.3 ± 0.1 |
| mutants | 3 + 49 | 0.7 ± 0.2 |
|  | 38 + 49 | 12 ± 2 |
| 1.10 | 3 + 38 + 49 | 7 ± 2 |

Both I38A and W49R Mutations are Required for Significant pH Sensitivity.

Figure 23:
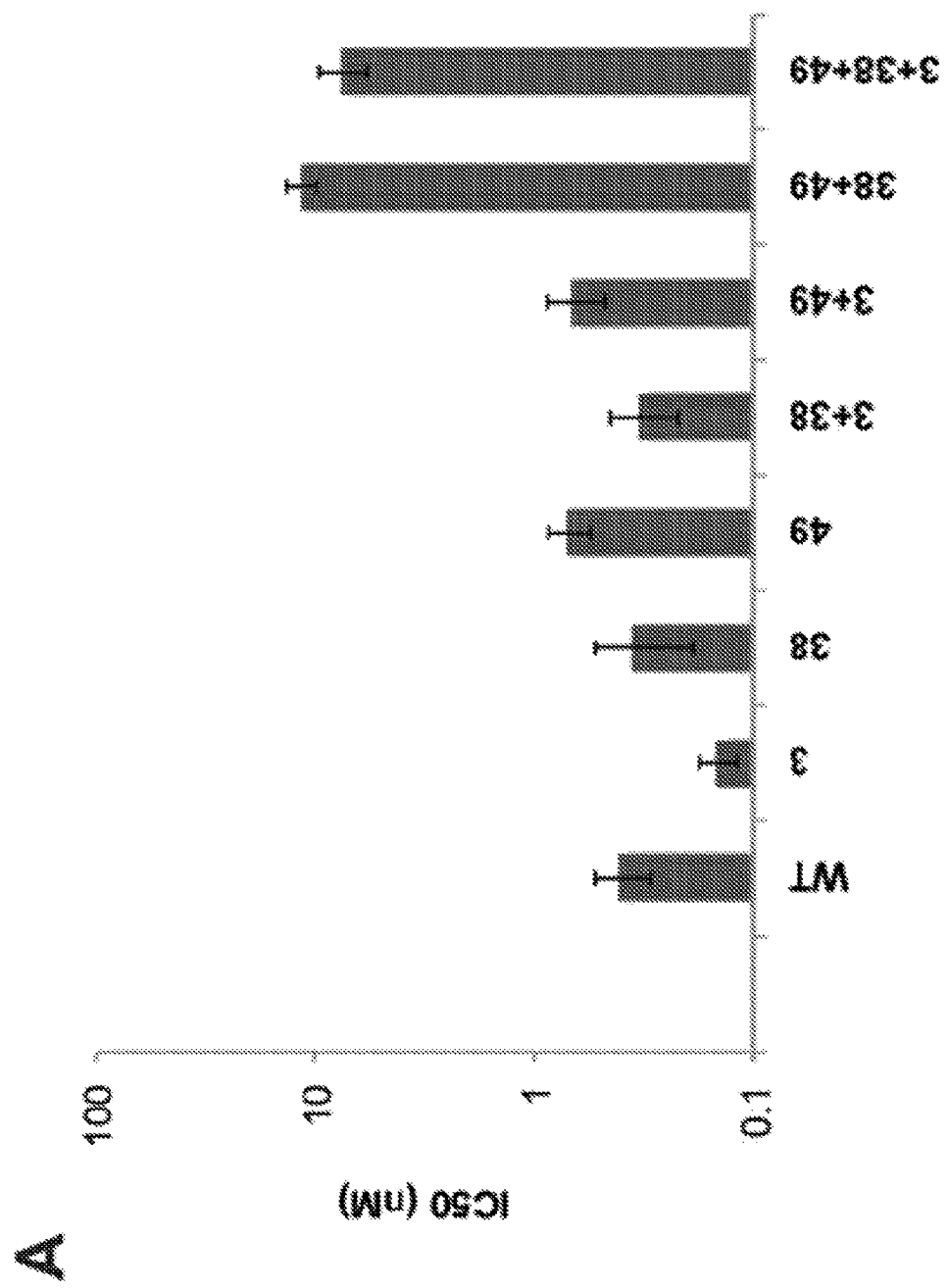
FIG. 23. pH sensitivity and stimulation of EGFR depletion of wild-type EGF and mutant 1.10 single and double point mutants. Characterization of wild-type EGF (WT) and single and double point mutations of D3G, I38A, and W49R, as indicated by the residue numbers in the legend (i.e. 3+38=D3G and I38A double mutant). (A) IC50s from competition binding with FLAG-tagged EGF on BJ5ta cells. Curves fitted using KaleidaGraph software. (B) The fraction of EGF that dissociated after a 5 min wash at pH 6.5. (C) EGFR depletion after 4 hour treatment with 100 pM of EGF (P<0.0001 for I38A compared to WT: **P<0.001 for W49R compared to WT; *P<0.05 for I38A and W49R compared to mutant 1.10). In A and B, columns represent average and standard deviation of three independent experiments. In C, columns represent average and standard error of three independent experiments.
Figure 23:
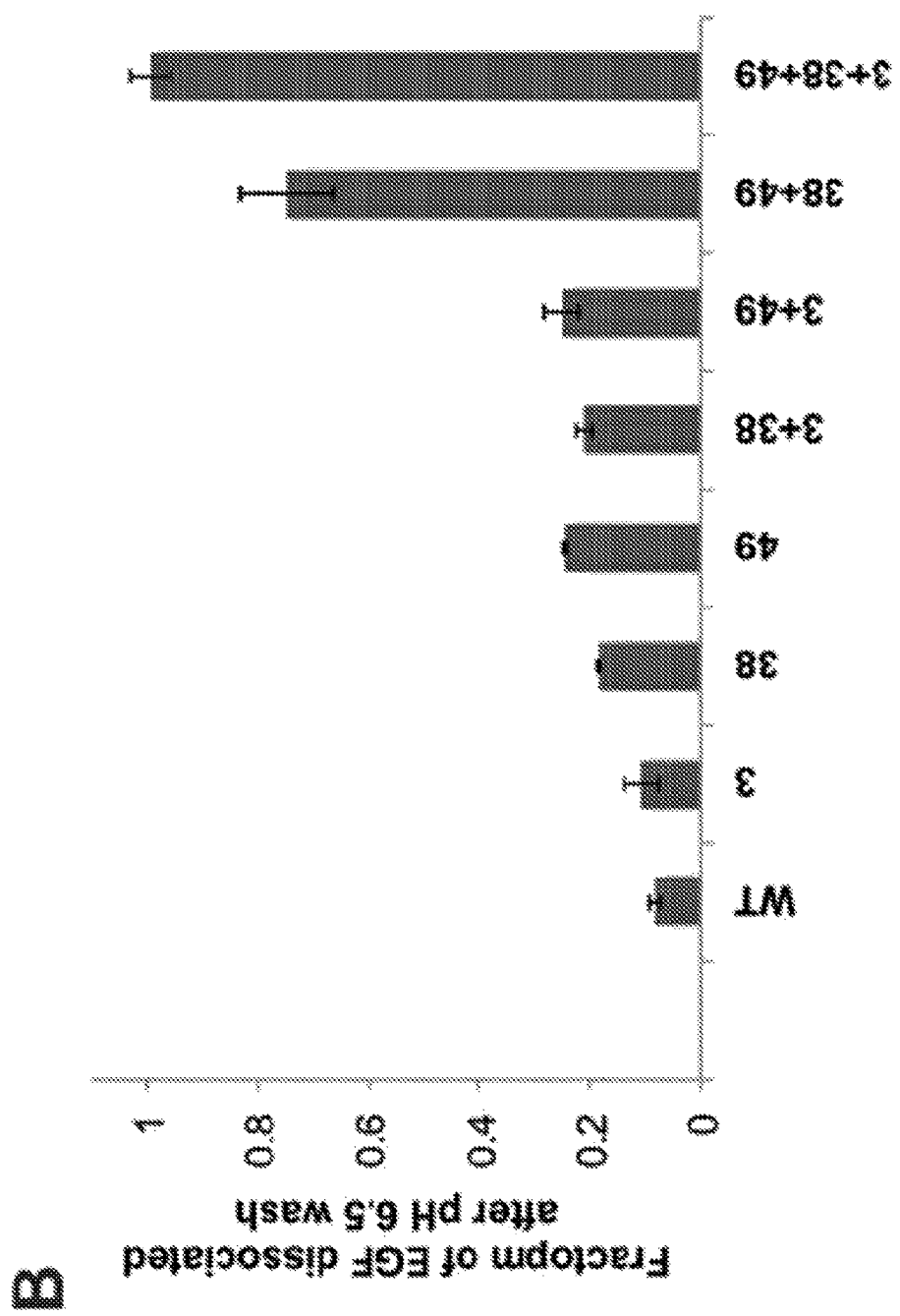
Figure 23:
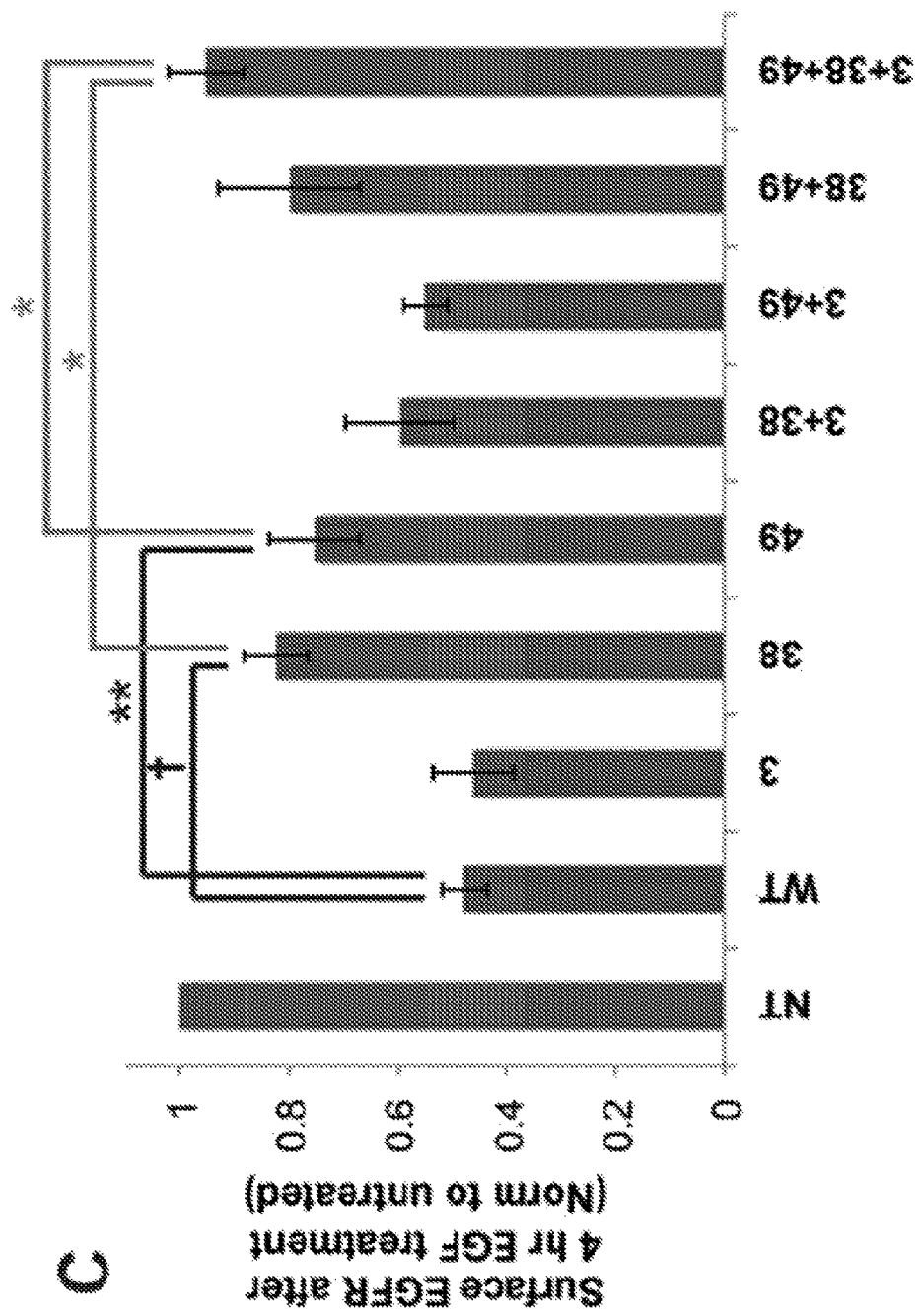

We next compared the pH sensitivities of the mutant 1.10 single and double point mutants by measuring the fraction of EGF which dissociated from EGFR after a five minute incubation at pH 6.5 (FIG. 23B). As we saw in our initial characterization, a significant amount of mutant 1.10 dissociated at pH 6.5. The single I38A and W49R mutations increased the level of EGF dissociation over wild-type EGF by approximately two- to three-fold. The effect of the I38A mutation was notable as it did not alter EGF's binding affinity at physiological pH (pH 7.4). The D3G mutation had negligible effect on its own or when combined with I38A or W49R. Agreeing with the competition binding results, the combination of I38A and W49R was required for any substantial increase in EGF pH sensitivity Nevertheless, that double mutant still was not as sensitive to lower pH as the triple mutant 1.10.

Single I38A and W49R Mutations Reduce EGFR Depletion.

Figure 24:
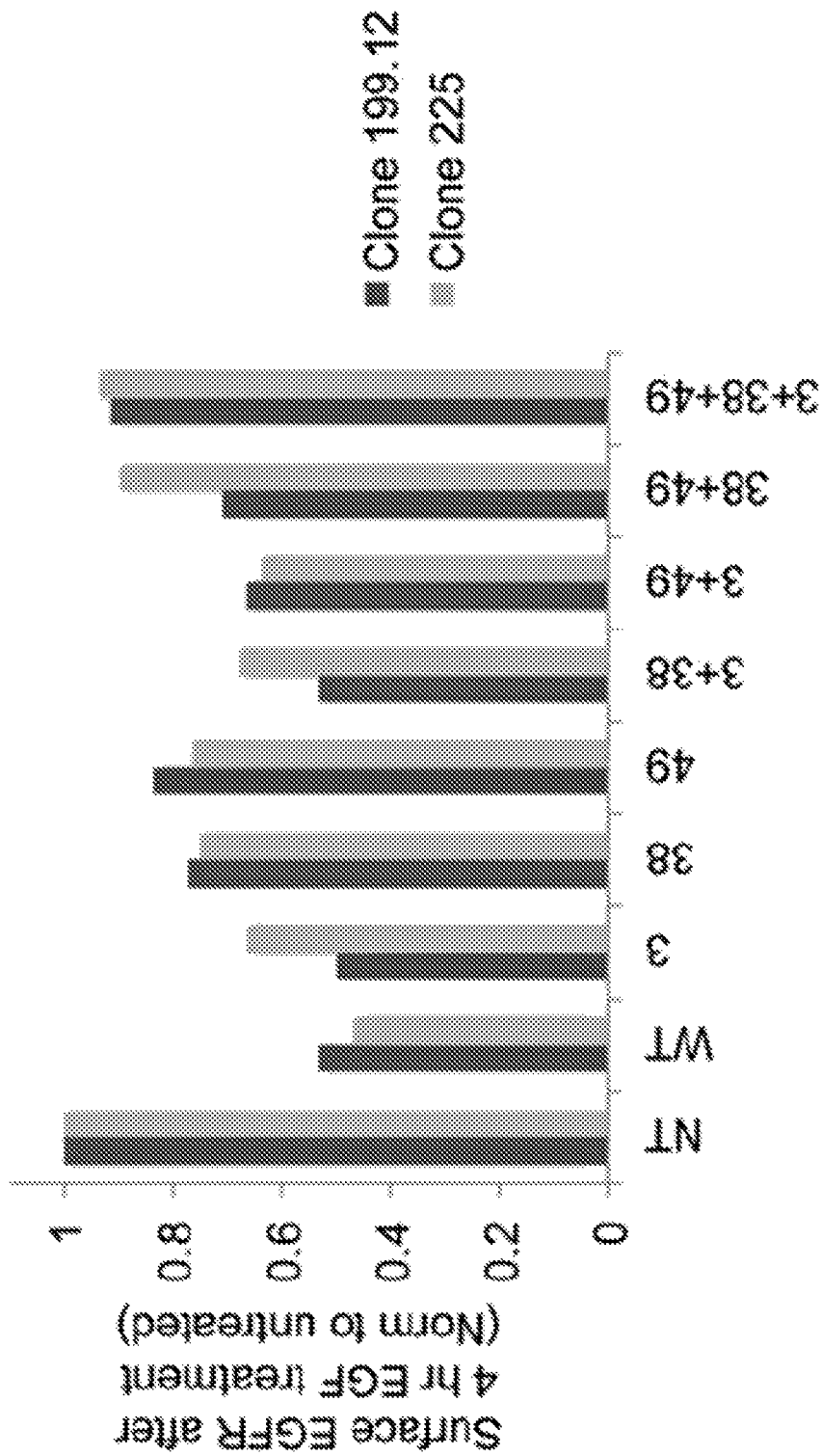
FIG. 24. Comparison of EGFR depletion after treatment with mutant 1.10 single and double point mutants using two EGFR antibodies. The EGFR depletion results for the mutant 1.10 single and double point mutants using EGFR antibody clone 199.12 were confirmed by comparison with a second competitive EGFR antibody (clone 225). Surface EGFR levels measured by the two antibodies were within experimental error.

Characterization of the single and double point mutants suggested that both I38A and W49R were necessary to recapitulate the binding properties of mutant 1.10. We investigated to see if this trend continued for depletion of cell surface EGFR. We measured the levels of surface EGFR after 4 hour treatments with 100 pM of the single and double mutants following the same procedure described above (FIG. 23C). Surprisingly, in contrast to their relatively minor effects on equilibrium binding and pH sensitivity, we found that treatment with the single I38A and W49R mutations induced significantly less EGFR depletion (surface EGFR levels of 82% and 75% of untreated controls, respectively) compared to wild-type EGF (48% of untreated) ($P<0.0001$ for I38A and $P<0.001$ for W49R, both compared to wild-type EGF). However, the single mutations still induced more EGFR depletion than mutant 1.10 (95% of untreated) ($P<0.05$ for I38A and W49R, both compared to mutant 1.10). As before, the D3G mutation had conflicting effects, Alone, it stimulated EGFR depletion equivalent to wild-type EGF. Introduction of D3G into I38A or W49R eliminated any reduction in EGFR depletion, lowering surface EGFR levels back down to 60% and 55%, respectively. As before, results were confirmed using a second primary antibody to EGFR (FIG. 24).

Figure 25:
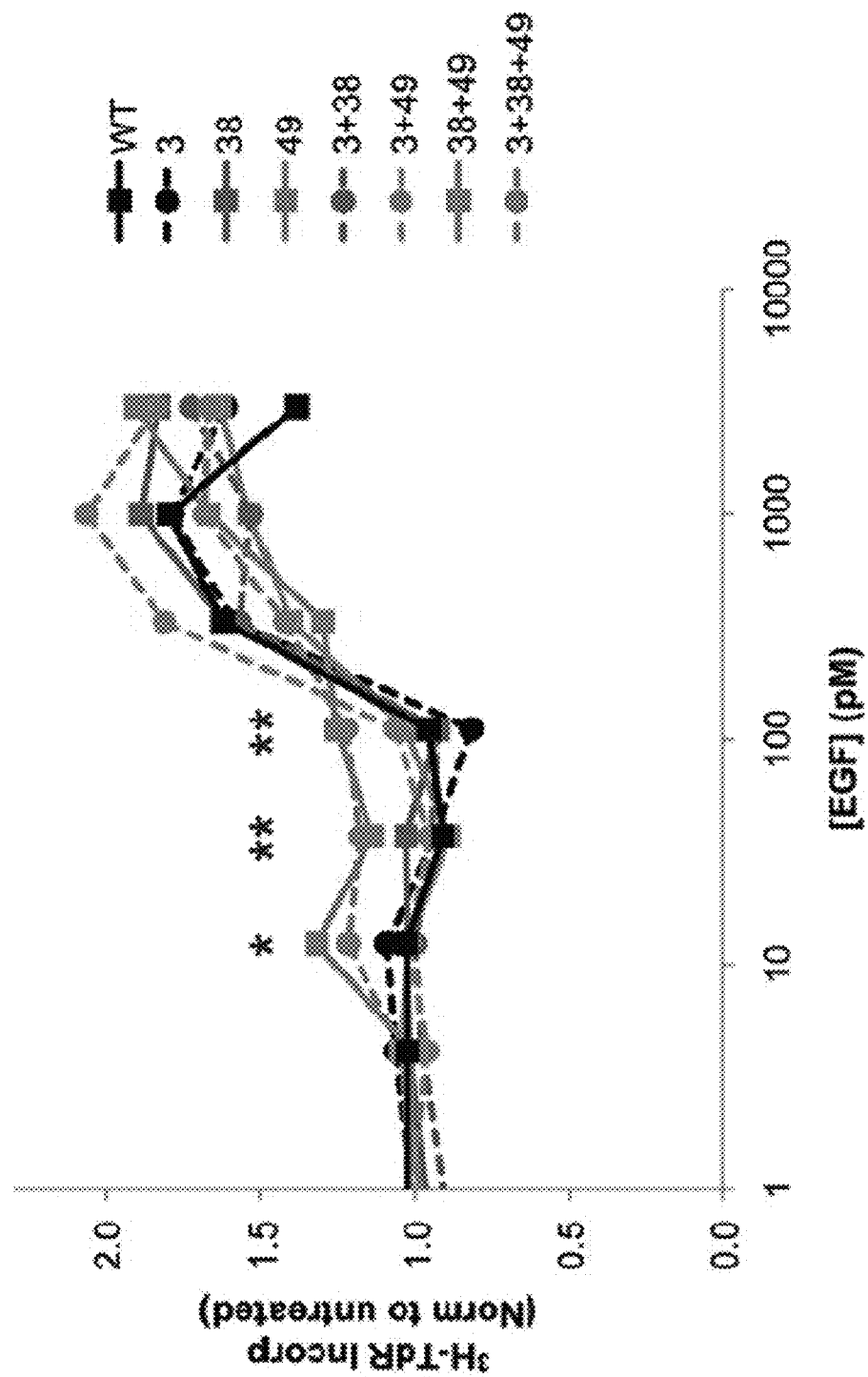
FIG. 25. Cell proliferation of wild-type EGF and mutant 1.10 single and double point mutants, Cell proliferation dose responses of wild-type EGF (WT) and single and double point mutations of D3G, I38A, and W49R, as indicated by the residue numbers in the legend (i.e. 3+38=D3G and I38A double mutant), measured by 3H-thymidine (3H-TdR) incorporation. Data are colored according to mutations; WT (black), I38A (green), W49R (blue) and I38A/W49R (red). Dashed and solid lines are with and without the D3G mutation, respectively. Data from three independent experiments was normalized and averaged. Error bars are not shown for clarity. For [EGF] below 300 pM, normalized standard deviations for all data points except one were less than 15%. (*$P=0.02$ for 38+49 and $P=0.05$ for 3+38+49 compared to WT; **$P \leq 0.02$ for 38+49 and 3+38+49 compared to WT).

Both I38A and W49R mutations are required for enhancement of cell proliferation. Finally, we assessed contribution of each point mutation to mitogenic activity. We measured cell proliferation dose response curves for the single and double point mutants with BJ5ta cells (FIG. 25). Despite the variations in their behavior seen in the EGFR depletion experiments, all of the single point mutants stimulated cell proliferation equivalent to wild type EGF. Only the double I38A and W49R mutant significantly enhanced stimulation of cell proliferation at lower concentrations and was indistinguishable from mutant 1.10.

Example 3

Receptor tyrosine kinases (RTKs) regulate critical coli signaling pathways, yet the properties of their cognate ligands that influence receptor activation are not fully understood. There is great interest in parsing these complex ligand-receptor relationships using engineered proteins with altered binding properties. Here we focus on the interaction between two engineered epidermal growth factor (EGF) mutants and the EGF receptor (EGFR), a model member of the RTK superfamily. We found that EGF mutants with faster kinetic on-rates stimulate increased EGFR activation compared to wild-type EGF.

Materials and Methods

Materials and Reagents.

PBSA was composed of phosphate buffered saline (PBS pH 7.4 supplemented with 1 mg/mL bovine serum albumin (BSA). Cell Lysis Buffer was composed of 20 mM Tris-HCl, 150 mM NaCl, and 1% triton X-100 at pH 7.5. SPR kinetic and control experiments were performed in degassed Running Buffer (PBS pH 7.4 containing 0.1 mg/mL BSA and 0.005% Surfactant P20). SPR pH binding experiments were performed in degassed pH Buffers created using the Na2HPO4-citric acid buffering system at various pHs ranging from 5.0 to 8.5 supplemented with 50 mM NaCl, 0.1 mg/mL BSA, and 0.005% Surfactant P20. For immunoblotting, anti-EGFR(SC-03), anti-phosphorylated EGFR (Tyr 1173, SC-12351), and anti-actin (SC-1616) primary antibodies and horseradish peroxidase-conjugated secondary antibody (SC-2004) were purchased from Santa Cruz Biotechnology. Western blots were developed by enhanced chemiluminescence with an ECL Plus western blot kit (GE Healthcare). Protease inhibitor cocktails were composed of: 1 µg/mL leupeptin, 1 µg/mL pepstatin A, 1 µg/mL chymostatin, and 1× Complete Mini-EDTA-free Protease Inhibitor Tablet (Roche). For EGFR downregulation assays, anti-EGFR primary antibody (clone 199.12) was purchased from Lab Vision. For flow cytometry analysis, fluorescein-conjugated anti-FLAG antibody (F4049) and R-phycoerythrin-conjugated goat anti-mouse antibody (P9670) were purchased from Sigma-Aldrich.

Soluble Protein Production.

EGF wild-type and mutant DNA was subcloned into a yeast secretion vector containing N-terminal FLAG and C-terminal hexahistidine epitope tags and was transformed into the *Saccharomyces cerevisiae* strain YVH10 for soluble production as described previously. EGF proteins were purified from yeast supernatants by nickel affinity chromatography using HISSelect resin (Sigma-Aldrich) followed by gel filtration FPLC with a Superdex 75 10/300 GL column (Amersham Biosciences) on a Varian Prostar chromatography system. Protein purity was verified by SOS-PAGE using 4-12% Bis-Tris gels (Invitrogen).

Monoclonal antibody 225 (mAb 225), an antibody with conformational specificity to the extracellular domain of EGFR, was expressed in HB-8505 mouse hybridoma cells (ATCC). Antibody was purified from the cell culture supernatant by immunoaffinity chromatography using a Protein G sepharose column (Invitrogen) and was covalently crosslinked to CNBr-activated sepharose beads (GE Healthcare). The extracellular domain (residues 1-621) of human EGFR was subcloned into the pMIB secretion plasmid (Invitrogen) and expressed in Hi Five insect cells as described previously. Insect cell culture supernatant was concentrated and buffer exchanged into PBS, pH 7.4 using a tangential flow system with 10 kDa molecular weight cutoff Centramate☐ cassettes (Pall). Properly folded hEGFR was then purified by immunoaffinity chromatography using the prepared mAb 225 sepharose column. Protein purity was verified by SOS-PAGE with 4-12% Bis-Tris gels (Invitrogen). The amino acid sequences of the mutants studied are shown in Table 5, below.

TABLE 5

Amino acid sequences of wild-type EGF (SE0 ID NO: 1), mutant 28 ("m28", SEQ ID NO: 16), and mutant 123 ("m123", SEQ ID NO: 17). Mutations are underlined in bold type.

| Clone | Sequence |
| --- | --- |
| EGFwt | NSDSECPLSHDGYCLHDGVCMYIEALDKYACNCVVGYIGERCQYRDLKWWELR |
| m28 | NSDSECPLSHDGYCLHGGVCMYIKAVDRYACNCVVGYIGERCQYRDLTWWGPR |
| m123 | NSYSECPPSYDGYCLHDGVCRYIEALDSYACNCVVGYAGERCQYRDLRWWGR**R |

Cell Growth and Maintenance.

NR6WT murine fibroblast cells were grown in alpha MEM (Gibco) supplemented with 1% penicillin/streptomycin, 1% sodium pyruvate, 1% L-glutamine, 7 ☐g/mL Geneticin, and 10% fetal bovine serum (FBS). For all experiments, FBS was removed and cells were incubated for 24 h in the presence of 1% dialyzed FBS unless otherwise noted. BJ-5ta human fibroblast cells (ATCC) were grown in DMEM (Invitrogen) supplemented with 20% Medium 199, 1% penicillin/streptomycin, 1% sodium pyruvate, 1% L-glutamine, and 10% FBS. All experiments with BJ-5ta cells were performed in the absence of serum following 48 h of serum starvation unless otherwise noted.

CHO Cell Growth and Transfection.

Chinese hamster ovary (CHO) cells (ATCC) were grown in F12 media (Gibco) supplemented with 1% penicillin/streptomycin, 1% sodium pyruvate, 1% L-glutamine, and 10% FBS. Cells were transfected with pcDNA3.0, GFP, ErbB1, ErbB2, or ErbB4 [1] using the Amaxa electroporation method according to the manufacturer's protocol. One day after transfection, 1.0 mg/mL Geneticin (Invitrogen) was added to the media, and the cells were grown until confluent. Stably transfected cells were isolated by fluorescence-activated cell sorting for positive expression of the desired receptor.

Cell Binding Assays.

Equilibrium receptor binding affinities were measured on NR6WT and BJ-5ta fibroblast cells after incubation with EGF (three-fold dilutions from 200 nM to 10 pM) for 6 hrs at 4° C. Cells were labeled with a FITC-conjugated antibody directed against an N-terminal FLAG epitope tag on EGF and analyzed using a FACSCalibur flow cytometer (BD Biosciences). Receptor binding off-rates were measured using NR6WT cells pretreated for 20 min with 100 µM phenylarsine oxide to inhibit EGFR internalization. Cells were incubated with 25 nM EGF for 10 min at 37° C., washed, and incubated in serum-free medium at 37° C. for times ranging from 30 min to 7 h. The level of EGF persisting on the cell surface was measured by flow cytometry as above.

EGF Ligand Specificity.

The binding specificities of wild-type and mutant EGF were determined by flow cytometry using CHO cells transfected with EGFR or other ErbB receptor family members. CHO cells were incubated with 25 nM soluble wild-type EGF, m28, or m123 for 10 min at room temperature. Cells were labeled with a FITC-conjugated antibody directed against the N-terminal FLAG epitope tag on EGF and analyzed by flow cytometry.

Surface Plasmon Resonance Assays.

EGF binding interactions with immobilized human (hEGFR) and murine EGFR (mEGFR) were analyzed by surface plasmon resonance (SPR) using a Biacore 3000 instrument (Biacore Life Sciences). Kinetic experiments were performed at 25° C. in degassed running buffer. EGF at various concentrations (two-fold dilutions from 400 nM to 780 pM) were flowed over EGFR-immobilized surfaces at 30 µL/min for 2 min. Final sensorgrams were analyzed with BIAevaluation software (Biacore Life Sciences) and simultaneously fit for affinity and kinetic parameters using a 1:1 Langmuir binding model.

Recombinant human EGFR extracellular domain (hEGFR) and chimeric murine EGFRFc (mEGFR, R & D Systems) were immobilized on separate Biacore CM5 sensor chips by amine coupling using degassed HBS-EP (0.01 M HEPES buffer pH 7.4, 0.15 M NaCl, with 0.005% Surfactant P20) at 25° C. according to the following protocol. The CM5 dextran matrix was activated using a 1:1 solution of 0.4 M 1-ethyl-3-(3-dimethylaminopropyl)-carbodiimide and 0.1 M N-hydroxysuccinimide in water, Next, hEGFR (200 µg/mL in 10 mM sodium acetate pH 4.5) or mEGFR (10 µg/mL in 10 mM sodium acetate pH 4.5) was flowed over the activated surfaces of flow cells two and four at 5 µL/min until the target immobilization levels (3000 response unit [RU] for hEGFR or 4500 RU for mEGFR) were reached. Uncoupled receptor was removed, and unreacted moieties on the chip matrix were blocked with 1 M ethanolamine-HCl pH 8.5. In both of the sensor chips, flow cells one and three were activated and blocked without exposure to EGFR to serve as background control surfaces.

All control experiments were performed for each growth factor-receptor pair at 25° C. in degassed running buffer. Linked reaction control experiments were performed at a ligand concentration of 400 nM and flow rate of 20 µL/min with association phases of 1, 3, and 9 min. Linked reaction control experiments showed that ligand dissociation rates were independent of incubation time at steady-state, indicating a lack of kinetic heterogeneity. Mass transfer control experiments were performed at a ligand concentration of 50 nM with flow rates of 5, 15, and 75 L/min and association phases of 2 min. Mass transfer control experiments showed no significant differences in ligand binding with changes in flow rate, confirming the absence of mass transport limitations. Surfaces of the hEGFR sensor chip were regenerated by washing with running buffer at 30 µL/min for 5 min. Surfaces of the mEGFR sensor chip were regenerated by washing in running buffer at 30 µL/min for 8 min followed by a 15 sec pulse of 10 mM sodium acetate pH 4.5 at 50 µL/min and equilibration with running buffer at 30 µL/min for 2 min.

pH titration binding experiments were performed at 25° C. in degassed buffer at various pHs ranging from 5.0 to 8.5. Wild-type and mutant EGF were diluted to 200 nM in pH buffer and flowed over the surface of the hEGFR sensorchip at a flow rate of 20 µL/min for 2 min. The hEGFR and mEGFR surfaces were regenerated as noted above. pH titration binding experiments were performed in triplicate at each pH over flow cells one and two for bath the hEGFR and mEGFR surfaces. The steady-state binding response was measured for each growth factor at the association phase plateau of the sensorgram. To confirm that the decreased binding response of the growth factor to the receptor was not caused by denaturation of the receptor, we repeated the binding experiment using buffer at pH 7.5 after performing the binding experiment at all pH values and compared the binding response generated from the first and second experiments.

EGFR Activation and Immunoblotting.

BJ-5ta fibroblasts were pretreated with $Na_3VO_4$ phosphatase inhibitor and incubated with EGF (five-fold dilutions from 20 nM to 6.4 pM) for 15 min at 37° C. Cells were lysed with 100 µL lysis buffer supplemented with 1 mM $Na_3VO_4$ and protease inhibitors. Cell lysates were resolved by SDS-PAGE under reducing conditions and analyzed by western blot with primary antibodies directed against actin or phosphorylated or total EGFR and a horseradish peroxidase-conjugated secondary antibody. Western blots were developed using chemiluminescence and imaged using a Chemidoc System (BioRad).

EGFR Downregulation Assays.

BJ-5ta fibroblasts were treated with 0.1 nM EGF for times ranging from 15 min to 6 h. Post-stimulation, cells were fixed with 1.5% paraformaldehyde, and cell-surface EGFR was analyzed by flow cytometry using a primary antibody directed against EGFR and a secondary R-phycoerythrin-conjugated antibody.

Cell Proliferation Assay.

BJ-5ta cells were plated in 96-well plates at a density of 5,000 cells/well and 2,500 cells/well, respectively, in 100 µl of medium. After 24 h, cells were serum-starved for 24 h (NR6WT) or 48 h (BJ-5ta) The medium was then replaced with 100 µl of serum-free medium containing serial dilutions of growth factors. After an additional 24 h for NR6WT and 48 h for BJ-5ta, 1 µCi of 3H-TdR (GE Healthcare. Waukesha. Wis.) was added to each well in 50 µl of serum-free medium. 3H-TdR incorporation was measured 24 h later by harvesting the cells onto glass fiber filtermats (Perkin Elmer, Waltham, Mass.) using a Mach IIIM harvester (Tomtec, Hamden, Conn.) and performing scintillation counting with a Wallac MicroBeta (Perkin Elmer, Waltham, Mass.).

Chemotactic Cell Migration Assay.

Costar transwells (8.0 µm pores, 6.5 mm diameter) were coated on both sides with bovine fibronectin (10 µg/ml) overnight at 4° C. washed 3 times with PBS, and then blocked with 1% bovine serum albumin (BSA) in PBS at 37° C. for 1 h prior to usage. 2.5×105 cells in 200 µl of serum-free medium with 1% BSA were placed into the upper chamber of coated transwells and allowed to migrate toward media containing 0.3 nM wild-type EGF, m28, or m123 in the lower chamber for 3 h under tissue culture conditions. Non-migrated cells were removed by wiping the upper side of the membrane with a cotton swab. The transwells were washed three times with PBS, fixed with methanol, and stained with modified Giemsa. Pictures were taken of the migrated-stained cells in nine random high powered fields (20×) using light microscopy, and the number of migrated cells were counted. Data is represented as the percent change in number of cells migrating toward mutant EGF from number of cells migrating toward wild-type EGF.

Results

EGF Mutants Bind Specifically to EGFR and not to Other ErbB Receptors.

Figure 29:
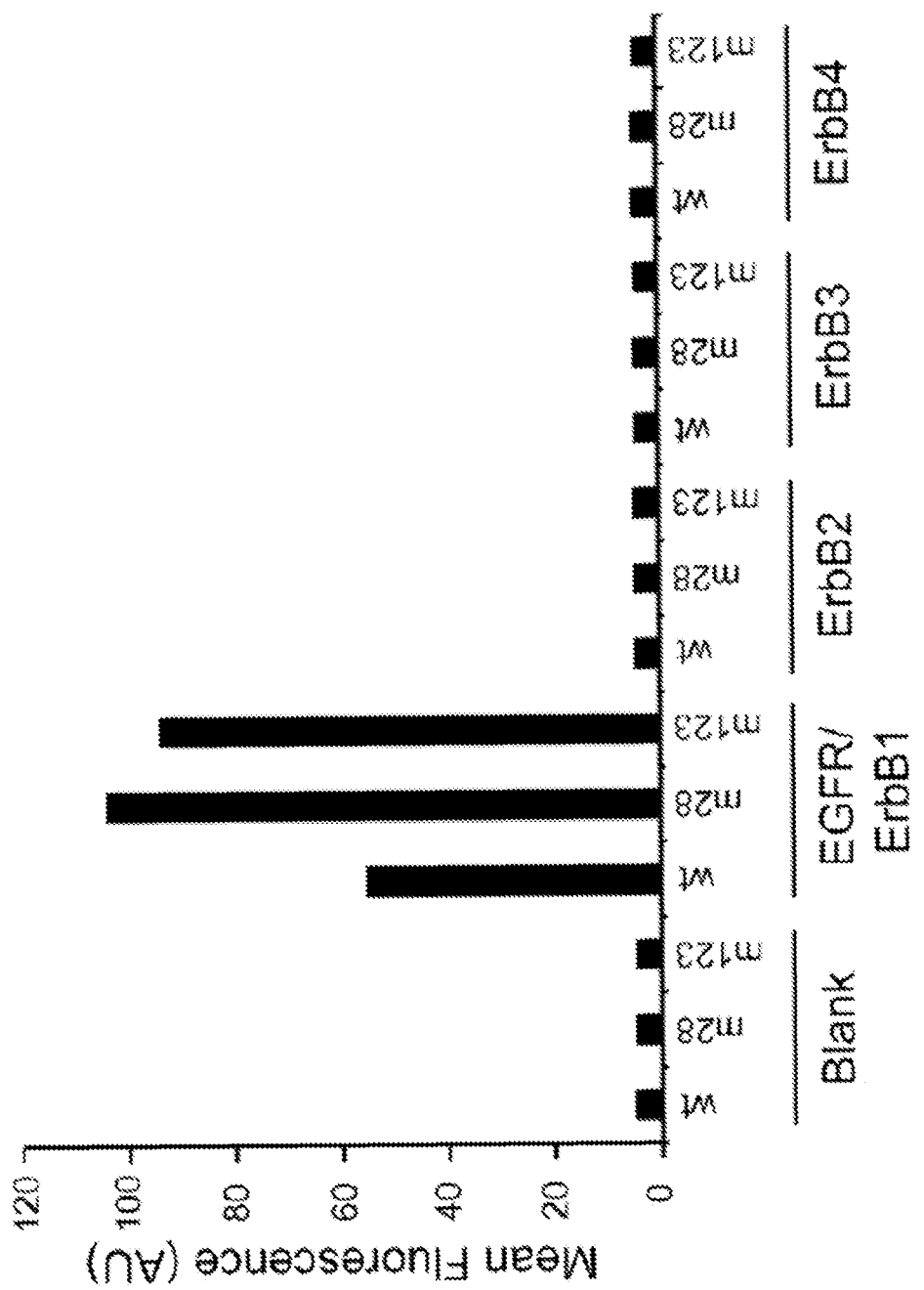
FIG. 29. Binding specificity of wild-type EGF, mutant 28, and mutant 123 for ErbB receptors expressed on the surface of CHO cells. EGFwt and mutants retain binding specificity for EGFR compared to other ErbB receptor family members. A representative dataset from triplicate experiments is shown.

EGFR is one of four receptors in the ErbB family, which also includes ErbB2, ErbB3, and ErbB4. We measured the ErbB binding specificity of m28 and m123 compared to wad-type EGF (EGFwt), using stably-transfected CHO cells individually expressing each of the four ErbB receptors. We found that EGFwt and the engineered mutants bound specifically to EGFR but not to other ErbB receptor family members (FIG. 29) demonstrating that the amino acid mutations conferring high-affinity binding to EGFR do not alter binding specificity.

EGF Mutants Bind Cell Surface EGFR with Higher Affinity than Wild-Type EGF.

Figure 26:
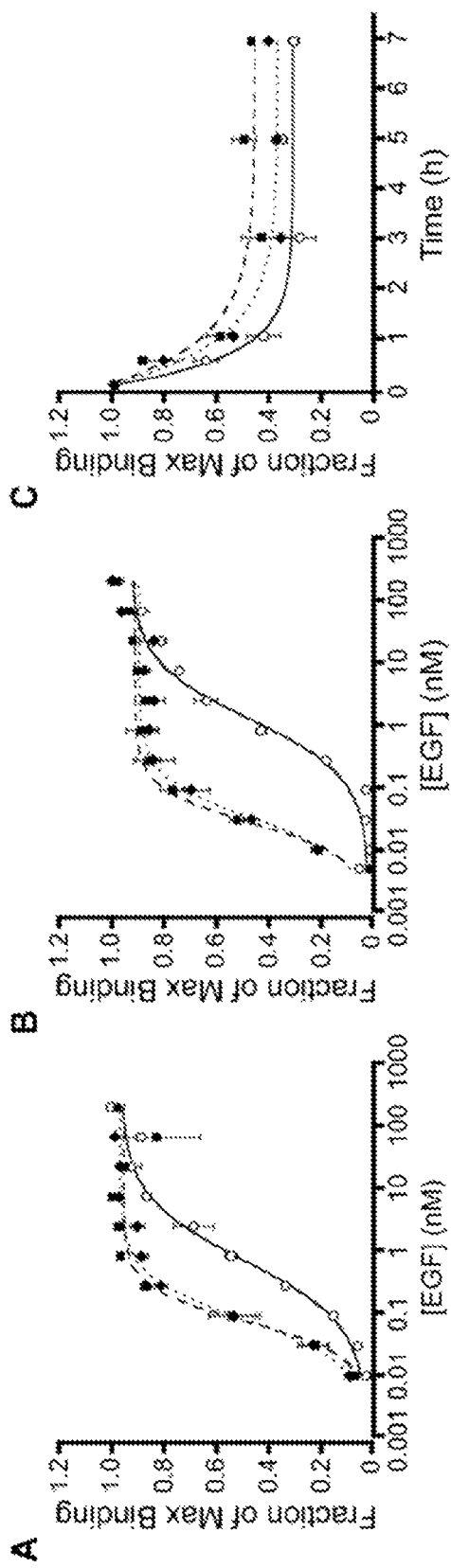
FIG. 26. Binding of wild-type EGF, mutant 28, and mutant 123 to EGFR expressed on the cell surface. Binding titrations of EGF to EGFR on (A) NR6WT and (B) BJ-5ta cells. (C) Off-rates of EGF binding to EGFR ort NR6WT cells. EGFwt (open circles, solid line), m28 (black squares, dashed line), and m123 (black diamonds, dotted line). Binding experiments were performed in triplicate and error bars denote standard error of the mean.

We next determined equilibrium binding affinities ($K_D$) of EGFwt, m28, and m123 to EGFR expressed on fibroblasts and confirmed that the mutants bound with stronger affinity (FIGS. 26A and B, and Table 2). Compared to EGFwt, m28 and m123 bound eight-fold more tightly to EGFR on NR6WT cells. On BJ-5ta cells, m28 and m123 bound 37- and 33-fold more tightly, respectively, than EGFwt. We also found that the kinetic off-rates ($k_{off}$) of binding of EGFwt and mutants to NR6WT cells was comparable (FIG. 26C and Table 6). Based on the empirically observed $K_D$ and $k_{off}$ values, expected on-rates ($k_{on}$) of receptor binding were determined ($K_D=k_{off}/k_{on}$) to be approximately four- and six-fold faster for m28 and m123, respectively, compared to EGFwt.

TABLE 6

Equilibrium binding affinities and kinetic rates of wild-type EGF, mutant 28, and mutant 123 binding to cell-surface EGFR. Numbers in parenthesis denote fold-change over EGFwt.

|  | EGFwt | m28 | m123 |
| --- | --- | --- | --- |
| NR6WT Cells |  |  |  |
| $K_D$ (pM) | 600 ± 200 (—) | 80* ± 20 (8) | 80* ± 50 (8) |
| $k_{off}$ ($s^{-1}$) × $10^{-4}$ | 4.3 ± 0.8 (—) | 2.60 ± 0.08 (1.7) | 2.8 ± 0.4 (1.5) |
| $k_{on}$ ($M^{-1}s^{-1}$) × $10^5$ | 7 (—) | 30 (4) | 40 (6) |
| BJ-5ta Cells |  |  |  |
| $K_D$ (pM) | 1100 ± 200 (—) | 30* ± 6 (37) | 34* ± 7 (33) |

*Statistical significance (p < 0.05) compared to EGFwt.

EGF Mutants Bind EGFR Extracellular Domain with Faster Kinetic on-Rates than Wild-Type EGF.

Figure 27:
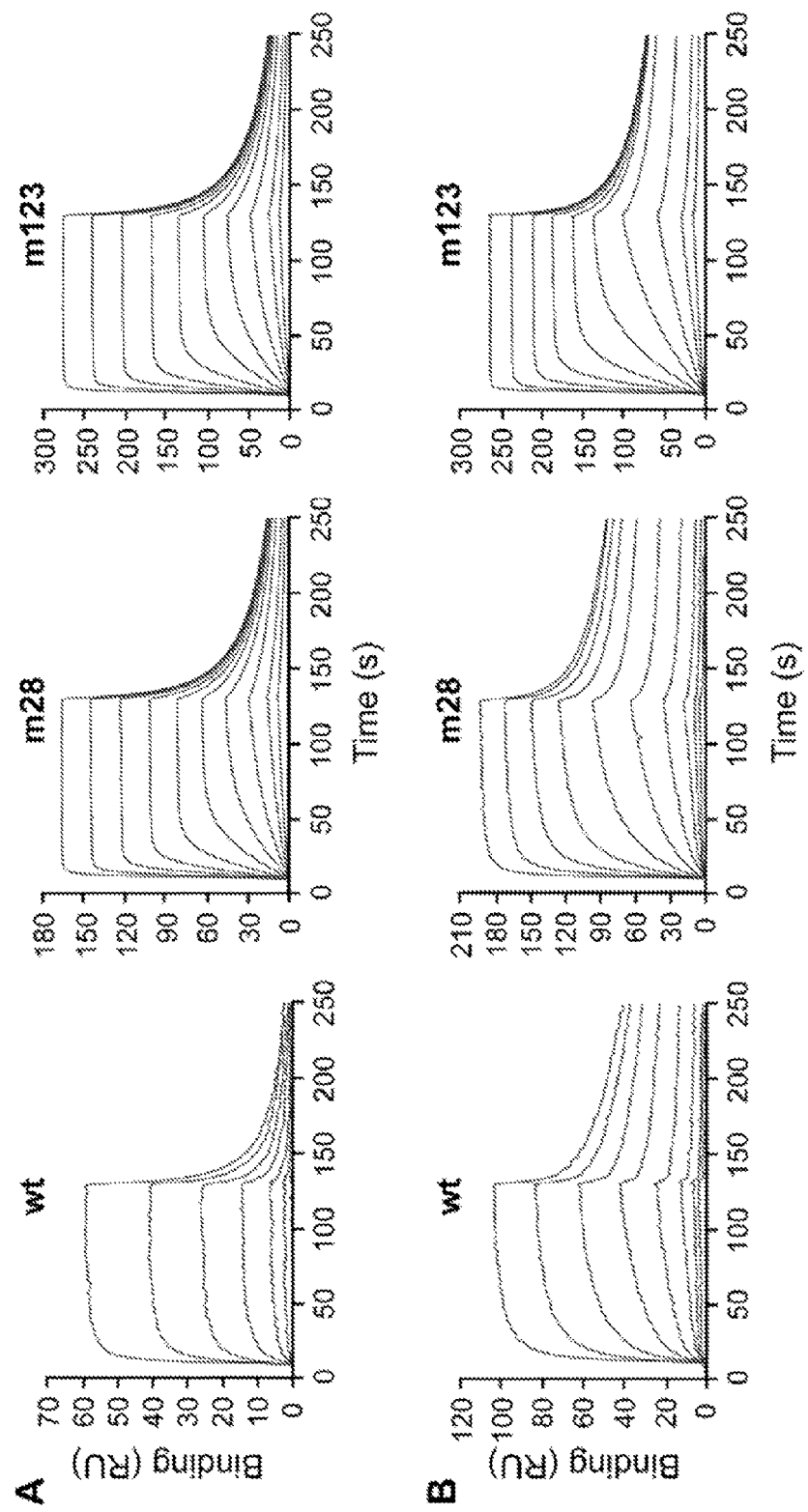
FIG. 27. Binding of wild-type EGF, mutant 28, and mutant 123 to the extracellular domain of human and murine EGFR. EGF binding to (A) hEGFR or (B) mEGFR was measured by surface plasmon resonance. Binding experiments were performed in triplicate and representative titration series sensorgrams are shown.

Real-time interactions of wild-type and mutant EGF with hEGFR and mEGFR were analyzed by SPR (FIG. 27 and Table 7). In these experiments, m28 and m123 bound 15- and 18-fold more tightly to hEGFR, respectively, than EGFwt. In addition, EGFwt bound to mEGFR with higher affinity than hEGFR. Compared to EGFwt, m28 and m123 bound four- and eight-fold more tightly to mEGFR, respectively. Since the EGF mutants were affinity-matured against human EGFR, it was not surprising that the difference between wild-type and mutant EGF binding to mEGFR was not as great as for hEGFR. For both mutants, improvements in $K_D$ over EGFwt resulted primarily from increased $k_{on}$ rather than decreased $k_{off}$, in agreement with cell surface studies above. Differences observed in absolute values of binding parameters from cell surface and SPR studies occur due to the removal of membrane constraints in SPR experiments, which use only EGFR extracellular domain (Brown P M, et al. The extracellular domain of the epidermal growth factor receptor. Studies on the affinity and stoichiometry of binding, receptor dimerization and a binding-domain mutant. Eur J Biochem. 1994; 225:223-233).

TABLE 7

Equilibrium binding affinities and kinetic rates of wild-type EGF, mutant 28, and mutant 123 binding to human and murine EGFR extracellular domain by SPR. Numbers in parenthesis denote fold-change over EGFwt.

|  | EGFwt | m28 | m123 |
|---|---|---|---|
| Human EGFR |  |  |  |
| $K_D$ (nM) | 90 ± 10 (—) | 6* ± 2 (15) | 4.9* ± 0.3 (18) |
| $k_{off}$ (s$^{-1}$) × 10$^{-3}$ | 18 ± 1 (—) | 11* ± 2 (1.6) | 12.4* ± 0.6 (1.5) |
| $k_{on}$ (M$^{-1}$s$^{-1}$) × 10$^5$ | 2.0 ± 0.2 (—) | 20* ± 8 (10) | 25* ± 1 (13) |
| Murine EGFR |  |  |  |
| $K_D$ (nM) | 18 ± 1 (—) | 4.5* ± 0.2 (4.0) | 2.27* ± 0.05 (7.9) |
| $k_{off}$ (s$^{-1}$) × 10$^{-3}$ | 2.7 ± 0.2) (— | 2.14* ± 0.08 (1.3) | 4.0* ± 0.1 (0.7) |
| $k_{on}$ (M$^{-1}$s$^{-1}$) × 10$^5$ | 1.47 ± 0.03 (—) | 4.76* ± 0.07 (3.2) | 17.6* ± 0.8 (12.0) |

*Statistical significance (p < 0.05) compared to EGFwt.

Figure 30:
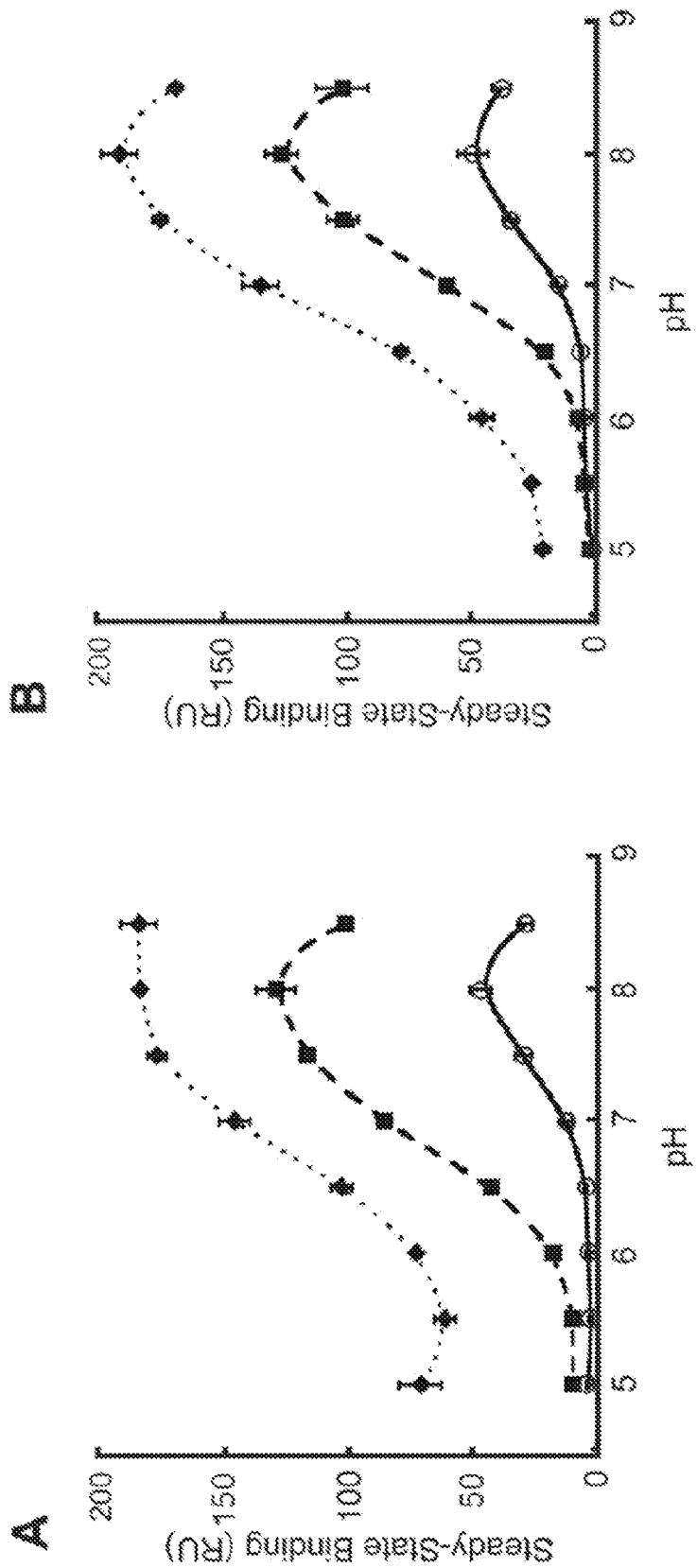
FIG. 30. pH dependence of wild-type and mutant EGF binding to (A) human and (B) murine EGFR. EGFwt (open circles, solid line), mutant 28 (black squares, dashed line), and mutant 123 (black diamonds, dotted line). Error bars denote standard deviations of triplicate experiments.

The pH sensitivity of the binding interaction of EGF ligands (200 nM) with hEGFR and mEGFR was measured by SPR over pH values ranging from 5.0 to 8.5. Measurement of the steady-state binding responses for each ligand-receptor pair across various pH values revealed that the interactions of EGFwt and m28 with EGFR were sensitive to changes in pH, while the binding of m123 with EGFR was much less so (FIG. 30).

EGF Mutants More Strongly Activate EGFR Compared to Wild-Type EGF.

Figure 28:
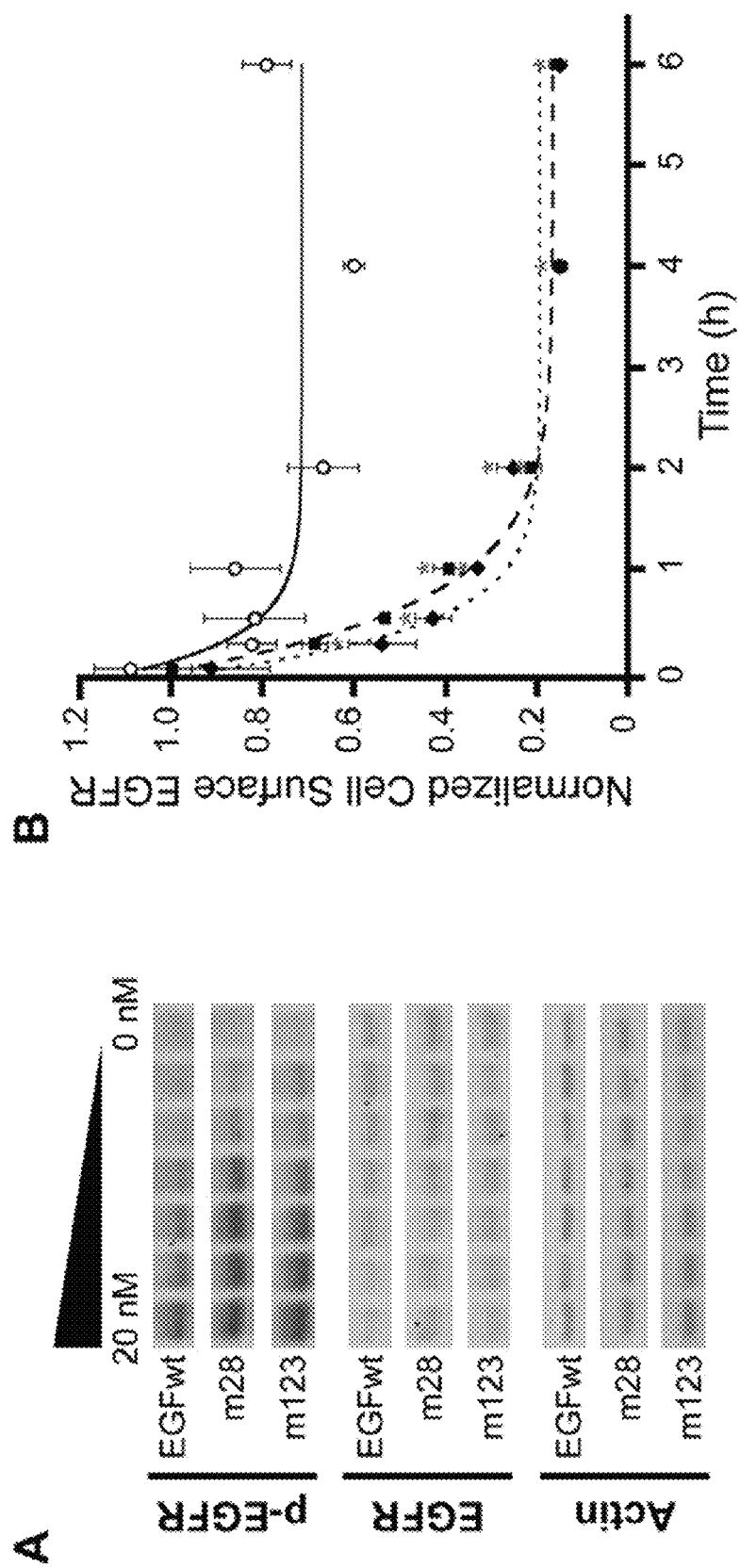
FIG. 28. Activation of EGFR by wild-type EGF, mutant 28, and mutant 123. (A) Western blot analysis of phosphorylated EGFR (p-EGFR, top panel), total EGFR (EGFR, middle panel) and actin loading control (Actin, lower panel) in BJ-5ta cells after treatment with EGF. (B) Downregulation of cell-surface EGFR in BJ-5ta cells in response to EGF stimulation. EGFwt (open circles, solid line), m28 (black squares, dashed line), or m123 (black diamonds, dotted line). Experiments were performed in triplicate and error bars denote standard error of the mean. (*) Statistical significance (p<0.05) compared to EGFwt.

We next measured the ability of wild-type and mutant EGF to activate EGFR on fibroblasts. We found that m28 and m123 more strongly stimulated EGFR phosphorylation in these cells at lower concentrations than EGRwt (FIG. 28A). Since EGFR is rapidly internalized into the cell upon activation of the intracellular tyrosine kinase domain (Wiley H S, et al. The role of tyrosine kinase activity in endocytosis, compartmentation, and down-regulation of the epidermal growth factor receptor. J Biol Chem, 1991; 266:11083-11094), downregulation of the receptor can serve as a surrogate measurement for receptor activation. Treatment of fibroblasts with m28 and m123 induced significantly increased EGFR downregulation compared to EGFwt, further indicating that the EGF mutants more strongly activate cell-surface EGFR (FIG. 28B).

Wild-Type EGF and m28 and m123 Elicit Similar Levels of Cell Proliferation.

Figure 31:
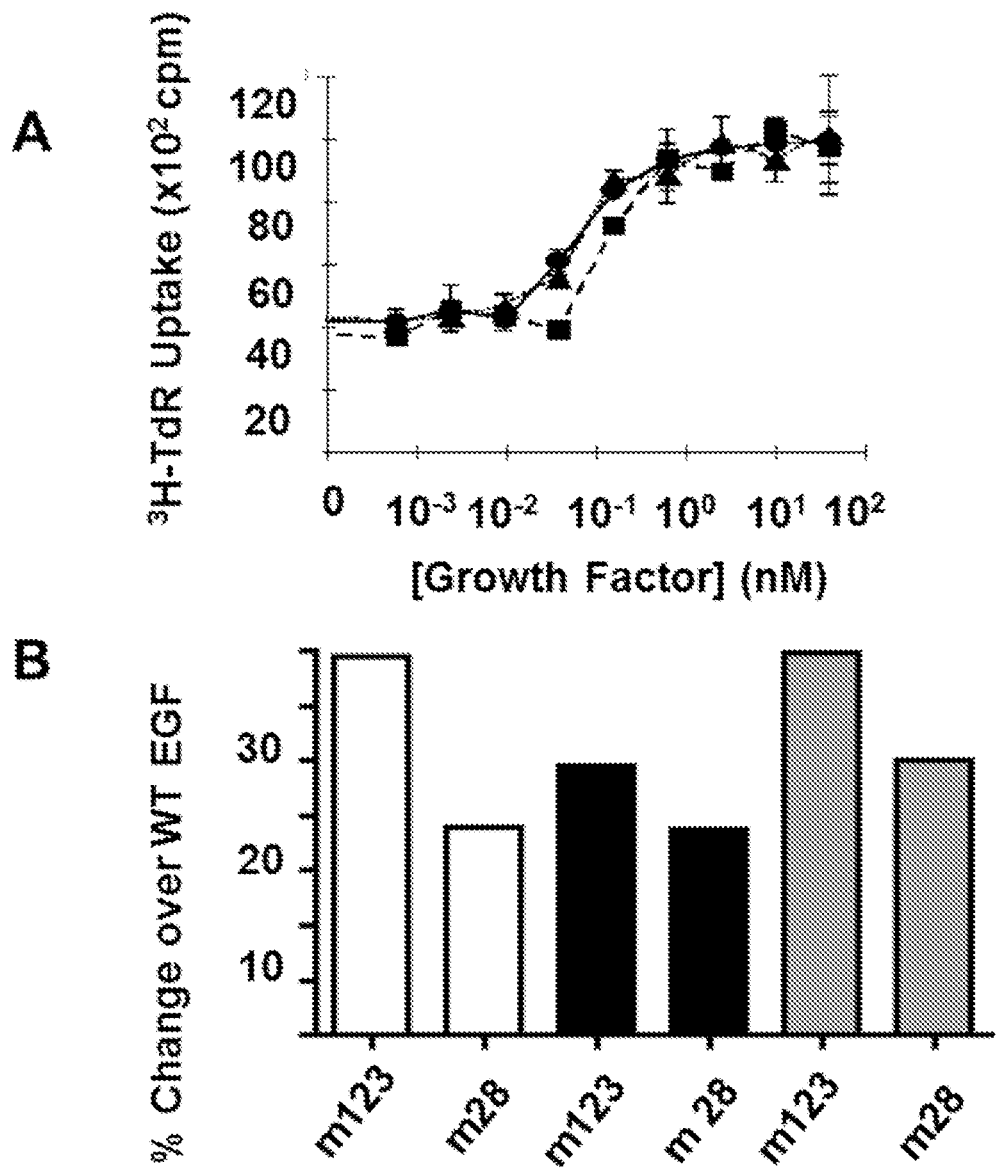
FIG. 31. Effects of EGF on cell proliferation and migration, Symbols are: wild-type EGF (circle), EGF mutant 28 (square), and EGF mutant 123 (triangle). (A) Proliferation of BJ-5ta cells incubated with varying concentrations of wild-type EGF or EGF mutants 28 and 123 was measured by 3H-TdR incorporation. (B) Chemotactic migration of NR6WT (white bars), BJ-5ta (black bars), and BALB/3T3 (grey bars). Cells were allowed to migrate through a porous membrane for 3 hr in response to 0.3 nM EGF proteins. Data is represented as the percent change in number of cells that migrated toward mutant EGF 28 or 123 compared to wild-type EGF.

We tested the ability of wild-type EGF and m28 and m123 to stimulate proliferation of BJ-5ta fibroblast cells. Wild-type EGF and mutants were solubly expressed in. *S. cerevisiae* and purified as described in Cochran et al PEAS 2006. Varying concentrations of EGF were added to cells and incubated for or 72 hours (BJ-5ta). Tritiated thymidine (3H-TdR) was added during the last 24 hours of incubation, and its incorporation into the newly synthesized DNA of proliferating cells was measured by scintillation counting. We found that there were no significant changes in the levels of cell proliferation that occurred upon treatment of fibroblasts with wild-type EGF or m28 and m123 (FIG. 31A).

EGF Mutants m28 and m123 Induce Enhanced Migration Compared to Wild-Type EGF.

We tested the effects of wild-type EGF and m28 and m123 on chemotactic cell migration using a transwell migration assay. We measured chemotaxis of NR6WT or BJ-5ta fibroblasts by quantifying how many cells migrated in a modified Boyden chamber after a 3-hour exposure to 0.3 nM EGF. Both m28 and m123 elicited increased chemotactic migration of NR6WT, BJ-5ta, and BALB/3T3 cells compared to wild-type EGF, with EGF mutant 123 consistently inducing higher numbers of migrated cells than EGF mutant 28 (FIG. 31B).

Discussion

We measured the EGFR binding affinities and kinetic rate constants of two previously identified EGF mutants, m28 and m123 (Cochran J R, et al. Improved mutants from directed evolution are biased to orthologous substitutions. Protein Eng Des Sel, 2006; 19:245-253), We showed through cell surface measurements and SPR that m28 and m123 have increased binding affinity for EGFR predominantly due to increased kinetic on-rates. The increased association rates of m28 and m123 were surprising since both mutants were discovered by screening combinatorial libraries under equilibrium binding conditions, which typically isolates mutants with decreased dissociation rates. We showed that m28 and m123 elicited increased EGFR activation compared to EGFwt, as measured by phosphorylation of the receptor tyrosine kinase domain and receptor downregulation. Interestingly, m123 had stronger binding at low pH compared to m28 and EGFwt. This difference implied that m123 might induce more intracellular receptor degradation compared to m28, yet both mutants exhibited greater levels of EGFR downregulation compared to EGFwt, suggesting that cell surface binding events drive this biological response.

Because of its important biological role, there has been much interest in EGF mutants with enhanced cell signaling for applications in wound healing and regenerative medicine (Moss. A J, et al. Rational design and protein engineering of growth factors for regenerative medicine and tissue engineering. Biochem Soc Trans. 2009; 37:717-721; Berlanga-Acosta J, et al. Epidermal growth factor in clinical practice—a review of its biological actions, clinical indications and safety implications. International Wound Journal. 2009; 6:331-346). Previous attempts at engineering EGF (Mullenbach G T, et al. Modification of a receptor-binding surface of epidermal growth factor (EGF): analogs with enhanced receptor affinity at low pH or at neutrality. Protein Eng. 1998; 11:473-480; Coco W M, et al. Growth factor engineering by degenerate homoduplex gene family recombination. Nat Biotechnol. 2002; 20:1246-1250; Reddy C C, et al. Engineering epidermal growth factor for enhanced mitogenic potency. Nat Biotechnol. 1996; 14:1696-1699; Souriau C. et al. A simple luciferase assay for signal transduction activity detection of epidermal growth factor displayed on phage, Nucleic Acids Res. 1997; 25:1585-1590) had mixed success, but highlighted the complex relationship between ligand binding and EGFR activation. While some studies concluded that receptor activation is directly proportional to equilibrium binding affinity (Mullenbach, supra; Souriau, supra), others found that equivalent or enhanced potency can be attained by EGF mutants with weaker receptor binding interactions than EGFwt (Coco, supra; Reddy, supra). Computational studies of cellular signaling and trafficking processes coupled to the activation of transmembrane receptors have attempted to explain these inconsistencies by highlighting the importance of receptor binding on-rates (Schoeberl B, et al. Computational modeling of the dynamics of the MAP kinase cascade activated by surface and internalized EGF receptors. Nat Biotechnol 2002; 20:370-375; Haugh J M. Mathematical model of human growth hormone (hGH)-stimulated cell proliferation explains the efficacy of hGH variants as receptor agonists or antagonists. Biotechnol Prog. 2004; 20:1337-1344).

This work represents the first experimental corroboration of the effects of increased ligand binding on-rates with enhanced receptor activation. We demonstrated that EGF mutants with faster association rates, but nearly equivalent dissociation rates, more strongly activated EGFR compared to EGRwt. Collectively, these studies indicate that while receptor activity is linked to ligand binding, the magnitude of the response can be altered solely by differences in the association rate of the interaction. Furthermore, these results provide a general strategy for engineering ligands that stimulate enhanced receptor activity (Jones D S, et al. Developing therapeutic proteins by engineering ligand-receptor interactions. Trends Biotechnol. 2008; 26:498-505).

Example 4

Preparation and Characterization of EGF Histidine Mutant Polypeptides

Mutants having biochemical properties consistent with EGF superagonist activity were prepared by the rational engineering method described above, as follows.

Materials and Methods

Preparation of EGF Histidine Mutants.

Three previously identified EGF mutants (mutants m100 (SEQ ID NO: 9), m102 (SEQ ID NO: 10), and m114 (SEQ ID NO:13)) originally disclosed in Cochran et al. ((2006) Protein Engineering, Design & Selection 19(6): 245-253) were selected for mutation, We selected m100 because of its high stability, m102 because it had the fastest binding on-rate, and m114 because it had the highest steady-state binding levels to EGFR at pH 7.5 relative to wild type EGF (SEQ ID NO: 1).

TABLE 7

Equilibrium binding affinities and kinetic EGFR-binding rate constants of select high-affinity EGF clones. Reported values are the averages of a single series of concentrations of each mutant flowed over two EGFR-immobilized flow cells and errors denote standard deviations.

| Ligand | Affinity (nM) | On-rate ($10^5$ $M^{-1}s^{-1}$) | Off-rate ($10^{-3}$ $s^{-1}$) |
| --- | --- | --- | --- |
| wt | 80 ± 30 | 4 ± 1 | 30 ± 10 |
| m100 | 30 ± 10 | 12 ± 2 | 30 ± 10 |
| m102 | 2.0 ± 0.1 | 13 ± 2 | 2.8 ± 0.3 |

The DNA was amplified from the pCT yeast display vector and extended by PCR to contain T7 promoter and terminator elements, yielding linear templates compatible with the CFPS system. PCR products of the correct lengths were purified by electrophoresis on a 2% agarose gel with a QIAquick Gel Extraction Kit (Qiagen).

Wild-type EGF (SEQ ID NO: 1), and mutants were ligated into the pK 7 plasmid, which includes T7 promoter and terminator elements (Kim et al, Biotechnol Prog, (2000) 16(3): p. 385-90), between the NdeI and SalI restriction sites using T4 DNA ligase (New England Biolabs). The resulting pK7-based plasmids were used as template for the creation of histidine point mutants by QuickChange site-directed mutagenesis (Strategene) using oligonucleotides with approximately 16 bp homology to the wild-type sequence on either side of the intended mutation. The resulting EGF ligands m100__16H (SEQ ID NO: 4), m102__16H (SEQ ID NO: 5), m114__16H (SEQ ID NO:14), m100__44H (SEQ ID NO:11), m102__44H (SEQ ID NO:12) and m114__44H (SEQ ID NO:15) were expressed by CFPS as described above.

Surface Plasmon Resonance Experiments.

All surface plasmon resonance experiments were performed at 25° C. on a Biacore 3000 instrument (Biacore) at the Stanford Protein and Nucleic Acids Facility, except for the kinetic binding studies with representative high-affinity EGF mutants, which were performed on a Biacore 3000 instrument in the Daugherty Lab at the University of California Santa Barbara. Biacore CM5 sensorchips, amine coupling reagents, regeneration solutions, and surfactant P20 were all purchased from GE Healthcare, Recombinant BTC, EGF, TGFα, and EGFR were purchased from Peprotech. Recombinant AR was purchased from R&D Systems.

pH Titration Binding Experiments.

Recombinant EGFR-ECD was immobilized in flow cells two and four of a Biacore CM5 sensorchip by amine coupling. To increase the accuracy of ligand binding measurements at low pH, EGFR-ECD was immobilized at high densities (approximately 6,000 RU). Flow cells one and three were activated and blocked without exposure to EGFR and served as reference surfaces. To measure the effects of pH on the binding interaction between ligands and EGFR, we used a series of degassed running buffers created using the Na2HPO4-citric acid buffering system with pHs ranging from 5.0 to 8.5. pH running buffers were supplemented with 50 mM NaCl, 0.1 mg/mL BSA, and 0.005% surfactant P20.

Ligands were diluted in pH running buffer and their steady-state binding levels to immobilized EGFR were monitored at a single concentration with a flow rate of 20 µL/min for 2 min. The EGFR surface could be successfully regenerated in most cases by washing with pH running buffer at 20 µL/min for 5 min. Binding cycles performed with some high-affinity EGF mutants required a 30 s injection of 10 mM sodium acetate, pH 4.5 at a flow rate of 50 µL/min to regenerate the EGFR surface. EGFR surface regeneration after binding of BTC was achieved with an extended dissociation phase of 20 min at a flow rate of 100 µL/min. When regeneration steps were necessary, they were followed by surface equilibration in running buffer for 2 min at a flow rate of 20 µL/min.

Final sensorgrams were obtained by subtracting the response of a reference flow cell from the binding response generated in an EGFR-immobilized flow cell, followed by subtraction of a blank buffer injection. Steadystate binding levels were measured at the plateau of the association phase of the sensorgram.

Binding of high-affinity EGF clones (m100 (SEQ ID NO: 10) and m102 (SEQ ID NO: 13)) was measured at 100 nM, and binding of EGF histidine mutants (m100__16H (SEQ ID NO: 4) and m102__16H (SEQ ID NO: 5)) was measured at 200 nM.

Kinetic Binding Rate Experiments.

Recombinant EGFR-ECD was immobilized by amine coupling in flow cells two and four of a Biacore CM5 sensorchip at levels appropriate for kinetic experiments with the ligands of the molecular weights considered here (approximately 4,000 RU Flow cells one and three were activated and blocked without exposure to protein and served as paired background reference cells.

All kinetic binding experiments were performed in degassed running buffer (PBS pH 7.4 containing 0.1 mg/mL BSA and 0.005% surfactant P20) at 25° C. Concentration series for each ligand were prepared with two-fold dilutions in running buffer. Ligand was flowed over the sensorchip surfaces at 30 µL/min for 2 min followed by a 5 min dissociation phase in running buffer at 30 µL/min. The dissociation phase afforded complete surface regeneration in most cases. However, some high-affinity EGF clones required an additional regeneration step including a 30 s pulse of 10 mM sodium acetate, pH 4.5 at 50 μL/min and BTC required washing with running buffer for 20 min at 100 μL/min. In all cases, regeneration phases were followed by a 2 min equilibration phase of washing with running buffer at 30 μL/min. Final sensorgrams were obtained by dual subtraction as previously described. The data was analyzed with BIA evaluation Software (Biacore, version 4.1) and simultaneously fit for affinity and kinetic parameters using a 1:1 Langmuir binding model.

Mass transfer control experiments were performed for each ligand at a mid-point concentration of the series according to the protocol above, but with ligand injection flow rates of 5, 15, and 75 μl/min. Linked reaction controls were conducted for each ligand at the highest concentration of the kinetic series according to the protocol above, but with ligand injection times of 1, 3, and 9 min. The highest ligand concentration tested was 400 nM for wild-type EGF, high-affinity EGF clones, and EGF histidine mutants.

EGFR Pulse Downregulation Assays.

BJ-5ta fibroblasts were treated with ice-cold serum-free media supplemented with 1 nM EGF for 2 hr at 4° C. Cells were then washed with ice-cold PBS, pre-warmed (to 37° C.) serum-free media was added to the cells, and they were incubated at 37° C. for times ranging from 0 to 120 min. After stimulation, cells were washed with ice-cold acidic buffer (pH 2.5) for 5 min to strip surface-bound EGF and fixed with 4% formaldehyde, Cell-surface EGFR was analyzed by flow cytometry using a primary antibody directed against EGFR and a secondary R-phycoerythrin-conjugated antibody.

Results

Rational Design of Histidine Point Mutations into High-Affinity EGF Mutants.

As a starting point for engineering EGF mutants with enhanced biochemical properties and pH-sensitive binding interactions, we selected three clones from the pool of high-affinity mutants characterized previously (Cochran et al. (2006) Protein Engineering, Design & Selection 19(6):245-253). Into these three mutants, we individually introduced additional histidine point mutations. Of the point mutations tested with wild-type EGF, we chose to incorporate S2H and Y44H because these two mutations did not decrease the binding interactions of EGFwt to EGFR at extracellular pH. We also reverted position 16 of each mutant to histidine, since we previously noted a correlation between mutations at this position and an increase in EGFR binding at low pH. Finally, we created double histidine point mutants for each high-affinity mutant by combining S2H and Y44H. This design strategy afforded twelve new high-affinity EGF histidine mutants, 4 for each of the three original high-affinity EGF mutants (Table 8).

TABLE 8

Amino acid sequences of mutant 100 (SEQ ID NO: 9), mutant 100-16H (SEQ ID NO: 4), mutant 100-44H (SEQ ID NO: 11), mutant 102 (SEQ ID NO: 10), mutant 102-16H (SEQ ID NO: 5), mutant 102-44H (SEQ ID NO: 12), mutant 114 (SEQ ID NO: 13), mutant 114-46H (SEQ ID NO: 14), and mutant 114-44H (SEQ ID NO: 15). Mutations are indicated in bold and underlined.

| Ligand | Sequence |
|---|---|
| m100 | NSNSECPLSHDGYCLNDGVCRYIEALDKYACNCVVGYVGERCQYRDLRRWELR |
| m100_16H | NSNSECPLSHDGYCLHDGVCRYIEALDKYACNCVVGYVGERCQYRDLRRWELR |
| m100_44H | NSNSECPLSHDGYCLNDGVCRYIEALDKYACNCVVGYVGERCQHRDLRRWELR |
| m102 | HSNSECPLSHDGYCLNDGVCMYIKALDTYACNCVVGYVGERCQYPDLKWWGLR |
| m102_16H | HSNSECPLSHDGYCLHDGVCMYIKALDTYACNCVVGYVGERCQYPDLKWWGLR |
| m102_44H | HSNSECPLSHDGYCLNDGVCMYIKALDTYACNCVVGYVGERCQHPDLKWWG**LR |
| m114 | SRGSKCPPSHDGYCLQGGVCMYIEALDRYACNCVVGYAGERCQYRDLTWWGRR |
| m114_26H | SRGSKCPPSHDGYCLHGGVCMYIEALDRYACNCVVGYAGERCQYRDLTWWGRR |
| m114_44H | SRGSKCPPSHDGYCLQGGVCMYIEALDRYACNCVVGYAGERCQHRDLTWWGRR |

Comparative Binding of EGF Histidine Point Mutants to EGFR at Extracellular and Endosomal pH.

Figure 32:
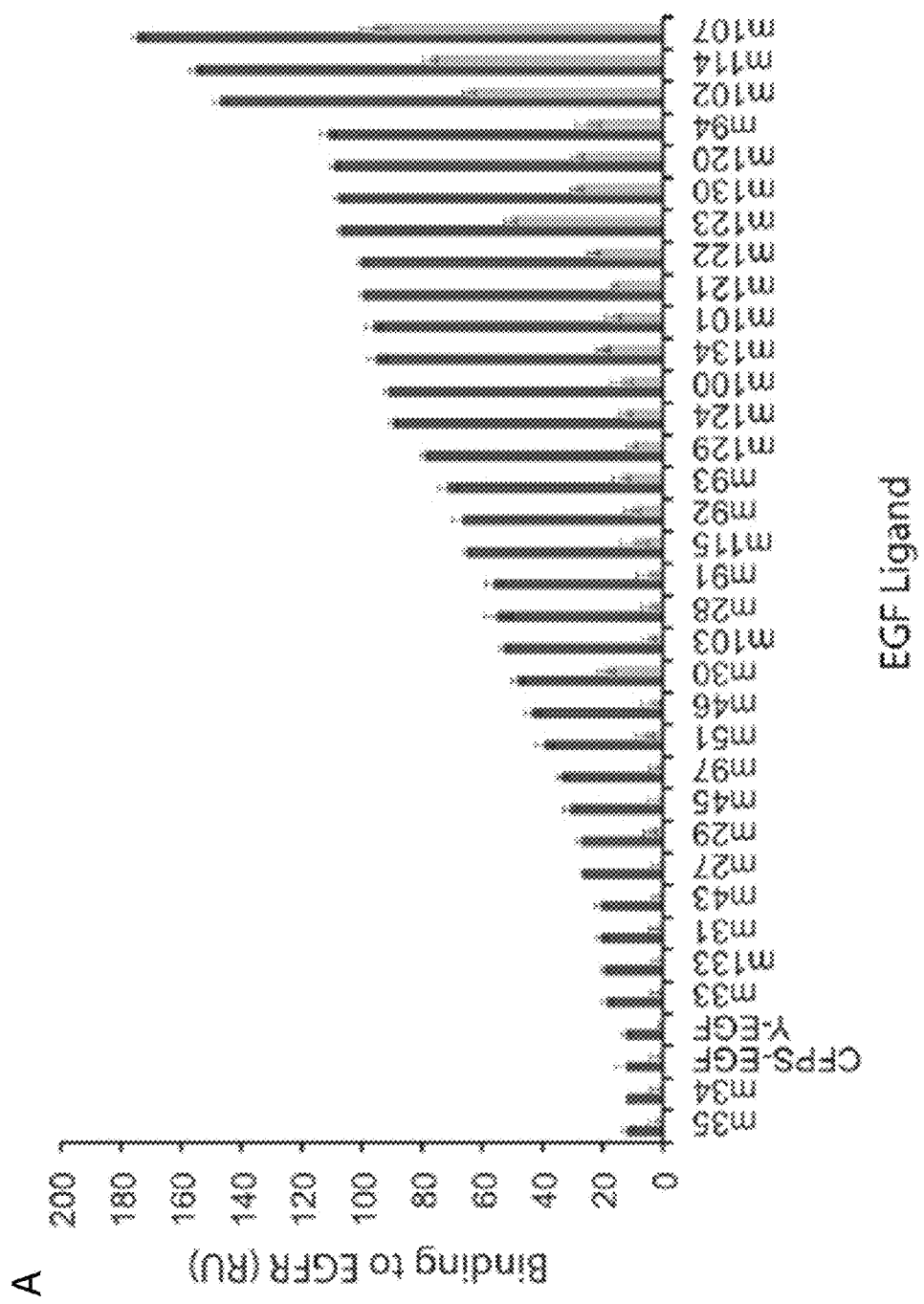
FIG. 32. Differential binding of mutant EGF polypeptides and histidine mutants engineered therefrom to EGFR at extracellular and endosomal pH. Binding levels shown denote steady-state responses at pH 7.5 (dark blue) and pH 5.5 (light blue) measured in triplicate for parent mutants (A) and in duplicate for histidine mutants prepared from parent mutants m100, m102 and m114 by SPR over two EGFR-immobilized flow cells. Error bars denote standard deviations.
Figure 32:
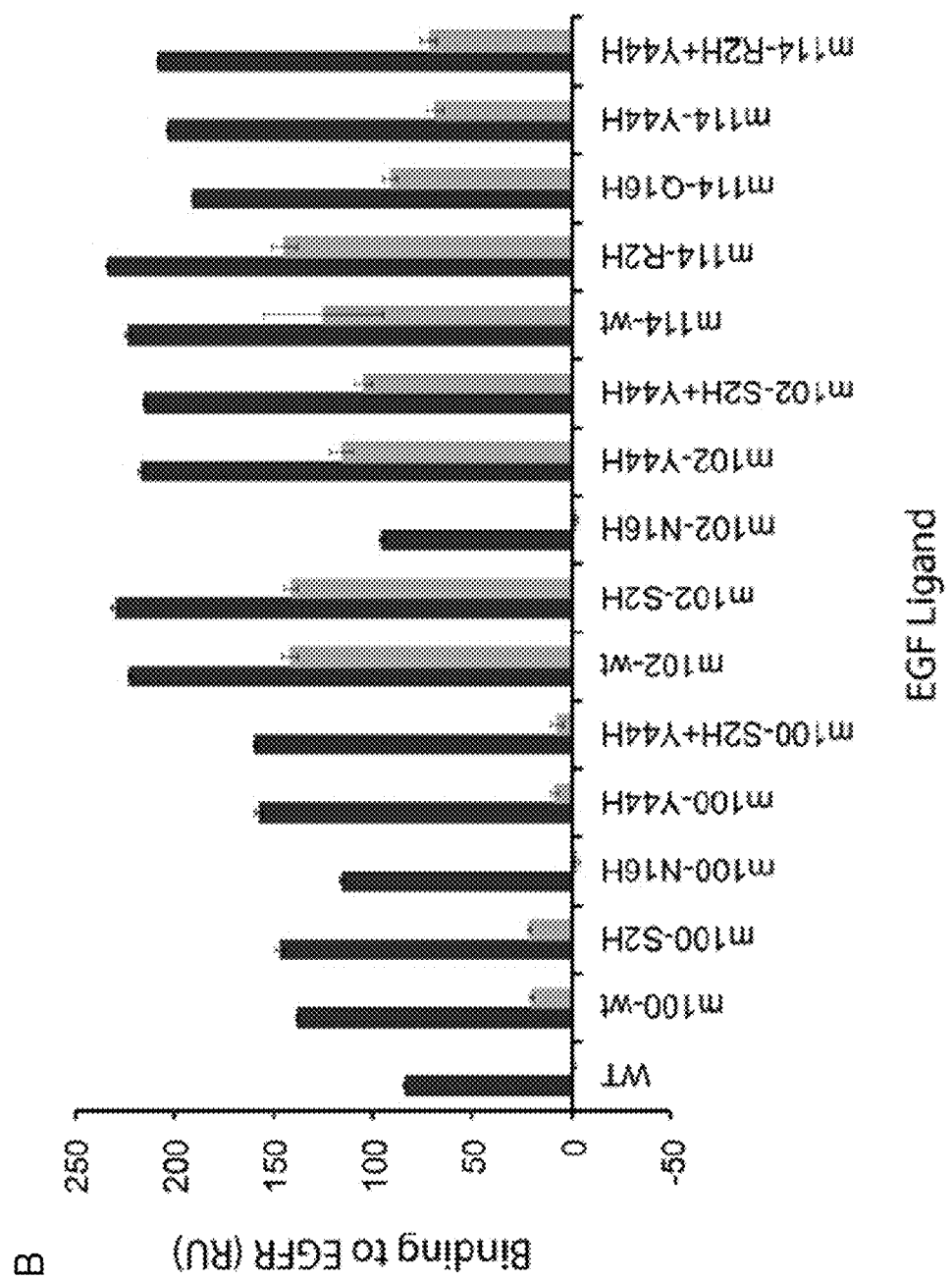

The effect of the introduced histidine mutations on the binding of high-affinity EGF mutants to EGFR was monitored by SPR. Each ligand was diluted to a single concentration in running buffer at pH 7.5 or 5.5 and flowed over an EGFR-immobilized surface. As an indication of their relative binding affinities and the pH sensitivity of the binding interaction with EGFR, we measured the steady-state response level of each ligand at extracellular and endosomal pH (FIG. 32). From these analyses, we found that introducing a histidine at the second position along the EGF polypeptide, either alone or with an additional histidine mutation at position 44, had no effect on the binding of the ligand to EGFR at either pH. Reversion of EGF position 16 to histidine decreased the steady-state EGFR-binding levels of m100__16H and m102__16H at pH 7.5 to approximately 84% and 43%, respectively, that of their corresponding 'wild-type' clones and abolished all EGFR binding at pH 5.5. Introduction of histidine at residue 44 slightly increased the steady-state binding level of m100 at pH 7.5 and reduced steady-state binding levels at pH 5.5 to less than 5% the level at extracellular pH. For m102, the Y44H point mutation had less of an effect; the binding level of m102-Y44H was slightly lower than m102wt at pH 7.5, and the binding of m102-Y44H at pH 5.5 was approximately half (compared to 62% for m102 wt) the level at pH 7.5. While the Y44H point mutation also had a relatively small effect on the binding of m114 to EGFR at pH 7.5, it decreased the steady-state binding levels at pH 5.5 from approximately 64% to 31% that of m114wt.

Kinetic Rates of EGF Histidine Point Mutants Binding to EGFR.

Figure 33:
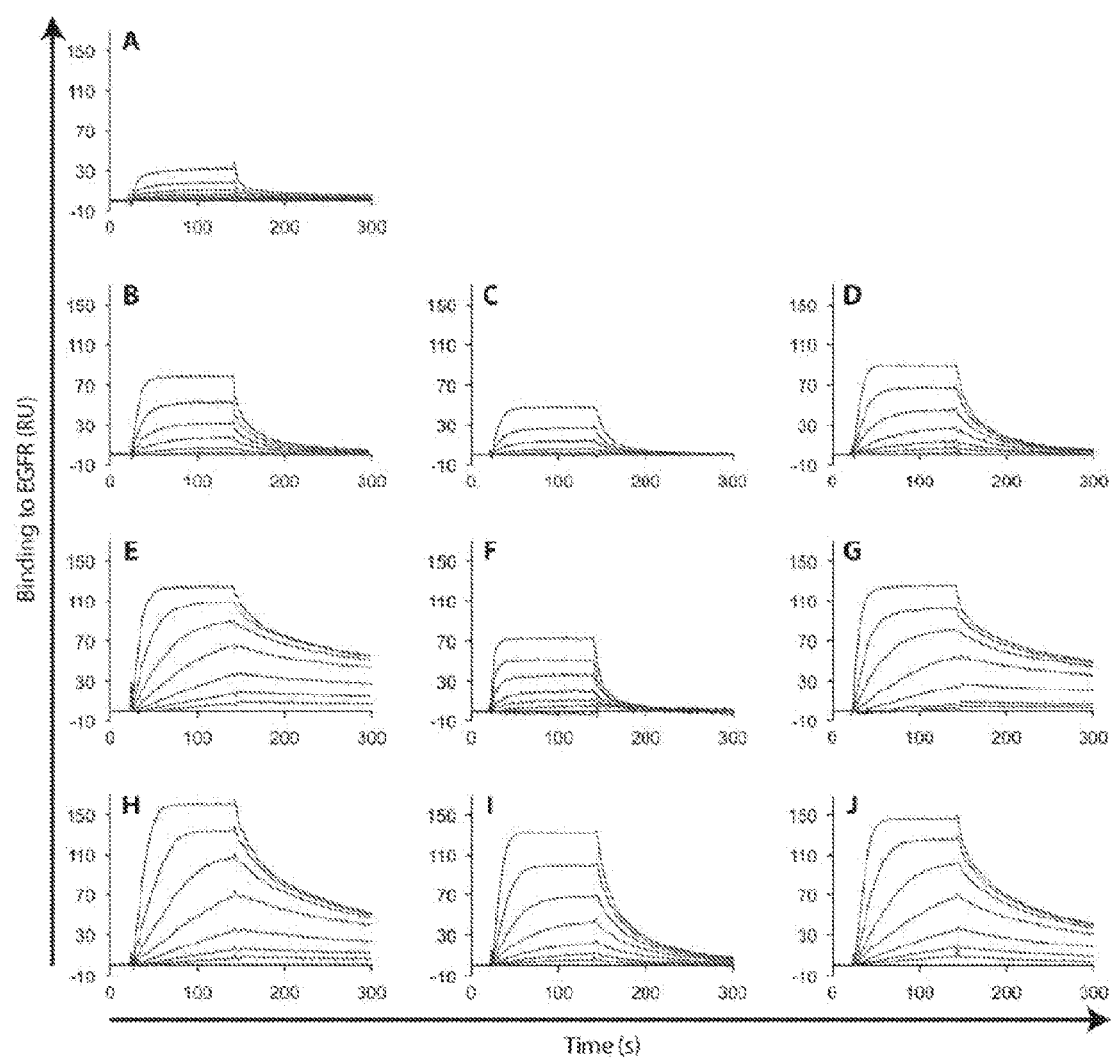
FIG. 33. Representative surface plasmon resonance sensorgrams for high-affinity. EGF histidine mutants binding to immobilized EGFR. (A) wild-type EGF, (B) m100wt, (C) m100_16H, (O) m100_44H, (E) m102wt, (F) m102_16H, (G) m102_44H, (H) m114wt, (I) m114-16H, (J) m114-44H. Concentration series depict two-fold dilutions beginning with 100 nM.

We measured the equilibrium binding affinities and kinetic rate constants for the interactions of the N16H and Y44H point mutations as well as for the original EGF mutants by SPR with immobilized EGFR at pH 7.5 as described above (FIG. 33 and Table 9, below). We found that none of the histidine mutations altered the on-rates of the binding of the EGF mutants to EGFR at extracellular pH. Instead, when histidine was reinstated at position 16 in the high-affinity EGF mutants, the off-rates of the EGFR binding interactions were significantly increased for all three clones. As suggested by the observed steady-state binding levels, the Y44H point mutation has little effect on the affinity and kinetic rates of the binding interaction with EGFR at pH 7.5.

TABLE 9

Equilibrium binding affinities and kinetic EGFR-binding rate constants of EGF histidine mutants. Reported values are the averages of duplicate concentration series flowed over a single EGFR immobilized flow cell and errors denote standard deviations.

| Ligand | $K_D$ (nM) | $k_{on}$ ($10^5$ $M^{-1}$ $s^{-1}$) | $k_{off}$ ($10^{-3}$ $s^{-1}$) |
| --- | --- | --- | --- |
| m100wt (SEQ ID NO: 9) | 30 ± 10 | 12 ± 2 | 30 ± 10 |
| m100_16H (SEQ ID NO: 4) | 90 ± 10 | 9 ± 3 | 90 ± 10 |
| m100-Y44H (SEQ ID NO: 11) | 24 ± 8 | 12 ± 3 | 30 ± 10 |
| m102wt (SEQ ID NO: 10) | 2.0 ± 0.1 | 13 ± 2 | 2.8 ± 0.3 |
| m102_N16H (SEQ ID NO: 5) | 50 ± 10 | 20 ± 10 | 90 ± 30 |
| m102_Y44H (SEQ ID NO: 12) | 3 ± 1 | 15 ± 2 | 4 ± 1 |
| m114wt (SEQ ID NO: 13) | 8 ± 1 | 10 ± 1 | 8 ± 2 |
| m114-Q16H (SEQ ID NO: 14) | 20 ± 10 | 13 ± 2 | 30 ± 10 |
| m114-Y44H (SEQ ID NO: 15) | 7 ± 1 | 11 ± 3 | 8 ± 2 |

Activation of EGFR after Stimulation with EGF Histidine Point Mutants.

Figure 34:
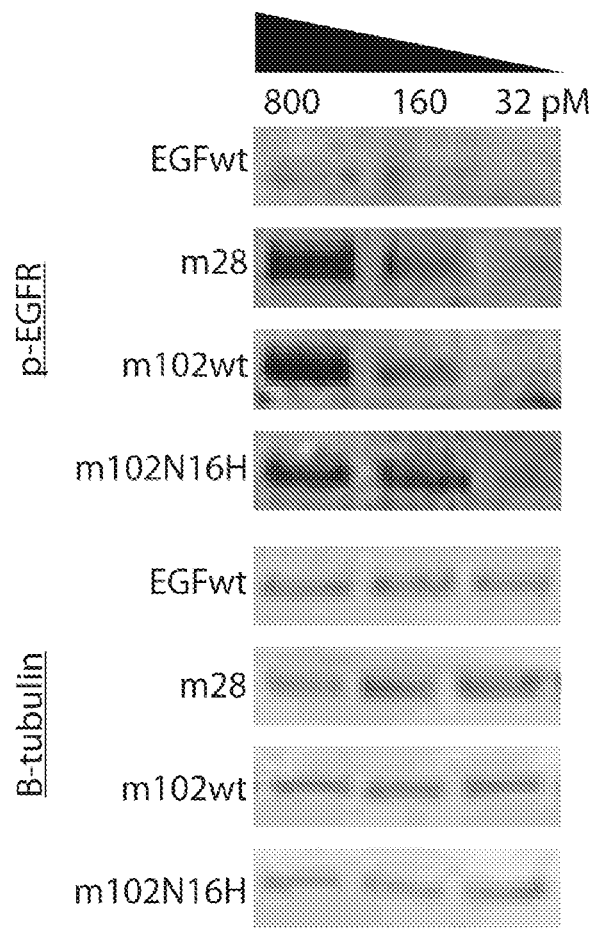
FIG. 34. Activation of EGFR by EGFwt, m102wt, and m102_16H. Western blot analysis of phosphorylated EGFR (p-EGFR, top panel) and beta-tubulin loading control (B-tubulin, lower panel) in BJ-5ta cells after treatment with EGF for 15 min.
Figure 35:
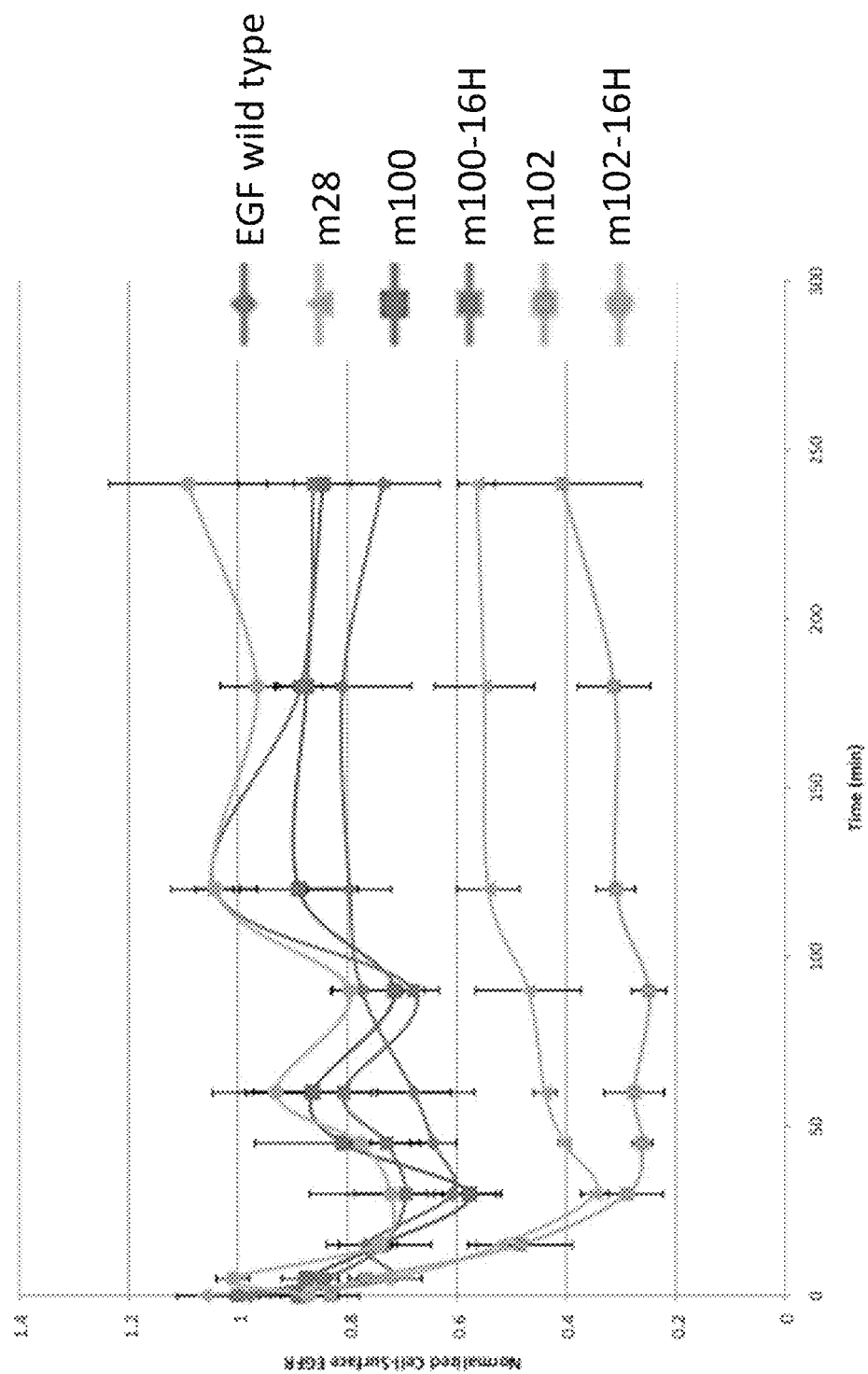
FIG. 35. Downregulation of cell-surface EGFR in fibroblast cells in response to EGF stimulation. Pulse stimulation of human BJ5-ta fibroblast cells with wild-type (blue), m28 (green), m100 (red), m100_16H (purple), m102 (cyan), or m102_16H (orange) EGF shows that both histidine point mutants elicit less downregulation compared to wild-type EGF.

The capacity of EGFR to recycle to back to the cell surface, and thus continue to participate in signaling events, after stimulation with the EGF histidine point mutants was measured using a pulse downregulation experiment as described above. We observed lower levels of EGFR degradation after treatment with m100_16H and m102_16H compared to m100 and m102, respectively (FIG. 35). These results demonstrate that the combination of increased binding off-rates and decreased binding at endosomal pH leads to improved recycling of EGFR. Such improved EGFR recycling is an important contribution to the enhanced biological activity profiles of the histidine point mutants. In addition to downregulation, we measured the ability of EGF histidine point mutants to activate EGFR, as indicated by phosphorylation of the receptor (FIG. 34). We found that treatment of fibroblast cells with m102_16H induced stronger activation of EGFR at lower ligand concentrations than either EGFwt, the high-affinity mutant m28, or its parental mutant m102. Together, these EGFR downregulation and phosphorylation results indicate that EGF histidine point mutants are EGF superagonists, as they more strongly activate cell-surface EGFR while promoting less downregulation of EGFR from the cell surface than wild type EGF or other high-affinity EGF clones.

The preceding merely illustrates the principles of the invention. It be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

That which is claimed is:

1. An isolated polypeptide comprising an amino acid sequence selected from the group consisting of SEQ ID NO:2, 3, 4, 5, 11, 12, 14 and 15.

* * * * *